US010072292B2

(12) United States Patent
Matsunami et al.

(10) Patent No.: US 10,072,292 B2
(45) Date of Patent: Sep. 11, 2018

(54) COMPOSITIONS AND METHODS FOR ENHANCING ODORANT RECEPTOR ACTIVITY

(71) Applicant: Duke University, Durham, NC (US)

(72) Inventors: Hiroaki Matsunami, Durham, NC (US); Yun Li, Philadelphia, PA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 15/477,873

(22) Filed: Apr. 3, 2017

(65) Prior Publication Data

US 2017/0283872 A1 Oct. 5, 2017

Related U.S. Application Data

(63) Continuation of application No. 14/754,940, filed on Jun. 30, 2015, now Pat. No. 9,611,308, which is a continuation of application No. 13/513,600, filed as application No. PCT/US2010/059093 on Dec. 6, 2010, now Pat. No. 9,068,226.

(60) Provisional application No. 61/266,805, filed on Dec. 4, 2009.

(51) Int. Cl.
*C12Q 1/68* (2018.01)
*C07K 14/705* (2006.01)
*C12Q 1/6881* (2018.01)

(52) U.S. Cl.
CPC ...... *C12Q 1/6881* (2013.01); *C07K 14/70571* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| 7,425,445 B2 | 9/2008 | Matsunami |
| 7,691,592 B2 | 4/2010 | Matsunami |
| 7,838,288 B2 | 11/2010 | Matsunami |
| 7,879,565 B2 | 2/2011 | Matsunami |
| 2009/0124003 A1 | 5/2009 | Matsunami |
| 2010/0222561 A1 | 9/2010 | Matsunami |

OTHER PUBLICATIONS

Abdalla, S., H. Lother, U. Quitterer, "AT1-receptor heterodimers show enhanced G-protein activation oand altered receptor sequestration," Nature 407, 94-98 (Sep. 7, 2000).
Barki-Harrington, L., L.M. Luttrell, H.A. Rockman, "Dual Inhibition of β-Adrenergic and Angiotensin II Receptors by a Single Antagonist," (2003), vol. 108, pp. 1611-1618.
Boekhoff, E., Tareilus, J. Strotmann, H., Breer, "Rapid activation of alternative second messenger pathways in olfactory cilia from rats by different odorants," EMBO J 9, 2453 (Aug. 1990).
Bozza, T., et al., "Odorant Receptor Expression Defines Functional Units in the Mouse Olfactory System," (2002) J Neurosci 22, 3033-3043.
Brady AE, et al. "Centrally Active Allosteric Potentiators of the M4 Muscarinic Acetylcholine Recptor Reverse Amphetamine-Induced Hypterlocomotor Activity in Rats," (2008) J Pharmacol. Exp. Ther. 327 (3): 941-53.
Buck L., R. Axel, "A Novel Multigene Family May Encode Odorant Receptors: A Molecular Basis for Odor Recognition," Cell 65, 175-187 (Apr. 5, 1991).
Buck L.B., "Information Coding in the Vertebrate Olfactory System," Annual review of neuroscience 19, 517-544 (1996).
Bush, C.F. et al., "Specificity of Olfactory Receptor Interactions with Other G Protein-coupled Receptors," J Biol Chem 282, 19042-19051 (Jun. 29, 2007).
Chabre, M., M. le Maire, "Monomeric G-Protein-Coupled Receptor as a Functional Unit," Biochemistry 44, 9395-9403 (2005).
Chan W.Y., et al., "Allosteric modulation of the muscarinic M4 receptor as an approach to treating schizophrenia," (2008) PNAS 105 (31), pp. 10978-10983.
Firestein S., "How the olfactory system makes sense of scents," Nature 413, 211-218 (2001).
Gaillard, I., et al., "A single olfactory receptor specifically binds a set of odorant molecules," (2002) Eur J Neurosci 15, 409-418.
Gimelbrant, A. A., et al., "Olfactory Receptor Trafficking Involves Conserved Regulatory Steps," (2001) J Biol Chem 276, 7285-7290.
Hague, C. et al., "Olfactory receptor surface expression is driven by association with the β2-adrenergic receptor," Proc Natal Acad Sci USA 101, 13672-13676 (Sep. 14, 2004).
Hansen, J. L., et al., "Lack of Evidence for AT1 R/B2R Heterodimerization in COS-7, HEK293, and NIH3T3 Cells," J Biol Chem 284, 1831-1839 (Jan. 16, 2009).
Hatt, H., et al., "Cloning, Functional Expression and Characterization of a Human Olfactory Receptor," (1999) Cell Mol Biol 45, 285-291.
Kajiya, K., et al., "Molecular Bases of Odor Discrimination: Reconstitution of Olfactory Receptors that Recognize Overlapping Sets of Odorants," (2001) J Neurosci 21, 6018-6025.
Katada, S., T. Nakagawa, H. Kataoka, K. Touhara, "Odorant response assays for a heterologously expressed olfactory receptor," Biochme Biophys Res Commun 305, 964-969 (Jun. 13, 2003).

(Continued)

*Primary Examiner* — John D Ulm
(74) *Attorney, Agent, or Firm* — Casimir Jones, SC; Robert A. Goetz

(57) ABSTRACT

The present invention relates to polypeptides capable of modulating odorant receptor activation. In particular, the present invention provides polypeptides (e.g., type 3 muscarinic actetylcholine receptor M3) capable of enhancing odorant receptor activation. The present invention further provides assays for the detection of ligands specific for various odorant receptors. Additionally, the present invention provides methods of screening for polypeptide polymorphisms and mutations associated with odorant receptor activation (e.g., polymorphisms and mutations associated with muscarinic actetylcholine receptor polypeptides (e.g., M1, M2, M3, M4, M5)), as well as methods of screening for therapeutic agents, ligands, and modulators of such proteins.

11 Claims, 61 Drawing Sheets
Specification includes a Sequence Listing.

(56) References Cited

OTHER PUBLICATIONS

Klasen, K. et al., "Odorant-stimulated Phosphoinositide Signaling in Mammalian Olfactory Receptor Neurons" 2010 Cell Signal, vol. 22, pp. 150-157.

Krautwurst, D., et al., "Identification of Ligands for Olfactory Receptors by Functional Expression of a Receptor Library," (1998) Cell 95, 917-926.

Lancet, D., N. Ben-Arie, "Olfactory receptors," Curr Biol 3, 668-674 (Oct. 1, 1993).

Lu, M., et al., "Endoplasmic Reticulum Retention, Degradation, and Aggregation of Olfactory G-Protein Coupled Receptors," (2003) Traffic 4, 416-433.

Luttrell, L.M., "Reviews in Molecular Biology and Biotechnology: Transmembrane Signaling by G Protein-Coupled Recptors," Molecular Biotechnology 39, 239-264 (2008).

Malnic, B., J. Hirono, T. Sato, L. B. Buck, "Combinatorial Receptor Codes for Odors," Cell 96, 713-723 (Mar. 5, 1999).

McClintock, T.S., and Sammeta, N., "Trafficking prerogatives of olfactory receptors," (2003) Neuroreport 14, 1547-1552.

McLintock, T.S. et al., "Functional Expression of Olfactory-Adrenergic Receptor Chimeras and Intracellular Retention of Heterologously Expressed Olfactory Receptors" (1997) Brain Res Mol. Brain Res , vol. 48, pp. 270-278.

Milligan, G., "G protein-coupled receptor dimerisation: Molecular basis and relevance to function," Biochim Biophys Acta 1768, 825-835 (Apr. 2007).

Mombaerts, "Genes and Ligands for Odorant, Vomeronasal and Taste Receptors," P. Nat Rev Neurosci 5, (2004) 263-278.

Prinster, S.C., C. Hague, R.A. Hall, "Heterodimerization of G Protein-Coupled Recptors: Specificity and Functional Significance," Pharmacol Rev 57, 289-298 (Sep. 1, 2005).

Raming, K., et al., "Cloning and expression of odorant receptors," (1993) Nature 361, 353-356.

Reed, R. R., "Signaling Pathways in Odorant Detection," Neuron 8, 205-209 (Feb. 1992).

Saito, H., A. Chi, H. Zhuang, H. Matsunami, J. D. Mainland, Sci Signal 2, ra9 (2009), "Odor Coding by a Mammalian Receptor Repertoire", pp. 1-28.

Saito, H., M. Kubota, R.W. Roberts, Q. Chi, H. Matsunami, "RTP Family Members Induce Functional Expression of Mammalian Odorant Receptors," Cell 119, 679-691 (Nov. 24, 2004).

Scapecchi S, et al., "Highly chiral muscarinic ligands: the discovery of (2S,2'R,3'S,5'R)-1-methyl-2-(2-methyl-1,3-oxathiolan-5-yl)pyrrolidine 3-sulfoxide methyl iodide, a potent, functionally selective, M2 partial agonist." J Med Chem. Mar. 23, 2006;49(6):1925-31.

Shepherd, G.M., "Discrimination of Molecular Signals by the Olfactory Recepto Neuron" Neuron, vol. 13, pp. 171-790 (Oct. 1994).

Spehr, M. et al., "Identification of a Testicular Odorant Receptor Mediating Human Sperm Chemotaxis" (2003) Science, vol. 299, pp. 2054-2058.

Touhara, K., et al., "Functional identification and reconstitution of an odorant receptor in single olfactory neurons," (1999) Proc Natl Acad Sci USA 96, 4040-4045.

Von Dannecker, L. E., A.F. Mercandante, B. Malnic, "Ric-8B promotes functional expression of odorant receptors," Proc Natl Acad Sci USA 103, 9310-9314 (Jun. 13, 2006).

Zeng, F.Y., J. Wess, "Identification and Molecular Characterization of m3 Muscarinic Receptor Dimers," J. Biol. Chem. 274, 19487-19497 (Jul. 2, 1999).

Zhao, H. et al., "Functional Expression of a Mammalian Odorant Receptor" (1998) Science, vol. 279, pp. 237-242.

Zhuang, H., H. Matsunami, "Synergism of Accessory Factors in Functional Expression of Mammalian Odorant Receptors," J Biol Chem 282, 15284-15293 (May 18, 2007).

Zhuang, H., H. Matsunami, "Evaluating Cell-Surface Expression and Measuring Activation of Mammalian Odorant Receptors in Heterologous Cells" Nat Protoc., vol. 3, pp. 1402-1413 (2008).

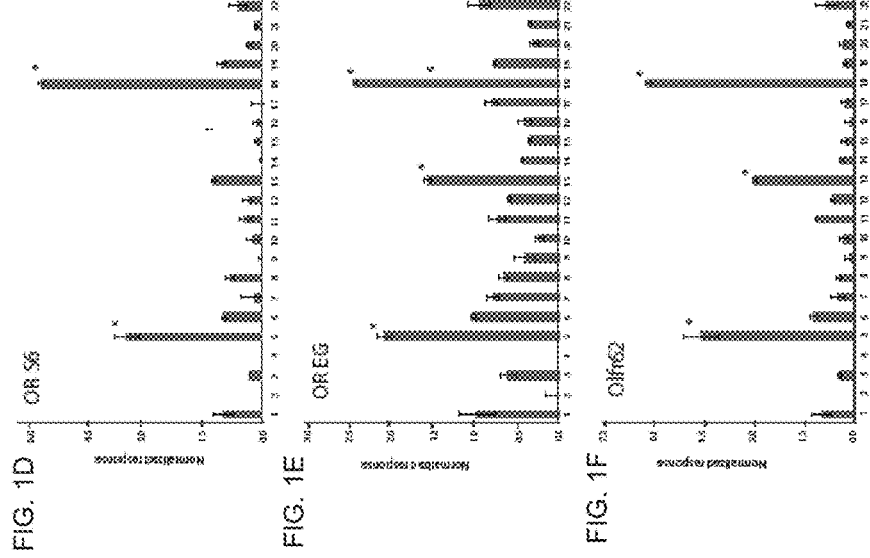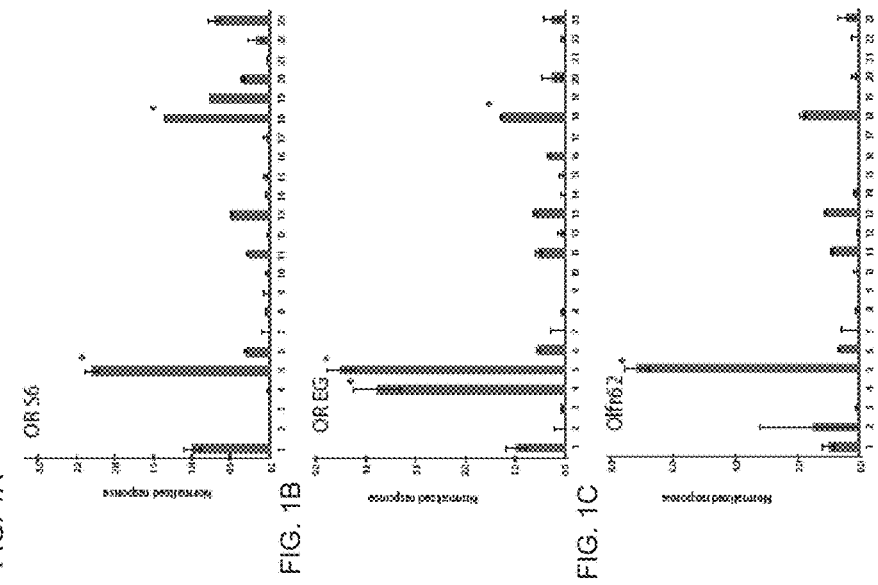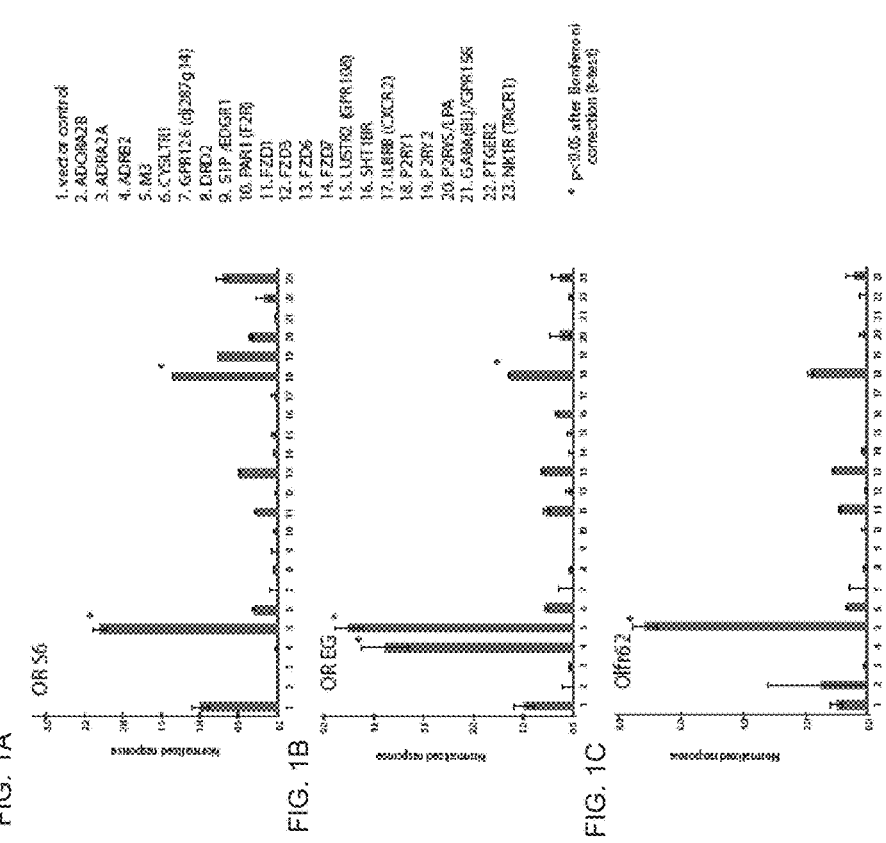

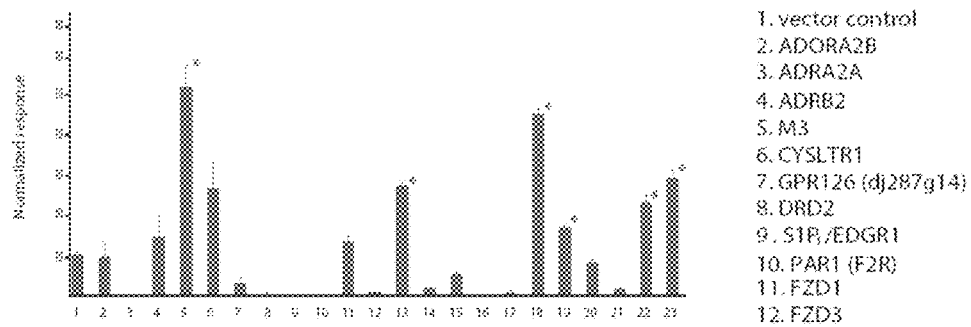
FIG. 2A OR S6
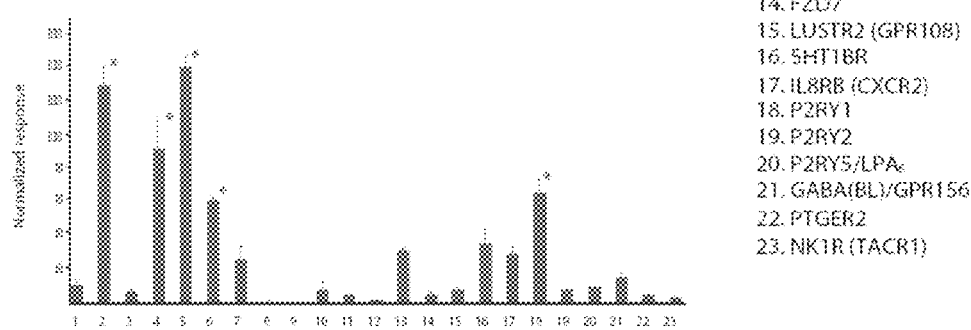
FIG. 2B OR EG
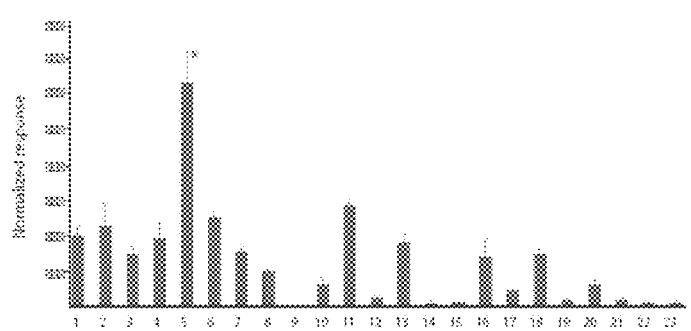
FIG. 2C Olfr62
1. vector control
2. ADORA2B
3. ADRA2A
4. ADRB2
5. M3
6. CYSLTR1
7. GPR126 (dj287g14)
8. DRD2
9. S1R/EDGR1
10. PAR1 (F2R)
11. FZD1
12. FZD3
13. FZD6
14. FZD7
15. LUSTR2 (GPR108)
16. 5HT1BR
17. IL8RB (CXCR2)
18. P2RY1
19. P2RY2
20. P2RY5/LPA
21. GABA(BL)/GPR156
22. PTGER2
23. NK1R (TACR1)
\* p<0.05 after Bonferroni correction (t-test)

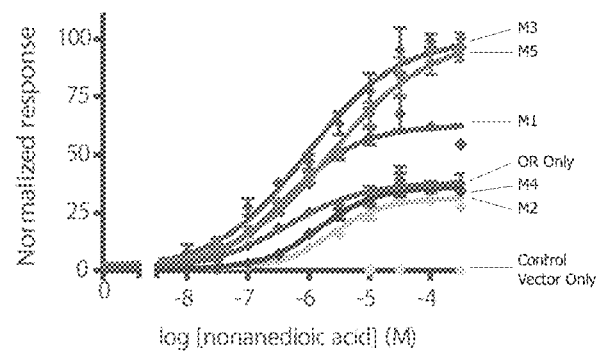
FIG. 3A Rho-tagged S6
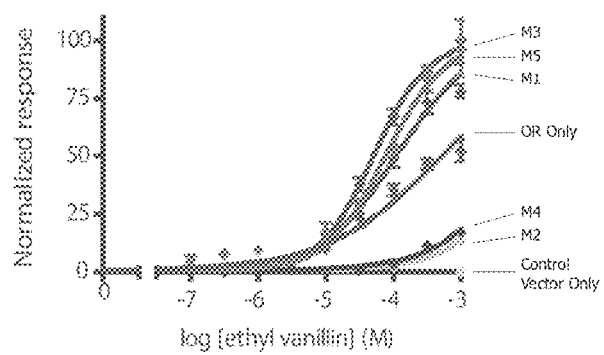
FIG. 3B Rho-tagged OREG

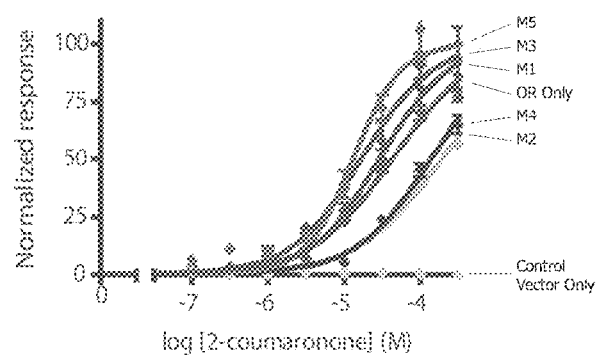

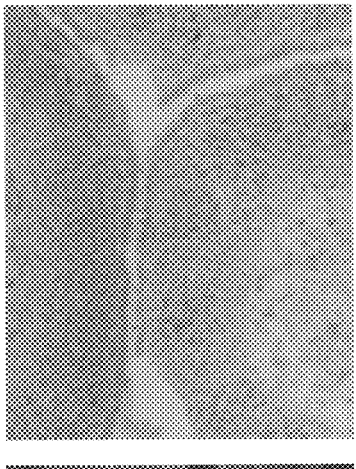
FIG. 4A M3
FIG. 4B OMP
FIG. 4C IL8RB
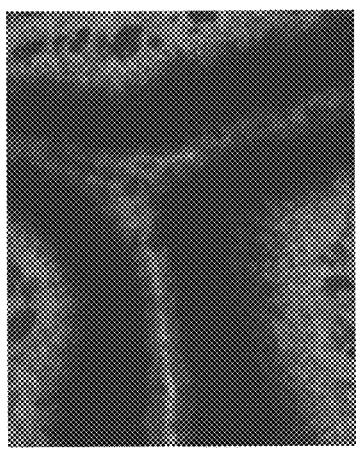
olfactory epithelium
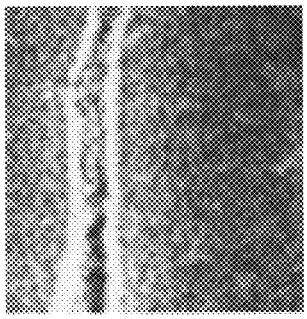
FIG. 4G ACIII
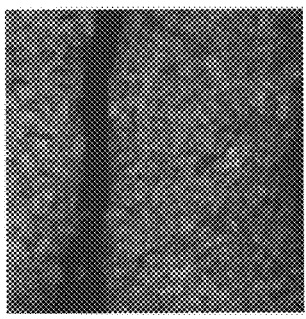
FIG. 4F M5
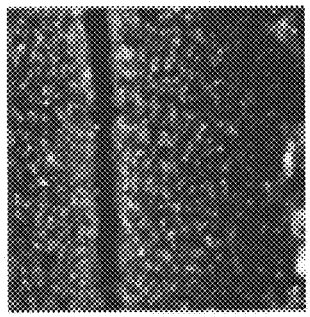
FIG. 4E M1
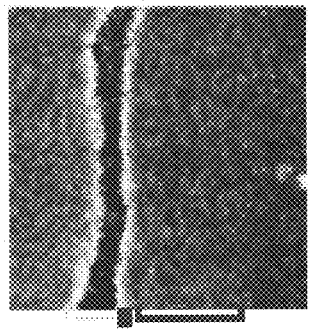
FIG. 4D M3
olfactory cilia
olfactory sensory neurons FIG. 5A  M3    Cy3    Phast contrast
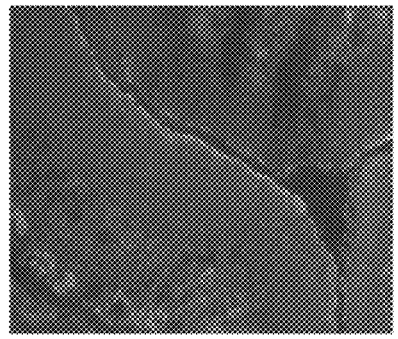 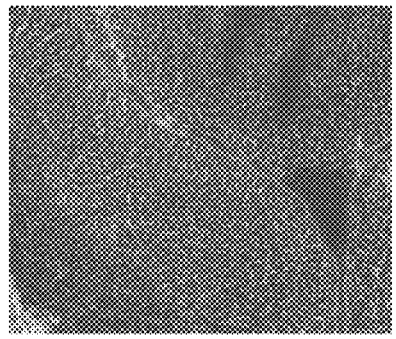
FIG. 5B  ACIII
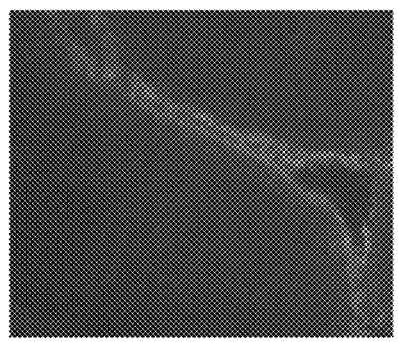 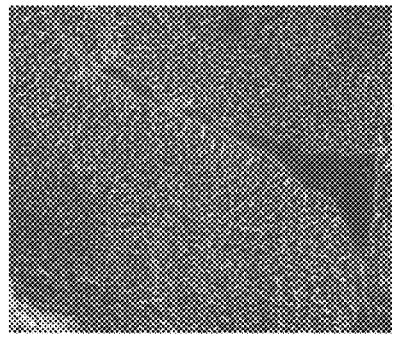
FIG. 5C  M2
 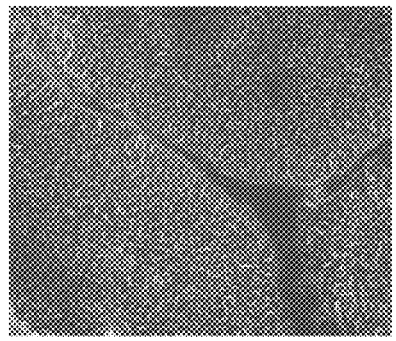

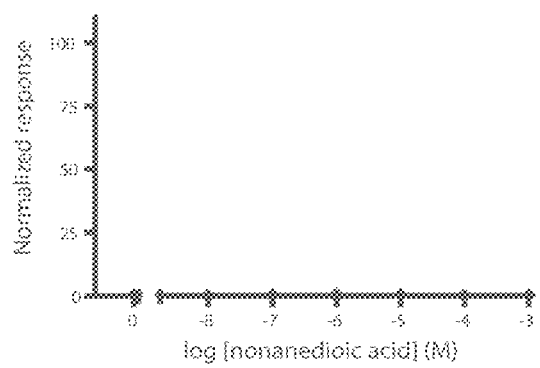
FIG. 8A M3 Only
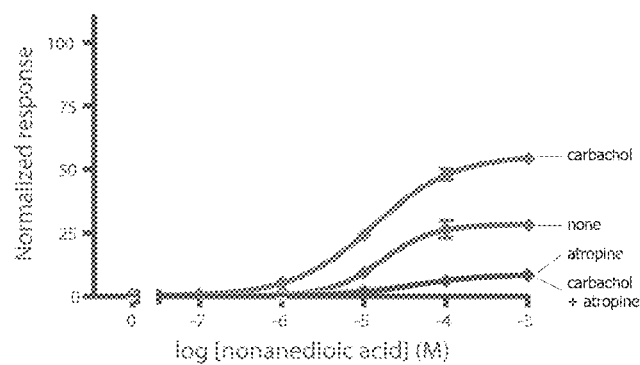
FIG. 8B M3 + OR

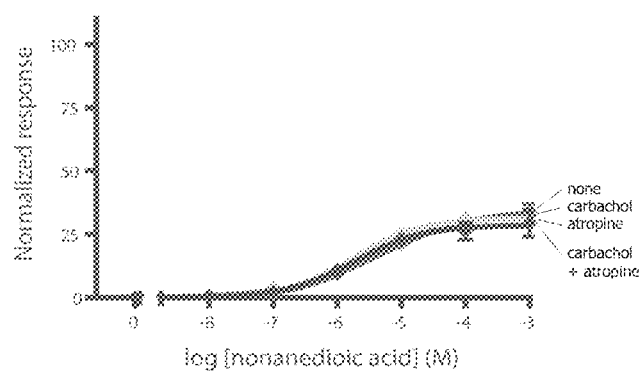
FIG. 8C OR + RTP1S
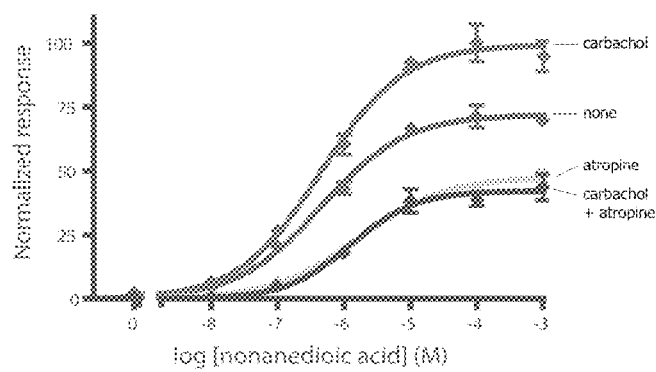
FIG. 8D M3 + OR + RTP1S

S6 + RTP1S + G15olf

M3

M3 + S6

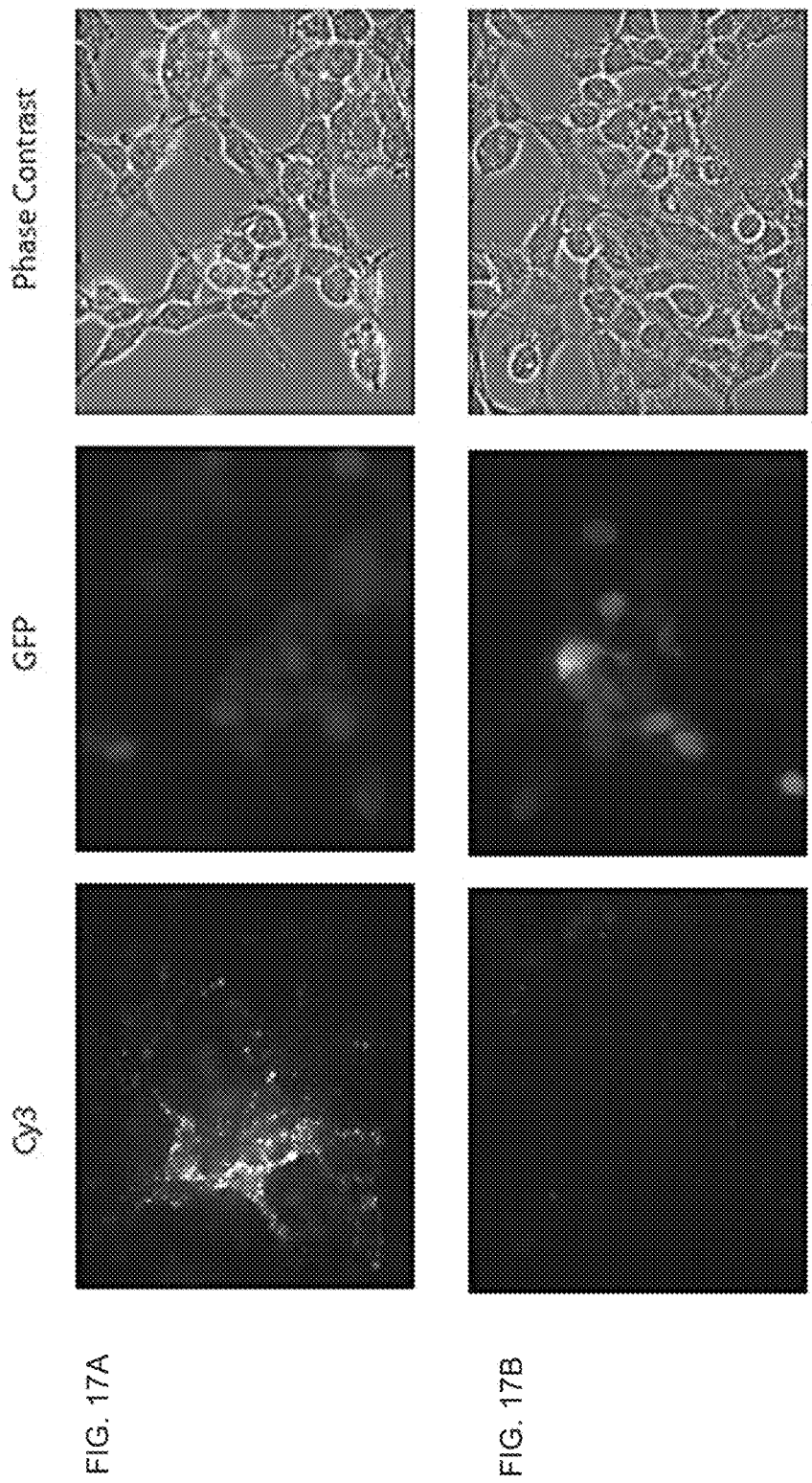

FIG. 21

ATGAACACCTCAGTGCCCCCTGCTGTCAGTCCCAACATCACCGTCTTGGCACCAGGAAAGGGTCCCTGGC
AAGTGGCATTCATCGGGATCACCACAGGCCTCCTGTCTCTGGCTACAGTGACAGGCAACCTGCTGGTGCT
CATCTCCTTCAAGGTCAACACAGAGCTCAAGACAGTCAACAACTACTTCCTGCTGAGCCTGGCCTGTGCT
GATCTCATCATTGGCACTTTCTCCATGAACCTCTATACCACATACCTGCTCATGGGCCACTGGGCTCTGG
GCACACTGGCCTGTGACCTCTGGCTGGCCCTGGACTATGTGGCCAGCAACGCCTCTGTCATGAATCTTCT
GCTCATCAGCTTTGACCGTTACTTCTCAGTGACCCGACCCCTGAGCTACCGAGCCAAGCGCACTCCCCGC
AGGGCAGCTCTGATGATTGGCCTCGCGTGGTTGGTTTCCTTCGTTCTCTGGGCCCCAGCCATCCTCTTCT
GGCAATACCTAGTTGGGGAGCGGACAGTGCTGGCTGGGCAGTGCTACATCCAGTTCCTCTCCCAACCCAT
CATCACTTTTGGCACAGCCATGGCCGCCTTCTACCTCCCTGTCACAGTCATGTGTACGCTGTACTGGCGC
ATCTACCGGGAGACAGAAAACCGAGCCCGGGAGCTAGCAGCCCTACAGGGCTCTGAGACACCAGGCAAAG
GTGGTGGCAGCAGCAGCAGCTCAGAGAGGTCACAGCCAGGAGCTGAAGGCTCACCCGAGTCACCTCCAGG
CCGCTGCTGTCGCTGTTGCCGGGCACCCAGACTTCTGCAGGCCTACAGCTGGAAAGAAGAAGAGGAAGAG
GATGAAGGCTCCATGGAGTCCCTCACATCCTCTGAAGGTGAGGAGCCTGGCTCAGAAGTGGTGATCAAGA
TGCCTATGGTAGATCCTGAGGCACAGGCACCCACCAAGCAGCCTCCCAAAAGCTCCCCAAATACAGTCAA
GAGGCCCACCAAGAAAGGCCGAGACCGAGGCGGCAAAGGCCAAAAACCCCGAGGGAAGGAACAACTGGCC
AAGAGAAAGACCTTCTCACTGGTCAAGGAGAAGAAGGCAGCTCGGACCCTGAGTGCCATCCTGCTGGCCT
TCATCCTCACCTGGACACCATATAACATCATGGTGCTGGTGTCTACATTCTGCAAGGACTGTGTTCCAGA
AACCCTATGGGAGCTGGGCTACTGGCTTTGCTACGTCAACAGCACTGTCAACCCCATGTGCTACGCACTC
TGCAACAAAGCCTTCCGGGACACTTTCCGCCTGCTGTTGCTCTGCCGCTGGGACAAGCGGCGCTGGCGCA
AAATCCCCAAGCGCCCTGGCTCTGTGCACCGCACCCCCTCCCGCCAATGCTAA 1 mntsvppavs pnitvlapgk gpwqvafigi ttgllslatv tgnllvIisf kvnteIktvn

FIG. 21 (cont'd)

```
 61 nyfllslaca dliigtfsmn lyttyllmgh walgtlacdl wlaldyvasn asvmnlllis
121 fdryfsvtrp lsyrakrtpr raalmiglaw lvsfvlwapa ilfwqylvge rtvlagqcyi
181 qflsqpiitf gtamaafylp vtvmctlywr iyretenrar elaalqgset pgkgggssss
241 sersqpgaeg spesppgrcc rccraprllq ayswkeeeee degsmeslts segeepgsev
301 vikmpmvdpe aqaptkqppk sspntvkrpt kkgrdrggkg qkprgkeqla krktfslvke
361 kkaartlsai llafiltwtp ynimvlvstf ckdcvpetlw elgywlcyvn stvnpmcyal
421 cnkafrdtfr llllcrwdkr rwrkipkrpg svhrtpsrqc
```

FIG. 22

ATGAATAACTCAACTAACTCCTCGAACAATGGTTTGGCTATTACCAGTCCTTACAAG
ACATTTGAAGTGG
TATTTATTGTCCTTGTGGCTGGATCCCTCAGTCTGGTGACCATCATTGGGAACATTCT
AGTCATGGTTTC
CATTAAAGTCAACCGCCACCTTCAGACTGTCAACAATTACTTCTTGTTCAGCCTGGC
CTGTGCTGACCTC
ATCATAGGTGTTTCTCCATGAACTTGTATACCCTCTACACTGTGATTGGCTACTGGC
CTTTGGGACCTG
TAGTGTGCGACCTTTGGCTAGCCTTGGACTATGTTGTCAGCAATGCCTCCGTTATGA
ATCTTCTCATCAT
CAGCTTTGATAGATACTTCTGTGTCACAAAACCTCTAACCTACCCAGTTAAGCGGAC
CACAAAAATGGCA
GGCATGATGATTGCAGCTGCGTGGGTTCTTTCCTTCATCCTCTGGGCCCCAGCCATTC
TCTTCTGGCAGT
TCATCGTAGGGGTAAGGACTGTGGAAGACGGGGAGTGCTACATTCAGTTCTTTTCCA
ACGCTGCCGTCAC
CTTTGGCACTGCCATTGCGGCTTTCTATCTGCCTGTCATCATCATGACTGTGCTCTAT
TGGCACATATCC
CGGGCGAGCAAGAGCAGAATAAAGAAAGAAAAGAAGGAACCAGTGGCCAACCAAG
ACCCGGTGTCTCCGA
GTCTAGTGCAAGGAAGAATTGTAAAGCCAAACAACAACAACATGCCTGGTGGTGAT
GGTGGCCTGGAGCA
CAACAAGATCCAGAATGGCAAGGCTCCGCGGGACGGTGGGACTGAAAACTGCGTTC
AGGGGGAGGAGAAA
GAAAGCTCCAACGACTCCACGTCTGTCAGTGCCGTGGCCTCCAACATGAGAGATGA
TGAGATAACCCAGG
ATGAAAACACGGTTTCCACTTCCCTGGGCCACTCCAAAGATGACAACTCTAGGCAG
ACATGCATCAAAAT
TGTCACCAAGACCCAAAAGGGTGACGCATGCACACCAACAAGTACCACAGTAGAAC
TAGTGGGATCGTCA
GGTCAGAATGGTGATGAAAAGCAGAACATTGTAGCCCGCAAAATTGTGAAGATGAC
CAAGCAGCCTGCCA
AAAAGAAGCCTCCTCCATCCCGGGAAAAGAAAGTGACCAGGACAATCTTGGCTATC
CTGTTGGCTTTCAT
CATCACGTGGGCGCCATACAATGTCATGGTGCTCATCAATACCTTCTGTGCACCCTG
CATCCCCAATACA
GTGTGGACAATTGGCTACTGGCTCTGTTACATTAATAGCACCATCAACCCTGCCTGC
TATGCACTTTGTA
ACGCCACCTTCAAAAAGACTTTTAAGCACCTCCTTATGTGTCATTACAAGAACATAG
GCGCTACAAGGTAA

M2
1 mnnstnsssm glaitspykt fevvfivlva gsislvtiig nilvmvsikv nrhlqtvmny

FIG. 22 (cont'd)

```
 61 flfslacadl iigvfsmnly tlytvigywp lgpvvcdlwl aldyvvsnas vmnlliisfd
121 ryfcvtkplt ypvkrttkma gmmiaaawvl sfilwapail fwqfivgvrt vedgecyiqf
181 fsnaavtfgt aiaafylpvi imtvlywhis rasksrikke kkepvanqdp vspslvqgri
241 vkpnnnnmpg gdgglehnki qngkaprdgg tencvqgeek essndstsvs avasnmrdde
301 itqdentvst slghskddns rqtcikivtk tqkgdactpt sttvelvgss gqngdekqni
361 varkivkmtk qpakkkppps rekkvtrtil aillafiitw apynvmvlin tfcapcipnt
421 vwtigywlcy instinpacy alcnatfkkt fkhllmchyk nigatr
```

FIG. 23

ATGACCTTGCACAGTAACAGTACAACCTCGCCTTTGTTTCCCAACATCAGCTCTTCCT
GGGTGCACAGTC
CCTCAGAGGCGGGGCTGCCCTTGGGGACAGTCTCTCAATTGGACAGCTACAACATTT
CCCAAACCTCTGG
GAATTTCTCCTCAAATGACACCTCCAGTGACCCTCTAGGGGGCCACACCATCTGGCA
AGTGGTCTTCATT
GCATTCTTGACTGGCTTCCTGGCATTGGTGACCATCATCGGCAACATCCTTGTCATTG
TGGCATTTAAGG
TCAACAAACAGCTGAAGACAGTCAACAACTACTTCCTCTTAAGCCTGGCCTGCGCAG
ATCTGATCATCGG
GGTCATTTCCATGAACCTGTTCACGACCTACATCATTATGAACCGCTGGGCTCTGGG
GAACTTAGCCTGT
GACCTCTGGCTTTCCATTGACTATGTGGCCAGCAATGCTTCTGTCATGAATCTGCTGG
TGATCAGCTTTG
ACAGGTACTTTTCTATTACCAGGCCACTCACTTACCGAGCCAAACGAACAACAAAAC
GAGCCGGTGTGAT
GATTGGTCTGGCTTGGGTCATCTCCTTTGTCCTGTGGGCTCCTGCCATCTTGTTCTGG
CAATACTTTGTA
GGGAAGAGAACTGTGCCCCCCGGAGAATGTTTCATTCAGTTTCTAAGTGAGCCCACC
ATCACCTTCGGCA
CGGCGATCGCTGCCTTTTACATGCCTGTCACCATCATGACTATTTTATACTGGAGAAT
CTATAAGGAGAC
TGAGAAACGTACCAAAGAGCTGGCTGGGCTACAGGCCTCTGGGACAGAAGCGGAAG
CAGAAAACTTTGTC
CACCCCACAGGCAGTTCTCGAAGCTGTAGCAGCTATGAGCTACAACAGCAAGGCAC
GAAACGGTCATCTA
GGAGGAAGTATGGTGGCTGTCACTTCTGGTTCACAACTAAGAGCTGGAAGCCCAGT
GCTGAGCAGATGGA
CCAAGACCACAGTAGCAGTGACAGTTGGAATAACAACGATGCTGCTGCCTCCCTGG
AAAACTCTGCTTCT
TCTGATGAAGAGGATATTGGCTCAGAGACCAGAGCCATCTATTCCATTGTACTCAAG
CTGCCGGGTCATA
GCACCATCCTCAACTCTACCAAGCTACCCTCCTCAGATAACCTGCAGGTGCCAGACA
AGGACCTGGGGAC
TATGGATGTAGAGAGAAATGCCCATAAGCTTCAGGCCCAGAAGAGTATGGATGACC
GTGACAACTGTCAG
AAGGACTTCTCCAAGCTCCCCATCCAGTTAGAGTCTGCCGTGGACACAGCCAAGACC
TCTGACACCAACT
CCTCGGTGGACAAGACCACGGCCGCTCTACCTCTGTCCTTCAAAGAAGCCACGCTGG
CTAAGAGGTTTGC
TCTCAAGACCAGAAGTCAGATCACCAAGCGGAAAAGGATGTCGCTCATCAAGGAGA
AGAAGGCCGCCCAG

FIG. 23 (cont'd)

ACACTCAGTGCCATCTTGCTGGCTTTCATCATCACGTGGACCCCCTACAACATCATG
GTCCTGGTGAACA
CCTTCTGTGACAGCTGCATACCCAAAACCTATTGGAATCTGGGCTACTGGCTGTGCT
ATATCAACAGCAC
CGTGAACCCCGTGTGCTATGCCCTGTGCAACAAGACATTCAGAACCACCTTCAAGAT
GCTTCTCTTATGC
CAGTGTGACAAGAGGAAGCGGCGCAAACAGCAGTACCAGCAGAGACAGTCCGTCA
TTTTTCACAAGCGAGTGCCTGAGCAGGCCTTGTAG

M3
    1 mtlhsnstts plfpnisssw vhspseaglp lgtvsqldsy nisqtsgnfs sndtssdplg
   61 ghtiwqvvfi afltgflalv tiignilviv afkvnkqlkt vnnyfllsla cadliigvis
  121 mnlfttyiim nrwalgnlac dlwlsidyva snasvmnllv isfdryfsit rpltyrakrt
  181 tkragvmigl awvisfvlwa pailfwqyfv gkrtvppgec fiqflsepti tfgtaiaafy
  241 mpvtimtily wriyketekr tkelaglqas gteaeaenfv hptgssrscs syelqqqgtk
  301 rssrrkyggc hfwfttkswk psaeqmdqdh sssdswnmd aaaslensas sdeedigset
  361 raiysivlkl pghstilnst klpssdnlqv pdkdlgtmdv ernahklqaq ksmddrdncq
  421 kdfsklpiql esavdtakts dtnssvdktt aalplsfkea tlakrfalkt rsqitkrkrm
  481 slikekkaaq tlsaillafi itwtpynimv lvntfcdsci pktywnlgyw lcyinstvnp
  541 vcyalcnktf rttfkmlllc qedkrkrrkq qyqqrqsvif hkrvpeqal

FIG. 24

ATGGCGAACTTCACACCTGTCAATGGCAGCTCAGCCAATCAGTCTGTGCGCCTGGTC
ACAACAGCCCACA
ACCACCTGGAGACAGTGGAGATGGTGTTCATTGCGACAGTGACTGGTTCCCTGAGCC
TGGTGACTGTGGT
GGGTAACATCCTGGTGATGCTGTCCATCAAGGTCAACAGGCAGTTGCAGACAGTCA
ACAACTACTTCCTG
TTCAGCCTGGCGTGTGCAGATCTCATCATAGGGGCGTTCTCTATGAACCTTTACACCT
TATACATCATCA
AGGGCTACTGGCCCCTGGGTGCCGTGGTCTGTGACCTGTGGCTGGCCCTGGACTATG
TGGTGAGCAATGC
CTCTGTCATGAACCTTCTCATCATCAGCTTTGACCGCTATTTCTGCGTCACCAAGCCC
CTCACCTATCCA
GCCCGCCGCACTACTAAGATGGCAGGCCTCATGATTGCAGCCGCCTGGGTCTTGTCC
TTTGTACTCTGGG
CCCCTGCCATCTTGTTCTGGCAGTTTGTGGTGGGCAAGAGGACAGTGCCTGATAACC
AGTGCTTCATCCA
GTTCTTGTCCAACCCGGCGGTGACCTTCGGCACAGCCATTGCTGCCTTCTACCTGCCT
GTGGTCATCATG
ACGGTGCTGTATATTCATATCTCGCTGGCCAGCCGCAGCCGTGTTCACAAGCATCGA
CCCGAGGGCCCCA
AGGAGAAGAAGGCCAAGACTCTGGCTTTCCTCAAGAGCCCTCTGATGAAGCCGAGC
ATTAAGAAACCTCC
ACCAGGGGGCGCTTCTCGAGAGGAACTGCGCAACGGGAAGCTAGAAGAGGCTCCTC
CGCCAGCCCTGCCC
CCGCCTCCACGCCCAGTGGCTGACAAGGACACTTCCAATGAGTCCAGCTCAGGCAG
TGCCACCCAGAACA
CCAAGGAACGGCCACCCACAGAGCTGTCCACCACAGAGGCCGCCACCACACCAGCG
CTGCCCGCTCCTAC
CCTGCAGCCACGAACCCTCAACCCAGCCTCCAAGTGGTCCAAGATCCAAATTGTGAC
AAAGCAGACAGGC
AGTGAATGTGTGACTGCCATCGAGATCGTACCTGCCACGCCAGCTGGTATGCGCCCA
GCAGCCAATGTGG
CCCGAAAGTTTGCCAGCATCGCTCGTAACCAGGTGCGCAAGAAGCGGCAGATGGCG
GCCCGGGAGCGCAA
AGTGACTCGGACAATCTTTGCCATTCTGCTGGCCTTCATCCTCACCTGGACACCCTAC
AATGTCATGGTC
CTGGTGAACACCTTTTGCCAGAGCTGTATCCCCGAAAGGGTGTGGTCCATCGGCTAC
TGGCTCTGCTACG
TCAACAGCACGATCAACCCTGCCTGCTATGCACTCTGCAATGCCACTTTCAAAAAGA
CCTTCCGGCACCT
TTTGCTGTGCCAGTATCGGAACATCGGCACAGCCAGGTAG

```
  1 manftpvngs sanqsvrlvt tahnhletve mvfiatvtgs lslvtvvgni lvmlsikvnr
 61 qlqtvnnyfl fslacadlii gafsmnlytl yiikgywplg avvcdlwlal dyvvsnasvm
121 nlliisfdry fcvtkpltyp arrttkmagl miaaawvlsf vlwapailfw qfvvgkrtvp
181 dnqcfiqfls npavtfgtai aafylpvvim tvlyihisla srsrvhkhrp egpkekkakt
241 laflkspImk psikkpppgg asreelrngk leeapppalp ppprpvadkd tsnesssgsa
301 tqntkerppt elstteaatt palpaptlqp rtlnpaskws kiqivtkqtg secvtaieiv
361 patpagmrpa anvarkfasi arnqvrkkrq maarerkvtr tifaillafi ltwtpynvmv
421 lvntfcqsci pervwsigyw lcyvnstinp acyalcnatf kktfrhlllc qyrnigtar
```

FIG. 25

ATGGAAGGGGAGTCTTATCACAATGAAACCACTGTCAACGGCACCCCAGTAAATCA
CCAGGCTTTGGAAC
GCCATGGACTGTGGGAAGTCATTACTATTGCAGCTGTGACCGCTGTGGTCAGTCTGA
TGACCATTGTCGG
CAATGTCTTGGTCATGATCTCCTTCAAAGTCAACAGTCAGCTCAAGACAGTTAACAA
CTATTACCTGCTC
AGCTTGGCCTGTGCAGACCTCATCATTGGCATCTTCTCCATGAACCTCTACACGACC
TACATCCTCATGG
GACGCTGGGTTCTCGGGAGTCTGGCCTGTGACCTTTGGCTTGCACTCGACTATGTAG
CCAGCAACGCTTC
TGTCATGAACCTTCTGGTGATTAGCTTTGATCGTTACTTTTCCATCACAAGACCACTG
ACATACCGAGCC
AAGCGTACCCCAAAGAGGGCTGGCATCATGATCGGCTTGGCATGGCTGGTCTCCTTC
ATCCTCTGGGCGC
CAGCCATCCTCTGCTGGCAGTACTTGGTCGGGAAGCGGACAGTACCACCTGATGAGT
GCCAGATCCAGTT
CCTCTCTGAGCCCACCATCACTTTTGGGACCGCCATTGCCGCTTTCTATATCCCTGTC
TCCGTCATGACC
ATACTCTACTGCCGGATCTACCGGGAAACAGAGAAACGAACCAAGGACCTGGCTGA
CCTCCAAGGTTCCG
ATTCTGTGGCAGAAGTCAAGAAGAGAAAACCGGCTCACAGGACCCTGCTCAGATCT
TTCTTTAGCTGCCC
TAGACCCAGCCTGGCCCAGAGAGTACGGAACCAGGCCTCCTGGTCATCCTCCCGTA
GAAGCACCTCAACA
ACGGGAAAGCCAACCCAGGCCACTGATCTAAGTGCTGACTGGGAAAAGGCTGAGCA
GGTTACCAACTGTA
GCAGCTGCCCCTCTTCAGAGGACGAAGCCAAGGCCACCACTGACCCTGTCTTTCAAG
TGGTCTGCAAGAA
TGAGGCCAAGGAAAGCCCGGGGAAGGAATTCAATACCCAAGAGACCAAGGAAACG
TTTGTGAGCCCTCGG
ACTGAAAACAATGACTATGACACTCCCAAGTACTTCCTGTCTCCAGGTGCTGCTCAC
AGACTCAAGAGTC
AGAAGTGTGTTGCCTATAAGTTCCGATTGGTGGTAAAAGCTGACGGGACCCAGGAG
ACAAACAATGGCTG
TCGTAAGGTGAAAATCATGCCCTGTTCCTTCCCAGTGTCCAAAGACCCTTCAACAAA
AGGCCTGGATCCC
CACCTCAGCCATCAAATGACCAAACGAAAGAGAATGGTCCTAGTCAAAGAGAGGAA
AGCGGCGCAGACCT
TGAGCGCCATTCTCCTGGCCTTCATCATCACATGGACTCCTTATAACATCATGGTCCT
GGTTTCCACCTT
CTGTGACAAGTGTGTCCCTGTCACCCTGTGGCACTTGGGTTACTGGCTGTGCTATGTC
AACAGCACCATC

FIG. 25 (cont'd)

AACCCCATCTGTTACGCTCTCTGCAACAGAACCTTCAGGAAGACCTTTAAGCTGCTG
CTTCTCTGCCGGT
GGAAAAGAAAAAGTAGAAGAGAAATTGTATTGGCAAGGCAACAGCAAGCTACC
CTGA

M5
```
  1 megesyhnet tvngtpvnhq alerhgiwev itiaavtavv slmtivgnvl vmisfkvnsq
 61 lktvnnyyll slacadliig ifsmnlytty ilmgrwvlgs lacdlwlald yvasnasvmn
121 llvisfdryf sitrpltyra krtpkragim iglawlvsfi lwapailcwq ylvgkrtvpp
181 decqiqflse ptitfgtaia afyipvsvmt ilycriyret ekrtkdladl qgsdsvaevk
241 krkpahrtll rsffscprps laqrvrnqas wsssrrstst tgkptqatdl sadwekaeqv
301 incsscpsse deakattdpv fqvvckneak espgkefntq etketfvspr tenndydtpk
361 yflspgaahr lksqkcvayk frlvvkadgt qetnngcrkv kimpcsfpvs kdpstkgldp
421 hlshqmtkrk rmvlvkerka aqtlsailla fiitwtpyni mvlvstfcdk cvpvtlwhlg
481 ywlcyvnsti npicyalcnr tfrktfklll lcrwkkkkve eklywqgnsk lp
```

FIG. 26

ATGTGTAAGAGTGTGACCACAGGTGAGTGGAAGAAGGTCTTCTACGAGAAGATGGAGGAGGTGAAGCCAG
CGGACAGCTGGGACTTCATCATAGACCCCAACCTCAAGCACAATGTGTTGGCCCCTGGCTGGAAGCAGTA
CCTGGAACTTCATGCCTCAGGCAGGTTCCACTGTTCCTGGTGCTGGCACACCTGGCAGTCACCCCATGTA
GTCATCCTCTTCCACATGTACCTGGACAAGGCTCAGCGCGCTGGTTCGGTGCGCATGCGTGTGTTCAAGC
AGCTCTGCTACGAGTGCGGTACAGCACGGCTGGATGAGTCCAGCATGCTGGAGGAGAACATCGAAAGCCT
GGTGGACAACCTCATCACCAGTTTGCGAGAGCAGTGCTACGGGGAGCGTGGTGGCCACTACCGCATCCAT
GTGGCCAGCCGGCAGGACAACCGGCGACACCGCGGAGAGTTCTGCGAGGCCTGCCAGGAAGGCATCGTGC
ACTGGAAGCCCAGTGAGAAGCTGCTGGAGGAGGAGGCGACCACCTACACCTTCTCCCGTGCTCCCAGCCC
CACCAAACCGCAGGCTGAAACAGGCTCAGGCTGCAACTTCTGCTCCATTCCCTGGTGCTTATTTTGGGCC
ACGGTTTTGATGCTCATCATCTACCTGCAATTCTCCTTCCGTACTTCTGTCTAA

COMPOSITIONS AND METHODS FOR ENHANCING ODORANT RECEPTOR ACTIVITY

CROSS-REFERENCE TO RELATED APPLICATIONS

The present application is a continuation of U.S. patent application Ser. No. 14/754,940, filed Jun. 30, 2015, allowed as U.S. Pat. No. 9,611,308, which is a continuation of U.S. patent application Ser. No. 13/513,600, filed Sep. 18, 2012, allowed as U.S. Pat. No. 9,068,226, which is a U.S. National Phase Entry of International Patent Application No. PCT/US2010/059093, international filing date Dec. 6, 2010, which claims priority to expired U.S. Provisional Application Ser. No. 61/266,805, filed Dec. 4, 2009, the contents of which are incorporated by reference in their entireties.

STATEMENT REGARDING FEDERALLY SPONSORED RESEARCH OR DEVELOPMENT

This invention was made in part with government support under Grant No. R01DC005782 awarded by the National Institutes of Health. The government has certain rights in the invention.

FIELD OF THE INVENTION

The present invention relates to polypeptides capable of modulating odorant receptor activation. In particular, the present invention provides polypeptides (e.g., type 3 muscarinic actetylcholine receptor M3) capable of enhancing odorant receptor activation. The present invention further provides assays for the detection of ligands specific for various odorant receptors. Additionally, the present invention provides methods of screening for polypeptide polymorphisms and mutations associated with odorant receptor activation (e.g., polymorphisms and mutations associated with muscarinic actetylcholine receptor polypeptides (e.g., M1, M2, M3, M4, M5)), as well as methods of screening for therapeutic agents, ligands, and modulators of such proteins.

BACKGROUND OF THE INVENTION

The olfactory system represents one of the oldest sensory modalities in the phylogenetic history of mammals. Olfaction is less developed in humans than in other mammals such as rodents. As a chemical sensor, the olfactory system detects food and influences social and sexual behavior. The specialized olfactory epithelial cells characterize the only group of neurons capable of regeneration. Activation occurs when odiferous molecules come in contact with specialized processes known as the olfactory vesicles. Within the nasal cavity, the turbinates or nasal conchae serve to direct the inspired air toward the olfactory epithelium in the upper posterior region. This area (only a few centimeters wide) contains more than 100 million olfactory receptor cells. These specialized epithelial cells give rise to the olfactory vesicles containing kinocilia, which serve as sites of stimulus transduction.

There are three specialized neural systems are present within the nasal cavities in humans: 1) the main olfactory system (cranial nerve I), 2) trigeminal somatosensory system (cranial nerve V), 3) the nervus terminalis (cranial nerve 0). CN I mediates odor sensation. It is responsible for determining flavors. CN V mediates somatosensory sensations, including burning, cooling, irritation, and tickling. CN 0 is a ganglionated neural plexus. It spans much of the nasal mucosa before coursing through the cribriform plate to enter the forebrain medial to the olfactory tract. The exact function of the nervus terminalis is unknown in humans.

The olfactory neuroepithelium is a pseudostratified columnar epithelium. The specialized olfactory epithelial cells are the only group of neurons capable of regeneration. The olfactory epithelium is situated in the superior aspect of each nostril, including cribriform plate, superior turbinate, superior septum, and sections of the middle turbinate. It harbors sensory receptors of the main olfactory system and some CN V free nerve endings. The olfactory epithelium loses its general homogeneity postnatally, and as early as the first few weeks of life metaplastic islands of respiratory-like epithelium appear. The metaplasia increases in extent throughout life. It is presumed that this process is the result of insults from the environment, such as viruses, bacteria, and toxins.

There are 6 distinct cells types in the olfactory neuroepithelium: 1) bipolar sensory receptor neurons, 2) microvillar cells, 3) supporting cells, 4) globose basal cells, 5) horizontal basal cells, 6) cells lining the Bowman's glands. There are approximately 6,000,000 bipolar neurons in the adult olfactory neuroepithelium. They are thin dendritic cells with rods containing cilia at one end and long central processes at the other end forming olfactory fila. The olfactory receptors are located on the ciliated dendritic ends. The unmyelinated axons coalesce into 40 bundles, termed olfactory fila, which are ensheathed by Schwann-like cells. The fila transverses the cribriform plate to enter the anterior cranial fossa and constitute CN I. Microvillar cells are near the surface of the neuroepithelium, but the exact functions of these cells are unknown. Supporting cells are also at the surface of the epithelium. They join tightly with neurons and microvillar cells. They also project microvilli into the mucus. Their functions include insulating receptor cells from one another, regulating the composition of the mucus, deactivating odorants, and protecting the epithelium from foreign agents. The basal cells are located near the basement membrane, and are the progenitor cells from which the other cell types arise. The Bowman's glands are a major source of mucus within the region of the olfactory epithelium.

The odorant receptors are located on the cilia of the receptor cells. Each receptor cell expresses a single odorant receptor gene. There are approximately 1,000 classes of receptors at present. The olfactory receptors are linked to the stimulatory guanine nucleotide binding protein Golf. When stimulated, it can activate adenylate cyclase to produce the second messenger cAMP, and subsequent events lead to depolarization of the cell membrane and signal propagation. Although each receptor cell only expresses one type of receptor, each cell is electrophysiologically responsive to a wide but circumscribed range of stimuli. This implies that a single receptor accepts a range of molecular entities.

The olfactory bulb is located on top of the cribriform plate at the base of the frontal lobe in the anterior cranial fossa. It receives thousands of primary axons from olfactory receptor neurons. Within the olfactory bulb, these axons synapse with a much smaller number of second order neurons which form the olfactory tract and project to olfactory cortex. The olfactory cortex includes the frontal and temporal lobes, thalamus, and hypothalamus.

Although mammalian ORs were identified over 10 years ago, little is known about the selectivity of the different ORs for chemical stimuli, mainly because it has been difficult to express ORs on the cell surface of heterologous cells and assay their ligand-binding specificity (see, e.g., Mombaerts, P. (2004) Nat Rev Neurosci 5, 263-278; herein incorporated by reference in its entirety). The reason is that OR proteins are retained in the ER and subsequently degraded in the proteosome (see, e.g., Lu, M., et al., (2003) Traffic 4, 416-433; McClintock, T. S., (1997) Brain Res Mol Brain Res 48, 270-278; each herein incorporated by reference in their entireties). Despite these difficulties, extensive efforts have matched about 20 ORs with cognate ligands with various degrees of certainty (see, e.g., Bozza, T., et al., (2002) J Neurosci 22, 3033-3043; Gaillard, I., et al., (2002) Eur J Neurosci 15, 409-418; Hatt, H., et al., (1999) Cell Mol Biol 45, 285-291; Kajiya, K., et al., (2001) J Neurosci 21, 6018-6025; Krautwurst, D., et al., (1998) Cell 95, 917-926; Malnic, B., et al., (1999) Cell 96, 713-723; Raming, K., et al., (1993) Nature 361, 353-356; Spehr, M., et al., (2003) Science 299, 2054-2058; Touhara, K., et al., (1999) Proc Natl Acad Sci USA 96, 4040-4045; Zhao, H., et al., (1998) Science 279, 237-242; each herein incorporated by reference in their entirety). Adding the 20 N-terminal amino acids of rhodopsin (e.g., Rho-tag) or a foreign signal peptide to the N-terminus facilitates surface expression of some ORs in heterologous cells (see, e.g., Hatt, H., et al., (1999) Cell Mol Biol 45, 285-291; Krautwurst, D., et al., (1998) Cell 95, 917-926; each herein incorporated in their entirety). However, for most ORs, modifications do not reliably promote cell-surface expression. For example, ODR-4, which is required for proper localization of chemosensory receptors in C. elegans, has a small effect on facilitating cell-surface expression of one rat OR, but not another OR (see, e.g., Gimelbrant, A. A., et al., (2001) J Biol Chem 276, 7285-7290; herein incorporated by reference). These findings indicate that olfactory neurons have a selective molecular machinery that promotes proper targeting of OR proteins to the cell surface, but no components of this machinery have been identified (see, e.g., Gimelbrant, A. A., et al., (2001) J Biol Chem 276, 7285-7290; McClintock, T. S., and Sammeta, N. (2003) Neuroreport 14, 1547-1552; each herein incorporated by reference in their entirety).

What is needed is a better understanding of olfactory sensation. What is further needed is a better understanding of odorant receptor function.

SUMMARY OF THE INVENTION

A diverse repertoire of G-protein coupled receptors (GPCRs) allows cells to sense their environment. Mammalian olfaction requires the activation of odorant receptors (ORs), the largest family of GPCRs, but whether a broad range of ORs exhibit functional interactions with non-OR GPCRs is unclear. In experiments conducted during the course of developing embodiments for the present invention, it was demonstrated that the interaction of ORs with the type 3 muscarinic acetylcholine receptor M3, which is coexpressed with ORs in olfactory sensory neurons (OSNs), is important for the response of ORs to cognate odor ligands. For example, it was shown that in HEK293T cells, ORs and M3 can be coprecipitated, and coexpression of M3 increases the potency and efficacy of odor-elicited responses of a broad range of ORs. In addition, by monitoring the odor response of acutely dissociated mice OSNs, odor-dependent activation of OSNs is attenuated by M3-selective antagonists was demonstrated. In parallel, it was shown that when M3 is coexpressed, OR activation can be further enhanced by muscarinic agonists and inhibited by muscarinic antagonists in HEK293T cells. Furthermore, it was shown that M3-dependent potentiation of OR signaling is synergistic with that of RTP1S, an accessory factor required for efficient OR membrane-targeting. However, coexpression of M3 does not seem to enhance the cell-surface expression of ORs, suggesting that M3 acts through mechanism independent of RTP1, for example, by enhancing (e.g., promoting) the response of ORs already at the cell surface. Finally, OR activation by cognate odors transactivates M3 in the absence of M3 agonist. The crosstalk between ORs and M3 suggests, for example, that the functional coupling of ORs and M3 is important for robust OR activation.

Accordingly, the present invention relates to polypeptides capable of modulating odorant receptor activation. In particular, the present invention provides polypeptides (e.g., type 3 muscarinic actetylcholine receptor M3) capable of enhancing odorant receptor activation. The present invention further provides assays for the detection of ligands specific for various odorant receptors. Additionally, the present invention provides methods of screening for polypeptide polymorphisms and mutations associated with odorant receptor activation (e.g., polymorphisms and mutations associated with muscarinic actetylcholine receptor polypeptides (e.g., M1, M2, M3, M4, M5)), as well as methods of screening for therapeutic agents, ligands, and modulators of such proteins.

In certain embodiments, the present invention provides cell lines expressing an odorant receptor, wherein the expression is localized to the cell surface, wherein the cell line comprises a heterologous gene having at least 80% nucleic acid sequence similarity to SEQ ID NOS: 1, 2, 3, 4, or 5, wherein the heterologous gene encodes a Muscarinic Acetylcholine Receptor polypeptide (e.g., M1, M2, M3, M4, M5). In some embodiments, the odorant receptor is a human odorant receptor, a murine odorant receptor or a synthetic odorant receptor. In some embodiments, the cell line further comprises a gene having at least 80% nucleic acid similarlity to SEQ ID NO: 6, wherein the heterologous gene encodes an RTP1S polypeptide.

In certain embodiments, the present invention provides methods for identifying an odorant receptor ligand, comprising providing a cell comprising an odorant receptor, wherein the cell further comprises a heterologous nucleic acid encoding a polypeptide comprising an amino acid sequence that is at least 80% identical to SEQ ID No. 3, wherein the polypeptide is capable of promoting odorant receptor activity and at least one test compound; exposing the test compound to the cell; and detecting the activity of the odorant receptor.

In some embodiments, the cell further expresses a polypeptide known to assist in cell surface localization of odorant receptors (e.g., REEP polypeptides, RTP polypeptides (see, e.g., U.S. Pat. Nos. 7,425,445, 7,838,288, 7,691, 592; U.S. Patent Application Publication Nos. 2010/0222561, 2009/0124003, 2009/0092997; each herein incorporated by reference in its entirety). In some embodiments, the polypeptide known to assist in cell surface localization of odorant receptors is any variant or wild type form of REEP and/or RTP. In some embodiments the polypeptide known to assist in cell surface localization of odorant receptors is any variant or wild type form of RTP1. In some embodiments the polypeptide known to assist in cell surface localization of odorant receptors is an RTP polypeptide.

In some embodiments, the at least one test compound comprises more than one test compound. In some embodiments, the detecting comprises detecting a reporting agent. In some embodiments, the odorant receptor is a human odorant receptor, a murine odorant receptor or a synthetic odorant receptor. In some embodiments, the test compound is an odoriferous molecule. In some embodiments, the at least one test compound is exposed in the presence of a reference compound previously identified as a ligand for the odorant receptor. In some embodiments, the at least one test compound corresponds to a mixture of different test compounds. In some embodiments, the methods further comprise detecting the presence or absence of an odorant receptor ligand based upon the activity. In some embodiments, the exposing the test compound to the cell occurs in a setting selected from the group consisting of an in vitro setting, an in vivo setting, an in vitro setting, and an ex vivo setting.

In certain embodiments, the present invention provides methods for identifying an odorant receptor ligand, comprising providing a cell comprising an odorant receptor, wherein the cell further comprises a polypeptide comprising an amino acid sequence that is at least 80% identical to SEQ ID No. 9, wherein the polypeptide is capable of promoting odorant receptor activity and at least one test compound; exposing the test compound to the cell; and detecting the activity of the odorant receptor.

In some embodiments, the cell further expresses a polypeptide known to assist in cell surface localization of odorant receptors (e.g., REEP polypeptides, RTP polypeptides (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety). In some embodiments, the polypeptide known to assist in cell surface localization of odorant receptors is any variant or wild type form of REEP and/or RTP. In some embodiments the polypeptide known to assist in cell surface localization of odorant receptors is any variant or wild type form of RTP1. In some embodiments the polypeptide known to assist in cell surface localization of odorant receptors is an RTP1S polypeptide.

In some embodiments, the at least one test compound comprises more than one test compound. In some embodiments, the detecting comprises detecting a reporting agent. In some embodiments, the odorant receptor is a human odorant receptor, a murine odorant receptor or a synthetic odorant receptor. In some embodiments, the test compound is an odoriferous molecule. In some embodiments, the at least one test compound is exposed in the presence of a reference compound previously identified as a ligand for the odorant receptor. In some embodiments, the at least one test compound corresponds to a mixture of different test compounds. In some embodiments, the methods further comprise detecting the presence or absence of an odorant receptor ligand based upon the activity. In some embodiments, the exposing the test compound to the cell occurs in a setting selected from the group consisting of an in vitro setting, an in vivo setting, an in vitro setting, and an ex vivo setting.

In certain embodiments, the present invention provides methods for enhancing olfactory activity (e.g., odorant receptor activity) in a subject comprising administering to a subject a composition configured to increase (e.g., enhance) M3 activity. In some embodiments, the composition is configured to increase M3 expression. In some embodiments, the subject is a human being. In some embodiments, the subject is suffering from an olfactory disorder (e.g., anosmia, hyposmia, dysomia, phantosmia, hyperosmia, olfactory agnosia, upper respiratory infections, tumors of the anterior cranial fossa, and Kallmann syndrome, Foster Kennedy syndrome, Parkinson's disease, Alzheimer's disease, Huntington chorea). In some embodiments, the methods further comprise administering to the subject a composition comprising an M3 agonist. Examples of M3 agonists include, but are not limited to, acetylcholine, bethanechol, carbachol, oxotremorine, and pilocarpine.

In certain embodiments, the present invention provides methods for inhibiting olfactory activity (e.g., odorant receptor activity) in a subject comprising administering to a subject a composition configured to inhibit M3 activity. In some embodiments, the composition is configured to inhibit and/or prevent M3 expression. In some embodiments, the composition configured to inhibit M3 activity is an M3 antagonist. Examples of M3 antagonists include, but are not limited to, atropine, dicycloverine, tolterodine, oxybutynin, ipratropium, darifenacin, and titropium. In some embodiments, the subject is a human being.

In certain embodiments, the present invention provides methods for inhibiting olfactory activity (e.g., odorant receptor activity) in a subject comprising administering to a subject a composition configured to enhance M2 and/or M4 activity. In some embodiments, the composition is configured to inhibit and/or prevent M2 and/or M4 expression. In some embodiments, the subject is a human being. In some embodiments, the composition comprises an M2 and/or M4 agonist. Examples of M4 agonists include, but are not limited to, cetylcholine, carbachol, oxotremorine, LY-2033298, VU-0152100, VU-0152099 (see, e.g., Chan W Y, et al (2008) PNAS 105 (31); Brady A E, et al. (2008) J. Pharmacol. Exp. Ther. 327 (3): 941-53; each herein incorporated by reference in its entirety). Examples of M2 agonists include, but are not limited to, bethanechol and (2S,2'R,3'S,5'R)-1-methyl-2-(2-methyl-1,3-oxathiolan-5-yl)pyrrolidine 3-sulfoxide methyl iodide (selective for M2 but only partial agonist) (see, e.g., Scapecchi S, et al., J. Med. Chem. 49 (6): 1925-31; herein incorporated by reference in its entirety).

In certain embodiments, the present invention provides a method for identifying an odorant receptor ligand, comprising the steps of a) providing i) a cell line or cell membranes thereof comprising an odorant receptor and a reporting agent, and ii) a test compound; b) exposing the test compound to the cell line; and c) measuring the activity of the reporting agent. In some embodiments, the cell line expresses M1, M2, M3, M4, and/or M5. In some embodiments, the cell line expresses M3. In some embodiments, the cell line expresses a polypeptide known to assist in cell surface localization of odorant receptors (e.g., REEP polypeptides, RTP polypeptides (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety). In some embodiments, the polypeptide known to assist in cell surface localization of odorant receptors is any variant or wild type form of REEP and/or RTP. In some embodiments the polypeptide known to assist in cell surface localization of odorant receptors is any variant or wild type form of RTP1. In some embodiments the polypeptide known to assist in cell surface localization of odorant receptors is an RTP1S polypeptide. In some embodiments, the cell line is a heterologous cell line or a natural cell line. In some embodiments, the cell line is a 293T cell line. In some embodiments, the odorant receptor is a human odorant receptor. In some embodiments, the test compound is an odiferous molecule. In even further embodiments, the reporting agent is regulated by a cAMP responsive element. In some embodiments, the cell line further comprises $G_{\alpha olf}$. In other embodiments, the odorant receptor is a murine odorant receptor. In other embodiments, the odorant receptor is a synthetic odorant receptor. In some embodiments, the odorant receptor may be selected from, for example, OR-S6, Olfr62, S6/79, S18, S46, S50, MOR23-1, MOR31-4, MOR31-6, MOR32-5 and/or MOR32-11. In other embodiments, the reporting agent is an illuminating agent. In some embodiments, the illuminating agent is luciferase. In some embodiments, the method further comprises the step of detecting the presence or absence of an odorant receptor ligand based upon the reporting agent activity.

In some embodiments, the present invention provides a cell line coexpressing an odorant receptor, wherein the expression is localized to the cell surface, and a heterologous gene. In some embodiments, the heterologous gene comprises one or more of M1, M2, M3, M4, M5. In some embodiments, the heterologous gene is M3. In some embodiments, the cell line expresses a polypeptide known to assist in cell surface localization of odorant receptors (e.g., REEP polypeptides, RTP polypeptides (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety). In some embodiments, the polypeptide known to assist in cell surface localization of odorant receptors is any variant or wild type form of REEP and/or RTP. In some embodiments the polypeptide known to assist in cell surface localization of odorant receptors is any variant or wild type form of RTP1. In some embodiments the polypeptide known to assist in cell surface localization of odorant receptors is an RTP1S polypeptide. In some embodiments, the cell line is a 293T cell line. In some embodiments, the odorant receptor is a human odorant receptor. In some embodiments, the odorant receptor is tagged with a reporting agent. In some embodiments, the reporting agent is an illuminating reporting agent. In some embodiments, the illuminating reporting agent comprises glutathione-S-transferase (GST), c-myc, 6-histidine (6X-His), green fluorescent protein (GFP), maltose binding protein (MBP), influenza A virus haemagglutinin (HA), β-galactosidase, or GAL4. In some embodiments, the cell line further comprises $G_{\alpha olf}$ expression. In some embodiments, the odorant receptor is a murine, human or synthetic odorant receptor. In some embodiments, the odorant receptor comprises OR-S6, Olfr62, S6/79, S18, S46, S50, MOR23-1, MOR31-4, MOR31-6, MOR32-5 and MOR32-11.

The present invention further provides an isolated nucleic acid comprising a sequence encoding a protein comprising SEQ ID NOs: 1-5, and variants thereof that are at least 80% identical to SEQ ID NOs: 1-5. In some embodiments, the sequence is operably linked to a heterologous promoter. In some embodiments, the sequence is contained within a vector. In some embodiments, the vector is within a host cell.

The present invention also provides isolated and purified nucleic acid sequences that hybridize under conditions of high stringency to a nucleic acid comprising SEQ ID NOs: 1, 2, 3, 4, and/or 5. In some embodiments, the sequence is operably linked to a heterologous promoter. In some embodiments, the sequence is contained within a vector. In some embodiments, the host vector is within a host cell. In further some embodiments, the host vector is expressed in a host cell. In some embodiments, the host cell is located in an organism, wherein the organism is a non-human animal. In some embodiments, the present invention provides a polynucleotide sequence comprising at least fifteen (e.g., 15, 18, 20, 21, 25, 50, 100, 1000, . . . ) nucleotides capable of hybridizing under stringent conditions to the isolated nucleotide sequence.

In some embodiments, the present invention provides a polypeptide encoded by a nucleic acid selected from the group consisting of SEQ ID NOs: 1-5 and variants thereof that are at least 80% identical to SEQ ID NOs: 1-5. In further embodiments, the protein is at least 90% identical to SEQ ID NOs: 1-5. In even further embodiments, the protein is at least 95% identical to SEQ ID NOs: 1-5.

In some embodiments, the present invention provides a composition comprising a nucleic acid that inhibits the binding of at least a portion of a nucleic acid selected from the group consisting of SEQ ID NOs: 1-5 to their complementary sequences.

In some embodiments, the present invention provides a method for detection of a variant muscarinic acetylcholine receptor (e.g., M1, M2, M3, M4, M5) polypeptide in a subject, comprising providing a biological sample from a subject, wherein the biological sample comprises a muscarinic acetylcholine receptor (e.g., M1, M2, M3, M4, M5) polypeptide; and detecting the presence or absence of a variant muscarinic acetylcholine receptor (e.g., M1, M2, M3, M4, M5) polypeptide in the biological sample. In some embodiments, the biological sample is selected from the group consisting of a blood sample, a tissue sample, a urine sample, and an amniotic fluid sample. In further embodiments, the subject is selected from the group consisting of an embryo, a fetus, a newborn animal, and a young animal. In further embodiments, the animal is a human. In some embodiments, the detecting comprises differential antibody binding. In further embodiments, the detection comprises a Western blot.

In some embodiments, the present invention provides a kit comprising a reagent for detecting the presence or absence of a variant muscarinic acetylcholine receptor (e.g., M1, M2, M3, M4, M5) polypeptide in a biological sample. In some embodiments, the kit further comprises instruction for using the kit for the detecting the presence or absence of a variant muscarinic acetylcholine receptor (e.g., M1, M2, M3, M4, M5) polypeptide in a biological sample. In some embodiments, the instructions comprise instructions required by the U.S. Food and Drug Agency for in vitro diagnostic kits. In some embodiments, the reagent is one or more antibodies. In some embodiments, the biological sample is selected from the group consisting of a blood sample, a tissue sample, a urine sample, and an amniotic fluid sample. In some embodiments, the reagents are configured to detect a muscarinic acetylcholine receptor (e.g., M1, M2, M3, M4, M5) nucleic acid sequence.

In some embodiments, the present invention provides a method for screening compounds, comprising providing a sample expressing a heterologous muscarinic acetylcholine receptor (e.g., M1, M2, M3, M4, M5) polypeptide and a test compound; and exposing the sample to the test compound and detecting a biological effect. In some embodiments, the sample comprises a cell. In some embodiments, the sample comprises a tissue. In some embodiments, the sample is found in a subject. In some embodiments, the biological effect comprises a change in activity of muscarinic acetylcholine receptor (e.g., M1, M2, M3, M4, M5). In some embodiments, the biological effect comprises a change in expression of muscarinic acetylcholine receptor (e.g., M1, M2, M3, M4, M5).

In certain embodiments, the present invention provides methods for enhancing the activation of an odorant receptor in an olfactory sensory neuron of a patient comprising, consisting of, or consisting essentially of co-expressing a non-OR GPCR and odorant receptor in the neuron.

In certain embodiments, the present invention provides methods of treating an olfactory condition in a patient comprising, consisting of, or consisting essentially of coexpressing in at least one olfactory sensory neuron of the patient a non-OR GPCR and odorant receptor.

In certain embodiments, the present invention provides methods of treating a behavioral condition in a patient, wherein the behavioral condition is associated with olfactory receptor dysfunction, comprising, consisting of, or consisting essentially of, co-expressing in at least one olfactory sensory neuron a non-OR GPCR and odorant receptor.

In certain embodiments, the present invention provides methods for enhancing the expression, trafficking or signal transduction of an odorant receptor in a heterologous cell system comprising, consisting of, or consisting essentially of co-expressing in the cells a non-OR GPCR and an odorant receptor.

In certain embodiments, the present invention provides methods for screening novel receptors in a heterologous cell system comprising, consisting of, or consisting essentially of contacting said cells with a ligand of interest, wherein the cell co-expresses a non-OR GPCR and an odorant receptor; and measuring the activity of said odorant receptor.

In certain embodiments, the non-OR GPCR is a muscarinic receptor. In other embodiments, the non-OR GPCR is selected from the group consisting of muscarinic receptors M1, M2, M3, M4, M5 and combinations thereof. In some embodiments, the non-OR GPCR comprises muscarinic M3 receptor.

In other embodiments, the patient is a mammal. In preferred embodiments, the patient is a human.

These and other novel features and advantages of the disclosure will be fully understood from the following detailed description and the accompanying drawings.

BRIEF DESCRIPTION OF THE DRAWINGS

FIGS. 1A-F show that coexpression of M3 increases OR activation. To determine whether the expression of GPCRs affect the function of ORs, each of the GPCRs were coexpressed with one of three untagged (FIGS. 1A, 1B and 1C) or N-terminal rhodopsin tagged (Rho-tagged) (FIG. 1D, 1E, 1F) ORs: OR-S6 (FIG. 1A and FIG. 1D), OR-EG (FIGS. 1B and 1E), and Olfr62 (FIG. 1C and FIG. 1F), in HEK293T cells in the presence of OR-trafficking proteins RTP1S and an olfactory GTP/GDP exchange factor Ric-8b. These OR-expressing cells were then stimulated with cognate odors and the activation of the ORs measured using a cAMP-response element (CRE)-based luciferase reporter system that quantifies OR activation based on cAMP production. Of the 22 GPCRs that were cloned and tested (see Table 1), coexpression of a number of these GPCRs increased OR response upon odor stimulation in each of the three receptors tested (T-test, $p<0.05$ after Bonferroni correction) (FIGS. 1A-1F). Of these, only the type 3 muscarinic acetylcholine receptor (M3) consistently increased the response of all untagged (FIGS. 1A-C) and tagged (FIGS. 1D-F) receptors tested.

FIGS. 2A-C show that coexpression of M3 increases untagged OR activation in Hana3A cells. The 22 GPCRs were cotransfected as described in FIG. 1, except in Hana3A cells. The data showed that while in general a greater response was elicited (as expected for the Hana3A cell line), M3 was the only candidate to significantly potentiate OR activation in all three untagged ORs.

FIGS. 3A-C show that the muscarinic acetylcholine receptor family members modulate OR signaling. Although M3 most potently potentiates OR signaling and is the only receptor to do so for a broad range of ORs, other Gq-coupled (odd-numbered) muscarinic family members can also potentiate OR signaling. In contrast, the Gi-coupled (even-numbered) muscarinic receptors appear to inhibit the activation of: FIG. 3A OR S6; FIG. 3B OR-EG; FIG. 3C Olfr62.

FIGS. 4A-G demonstrate that M3 mRNA is expressed in the olfactory sensory neurons and that M3 protein is localized to the cilia of the olfactory epithelium. FIG. 4A, B, C: In situ hybridization analysis in the olfactory epithelium, demonstrating that M3 is strongly expressed by the olfactory neurons. OMP (olfactory marker protein) is a marker for mature olfactory sensory neurons. IL8RB is a control GPCR probe that does not hybridize to the OSNs. FIGS. 4D, E, F, G: Immunostaining using anti-muscarinic receptor antibodies for M1, M3, and M5. M3 is strongly expressed at the cilia of the olfactory epithelium in contrast to M1 and M5, which do not show expression at the cilia. Adenylyl Cyclase (ACIII) was used as a positive control.

FIGS. 5A-C show that the Muscarinic Receptor M2 is not expressed in the olfactory cilia. Immunostaining using anti-muscarinic receptor antibodies for M3 and M2. FIG. 5A shows M3 is strongly expressed in the olfactory cilia in contrast to M2 (FIG. 5C) which do not show expression at the cilia. Adenylyl Cyclase (ACIII) was used as a positive control. These results suggest, for example, that in contrast to M3, M2 does not play a significant function in vivo.

FIGS. 8A-D show that potentiation of ORs by M3 is enhanced by muscarinic agonists, but inhibited by muscarinic antagonists. Dose response curves of luciferase assays performed in HEK293T cells expressing FIG. 8A: M3 only; FIG. 8B: Rho-tagged OR-S6 and M3; FIG. 8C: Rho-tagged OR-S6 and RTP; and FIG. 8D: Rho-tagged OR-S6, mRTP, and M3 in the presence of muscarinic agonist $10^{-7}$M carbachol, muscarinic antagonist $10^{-6}$M atropine, and $10^{-7}$M carbachol and $10^{-6}$M atropine. Note that M3-specific agonist cevimeline had similar effect as carbachol and M3-specific antagonist had a similar, dose dependent effect on OR activation. Error bars indicated+/−SEM and assays were completed in triplicate.

FIG. 9A: Kinetics of Fluo-4/Fura-red ratio changes for a representative OSN stimulated by a mix of 10 odorants each at $10^{-5}$M with or without darifenecin. FIG. 9B: $10^{-7}$M darifenecin attenuated odor-mediated responses of OSNs. (paired T-test, N=36, 18, 18, respectively). FIG. 9C: Kinetics of Fluo-4/Fura-red ratio changes for a representative OSN stimulated by odor mix with or without pfHHSiD. FIG. 9D: $10^{-6}$M pfHHSiD attenuated odor-mediated responses of OSNs. (paired T-test, N=34, 15, 19, respectively).

FIG. 10B: two point analysis of net response area ($A_{net}$) comparing the responses to either antagonist+odor and odor alone.

FIG. 12A: untagged OR-S6, FIG. 12B: untagged Olfr62, FIG. 12C: Rho-tagged OR-S6, and FIG. 12D: Rho-tagged Olfr62. Error bars indicated+/−SEM and assays were completed in triplicate.

FIG. 13A: Rho-tagged OR-S6 with M3, FIG. 13B: Rho-tagged OR-S6 without M3, FIG. 13C: Rho-tagged Olfr62, with M3 and FIG. 13D: Rho-tagged Olfr62 without M3. Error bars indicated+/−SEM and assays were completed in triplicate.

FIG. 16A: nonandioic acid OR-S6 coupling to the promiscuous $G_{15olf}$ allow odorant activation to increase cellular calcium. FIG. 16B: calcium influx when cells expressing M3 are treated by $10^{-7}$M carbachol. FIG. 16C: Treating cells expressing both S6 and M3 (in the absence of RTP) with nonandioic acid does not elicit a calcium response triggered by carbachol. FIG. 16D: In the absence of M3, treating OR+RTP generates no calcium response. FIG. 16E: calcium level increases in cells co-expressing OR-S6, mRTP and M3 in the presence of $10^{-4}$M nonandioic acid along, similar to the response elicited by $10^{-7}$M carbachol. FIG. 16F: calcium release is blocked when nonandioic acid and $10^{-6}$M atropine are simultaneously used to stimulate cells expressing S6, mRTP, and M3. Data shown here were taken from one experiment; experimental results were replicated 3 times.

FIGS. 17A-B show Flag-OR S6, when coexpressed with M3 and RTP1S, is expressed at the cell surface. To ensure that Flag-OR S6 is also present at the cell surface and therefore will interact with M3 localized to the cell surface, Flag-specific antibodies were used to detect ORs at the surface of HEK293T cells when M3 and RTP1S are cotransfected (FIG. 17A). In marked contrast, when RTP1S and M3 are not coexpressed, Flag-S6 was very poorly expressed (FIG. 17B).

(FIG. 19B column 3). No co-precipitation was detected when Flag-tagged CD28, a negative control, was used (FIG. 19B column 4). Likewise, when the cell extract with anti-Flag antibodies was precipitated, HA-M3 was detected (FIG. 19C column 5). When Flag-OR-S6 was coexpressed with various HA-tagged GPCRs, OR-S6 and HA-M2 or HA-M3 were co-precipitated. But other GPCRs were not co-precipitated (FIG. 19F).

FIG. 21 shows the nucleic acid (mRNA) sequence (SEQ ID NO: 1) and amino acid sequence (SEQ ID NO: 7) for type 1 Muscarinic Acetylcholine Receptor (M1).

FIG. 22 shows the nucleic acid (mRNA) sequence (SEQ ID NO: 2) and amino acid sequence (SEQ ID NO: 8) for type 2 Muscarinic Acetylcholine Receptor (M2).

FIG. 23 shows the nucleic acid (mRNA) sequence (SEQ ID NO: 3) and amino acid sequence (SEQ ID NO: 9) for type 3 Muscarinic Acetylcholine Receptor (M3).

FIG. 24 shows the nucleic acid (mRNA) sequence (SEQ ID NO: 4) and amino acid sequence (SEQ ID NO: 10) for type 4 Muscarinic Acetylcholine Receptor (M4).

FIG. 25 shows the nucleic acid (mRNA) sequence (SEQ ID NO: 5) and amino acid sequence (SEQ ID NO: 11) for type 5 Muscarinic Acetylcholine Receptor (M5).

FIG. 26 shows the nucleic acid (mRNA) sequence (SEQ ID NO: 6) for RTP1S.

DEFINITIONS

Figure 6A:
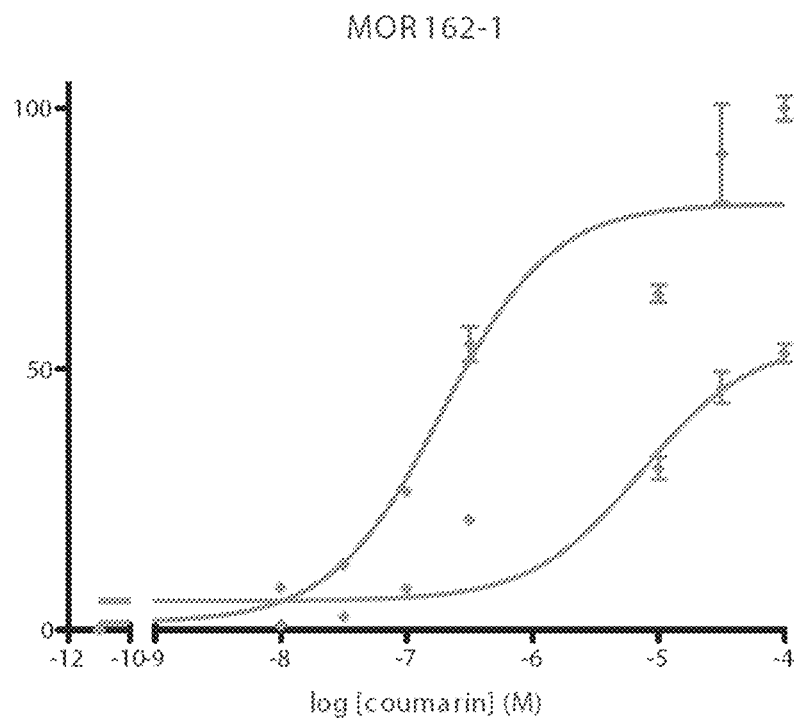
FIGS. 6A—QQ show that M3 enhances the function of wide variety of mammalian ORs. Dose response curves of luciferase assays using over 30 mammalian ORs with or without M3 are shown. All ORs tested are Rho-tagged unless otherwise noted. Average values were taken from quadruplet samples and experiment was replicated at least twice. In each dose response curve shown, the data corresponding to the higher normalized response is M3. In each dose response curve shown, the data corresponding to the lower normalized response is PC1. In each dose response curve shown, the Y axis is "normalized response." In each dose response curve shown, the X axis is "log [coumarin] (M)".
Figure 6B:
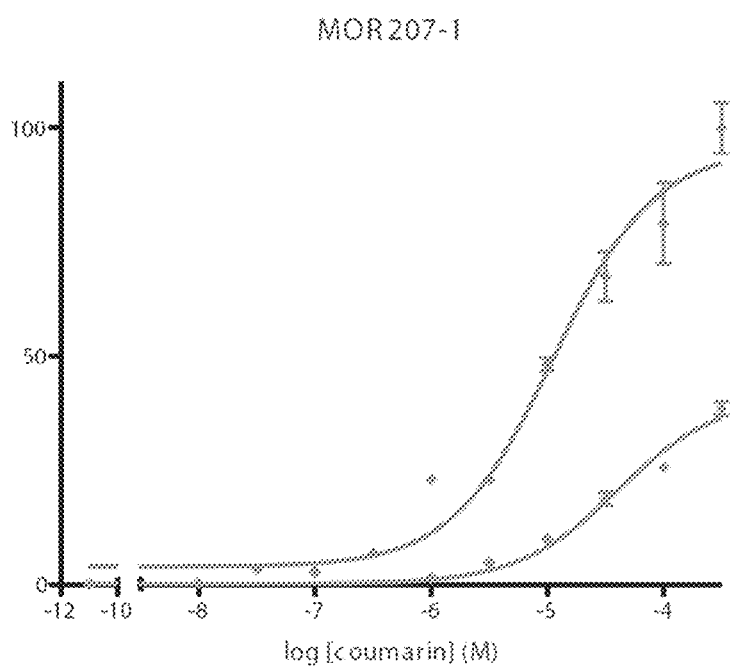
Figure 6C:
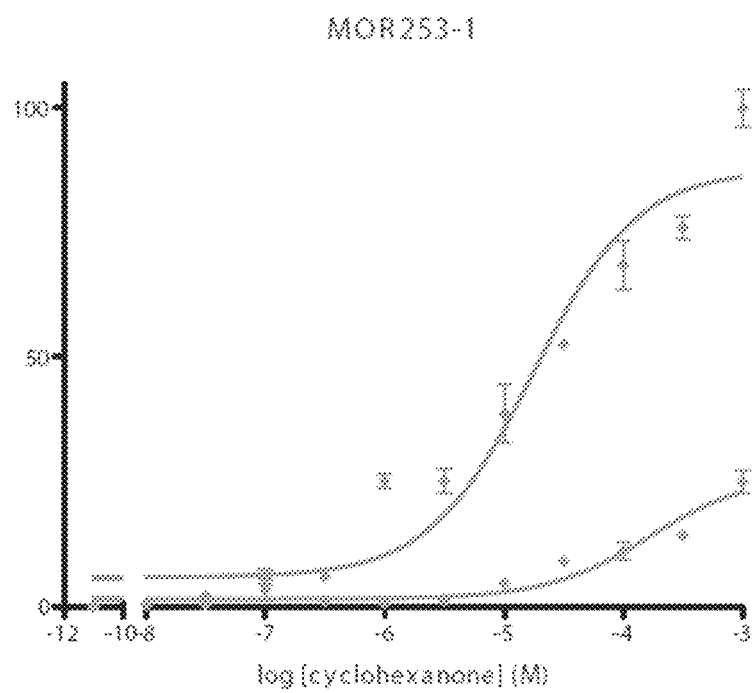
Figure 6D:
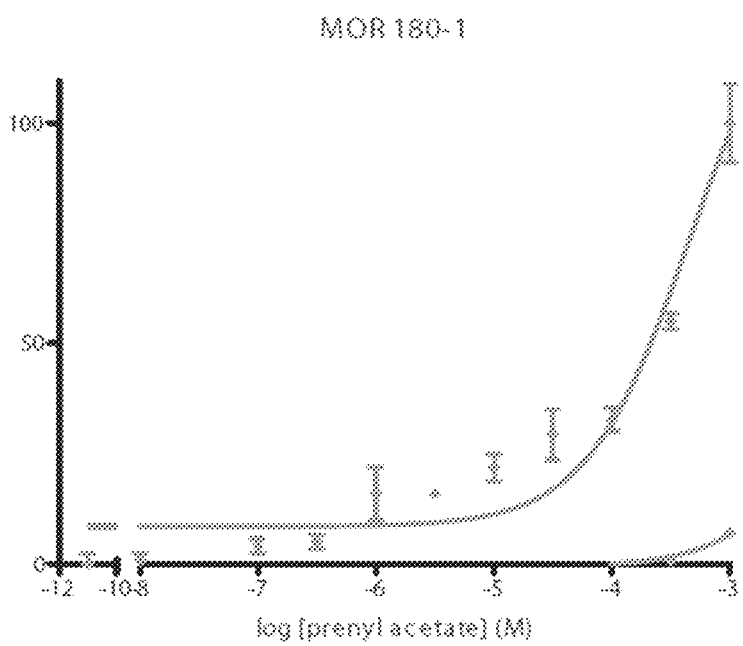
Figure 6E:
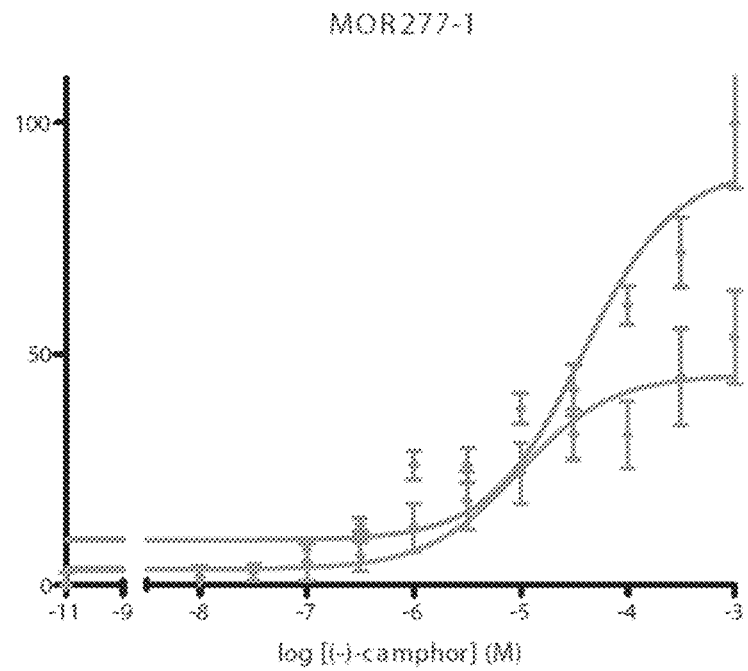
Figure 6F:
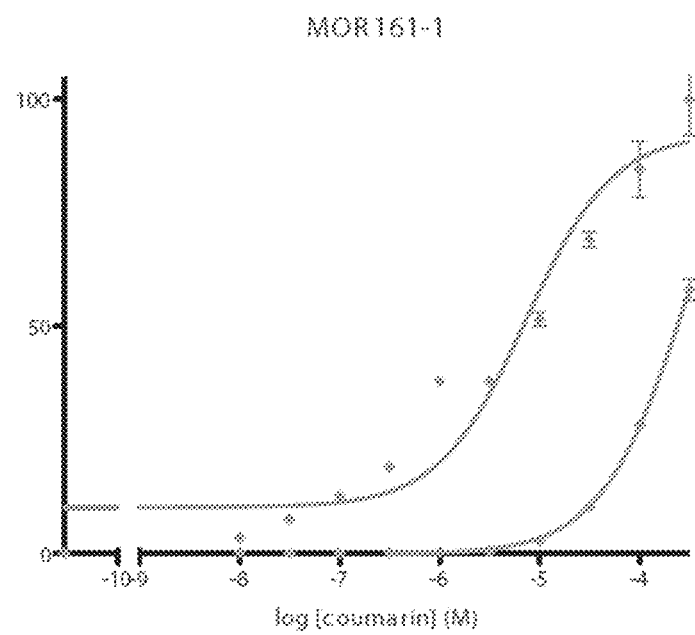
Figure 6G:
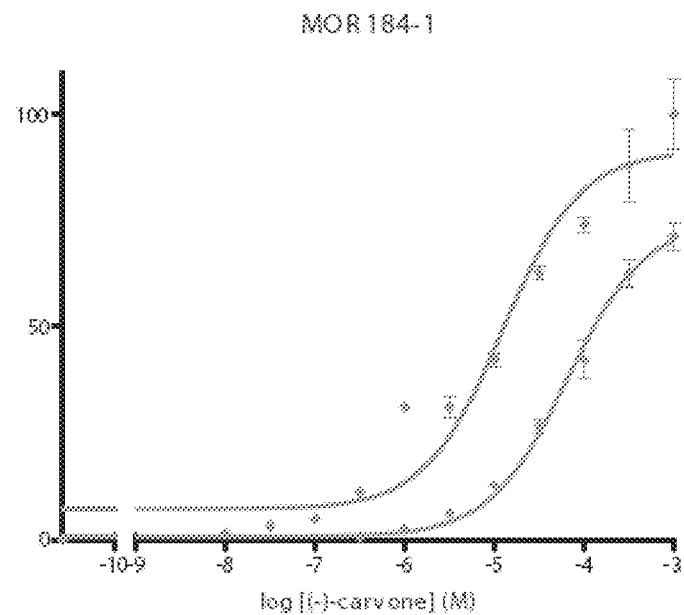
Figure 6H:
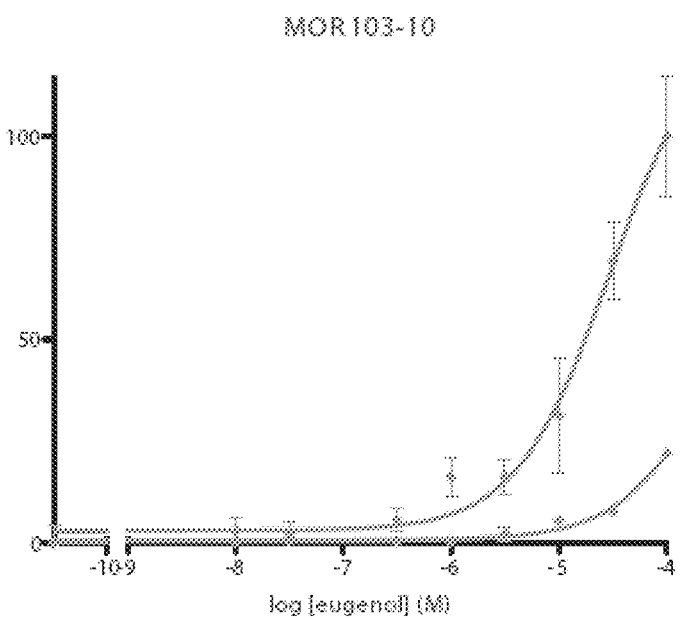
Figure 6I:
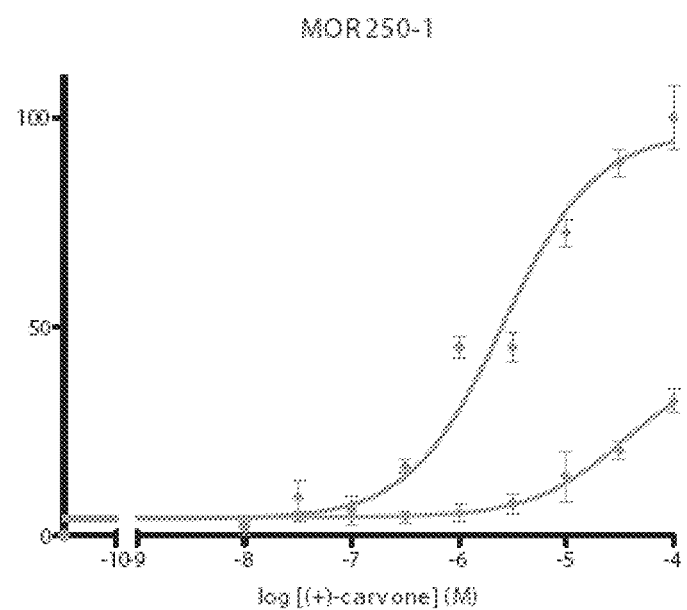
Figure 6J:
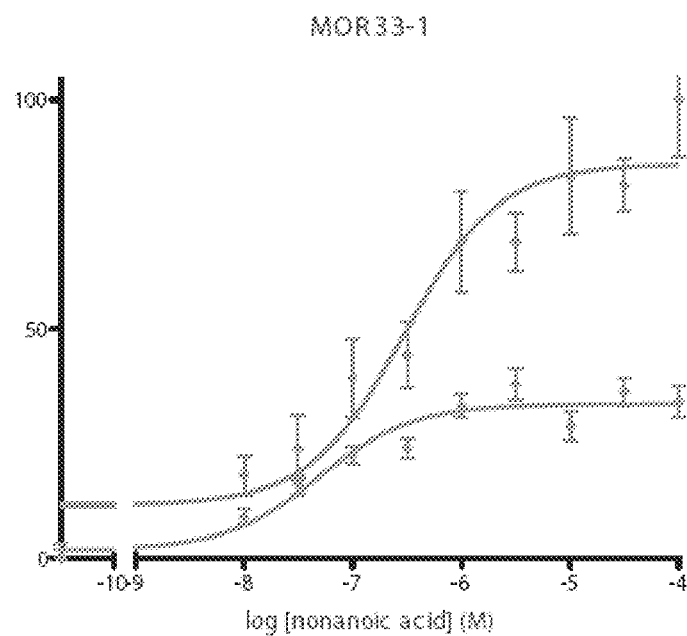
Figure 6K:
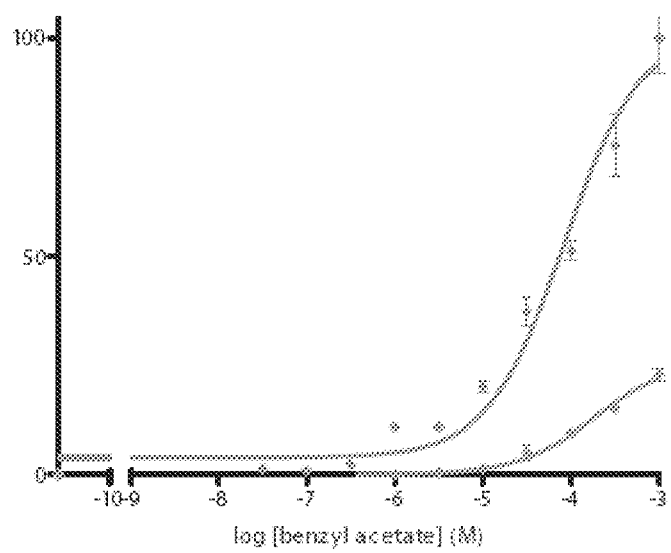
Figure 6L:
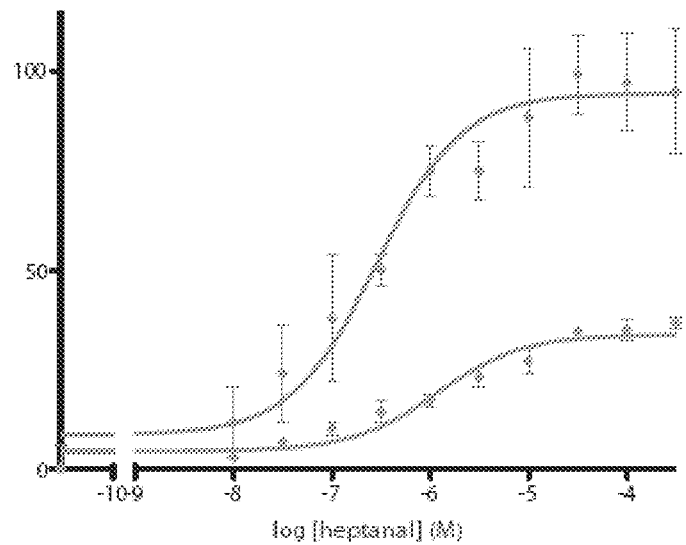
Figure 6M:
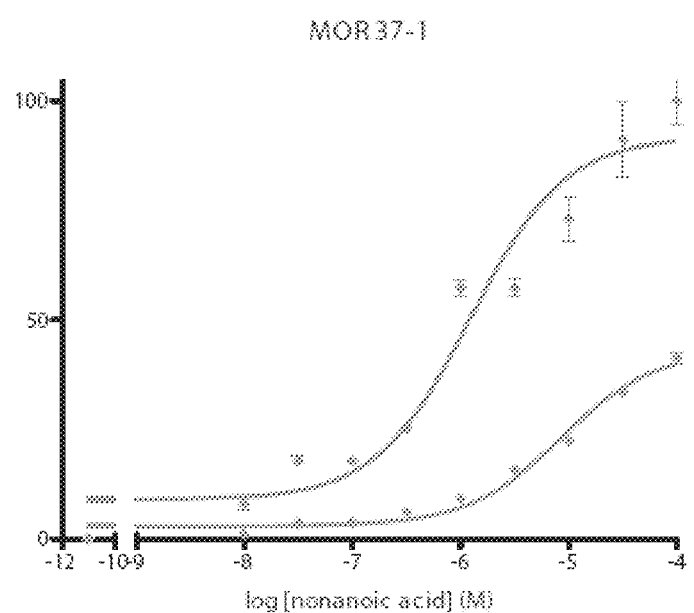
Figure 6N:
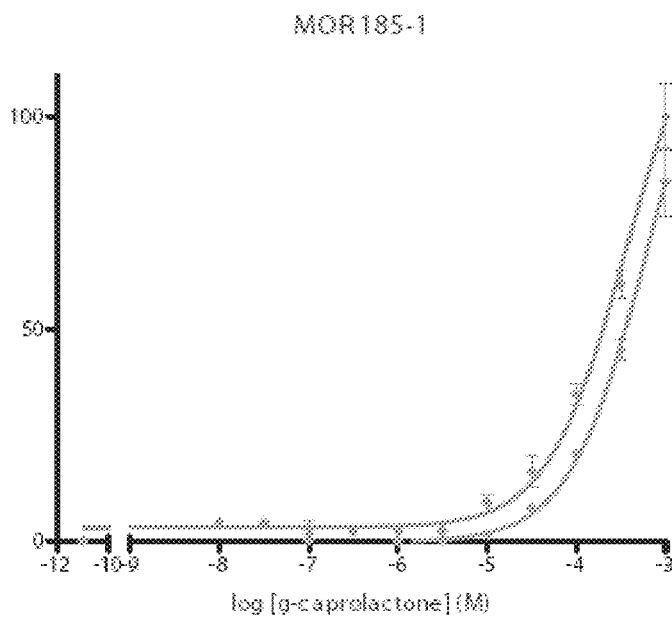
Figures 6O, 6P:
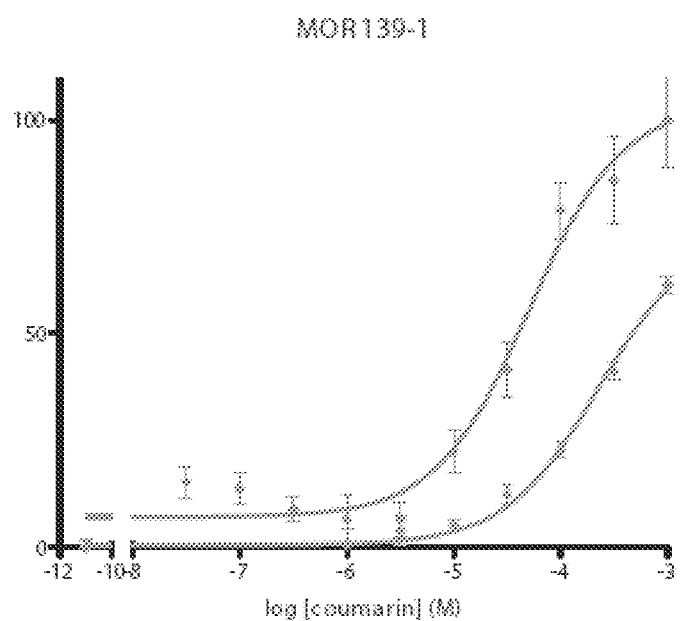
Figure 6Q:
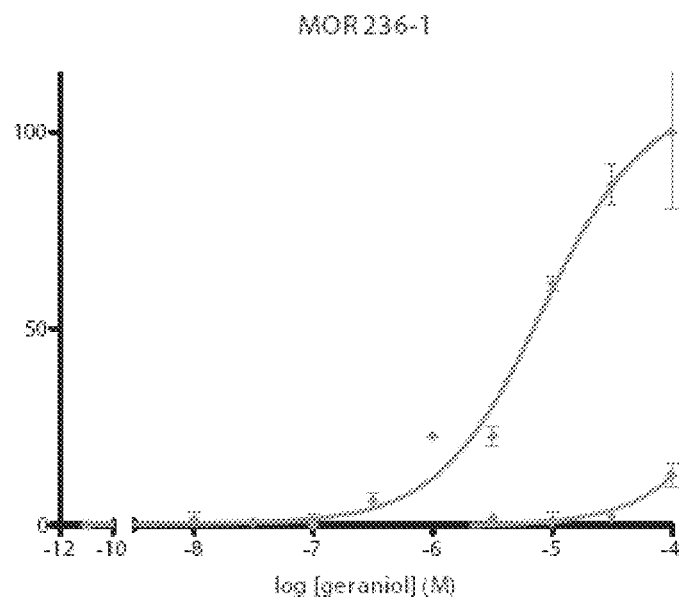
Figure 6R:
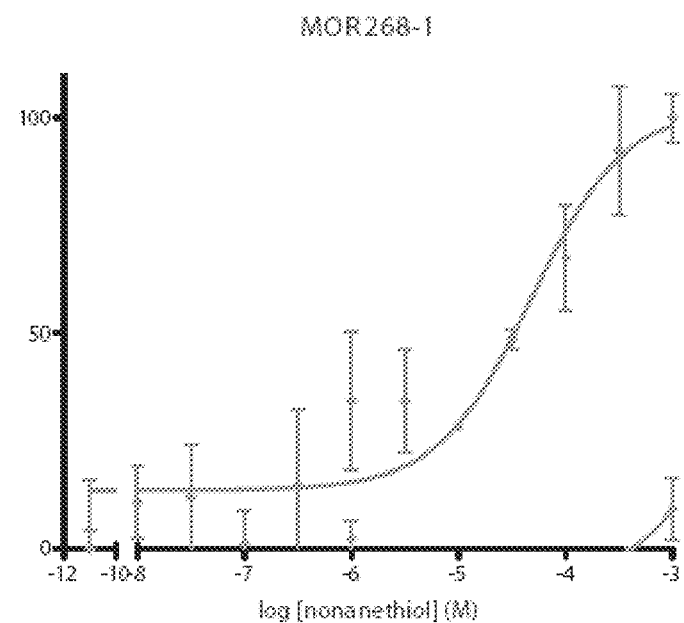
Figure 6S:
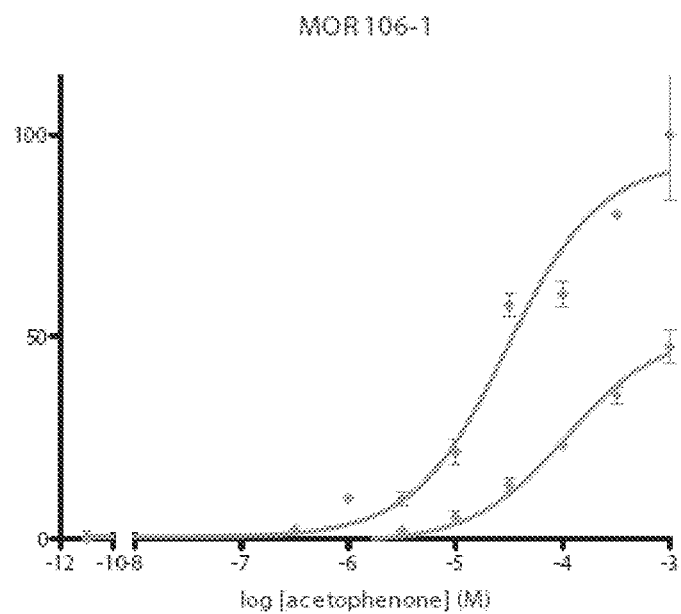
Figure 6T:
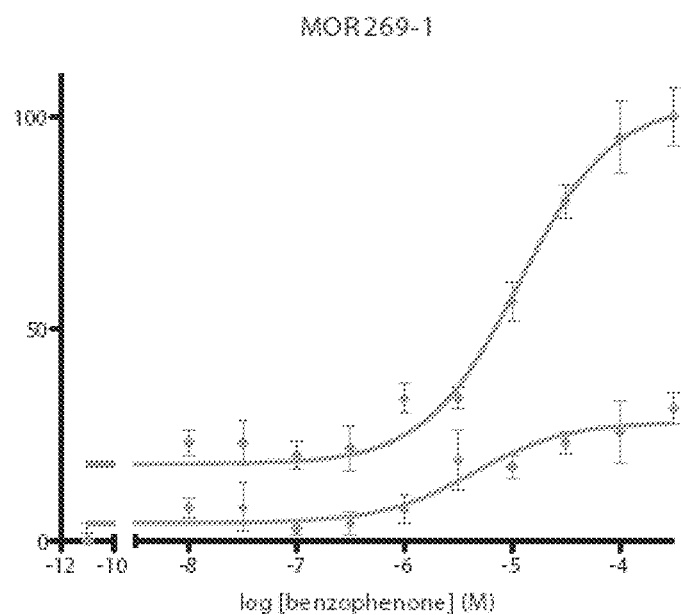
Figure 6U:
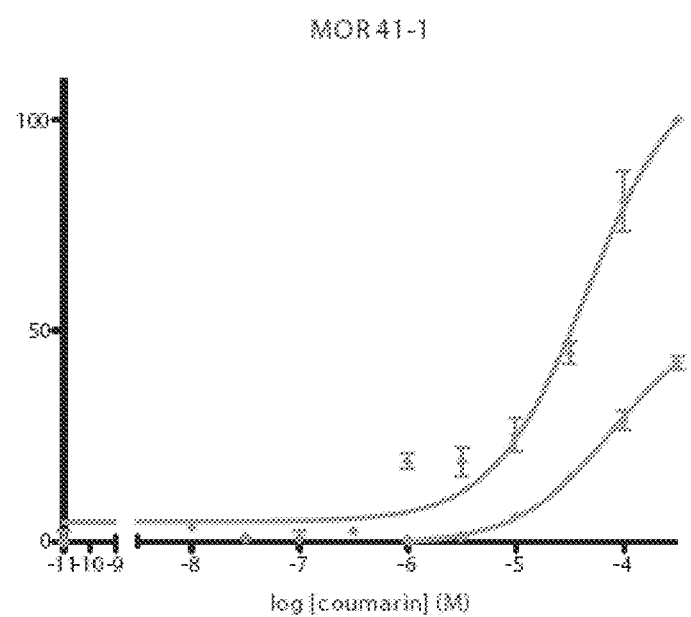
Figure 6V:
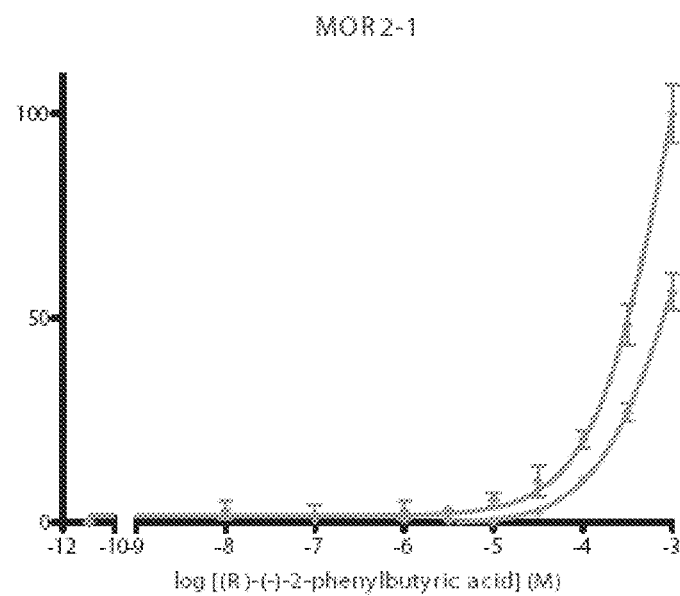
Figure 6W:
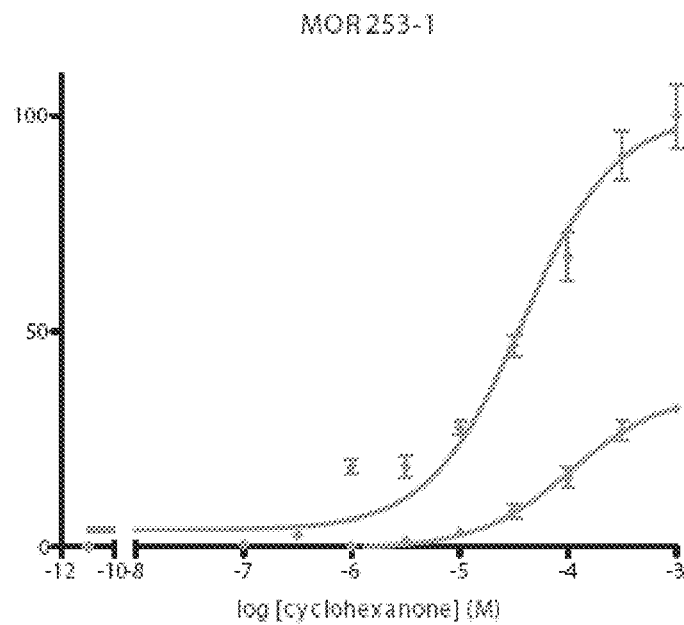
Figure 6X:
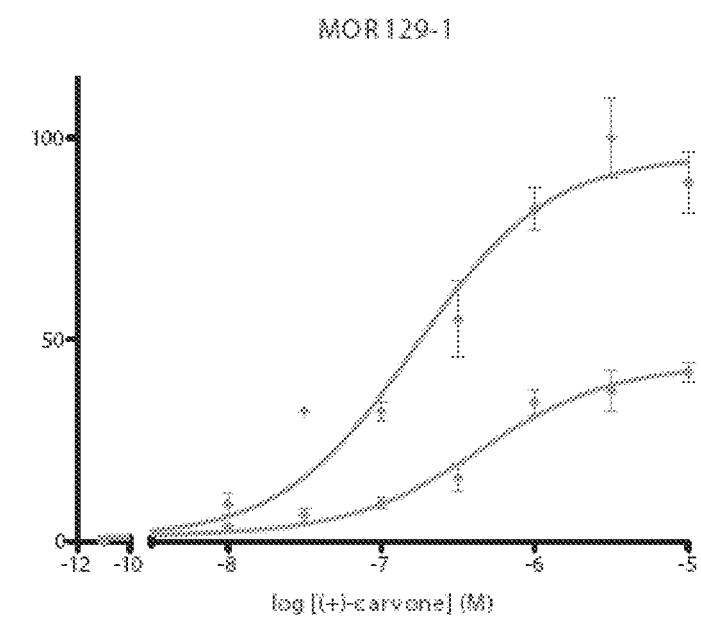
Figure 6Y:
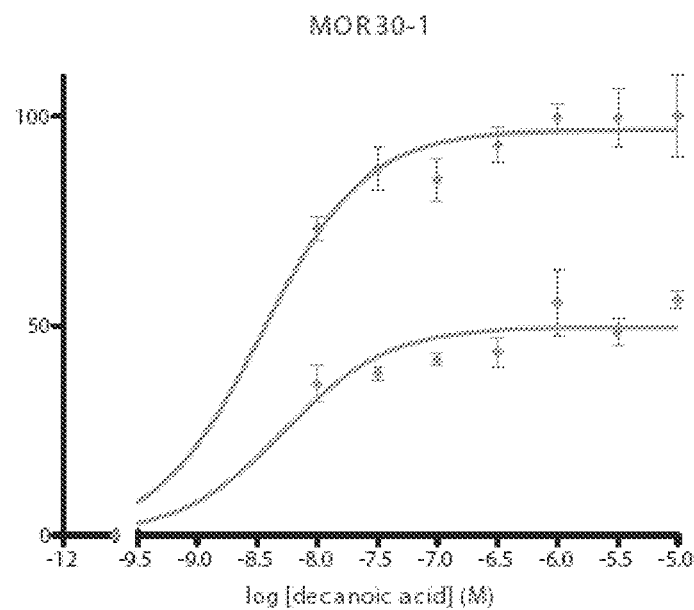
Figure 6Z:
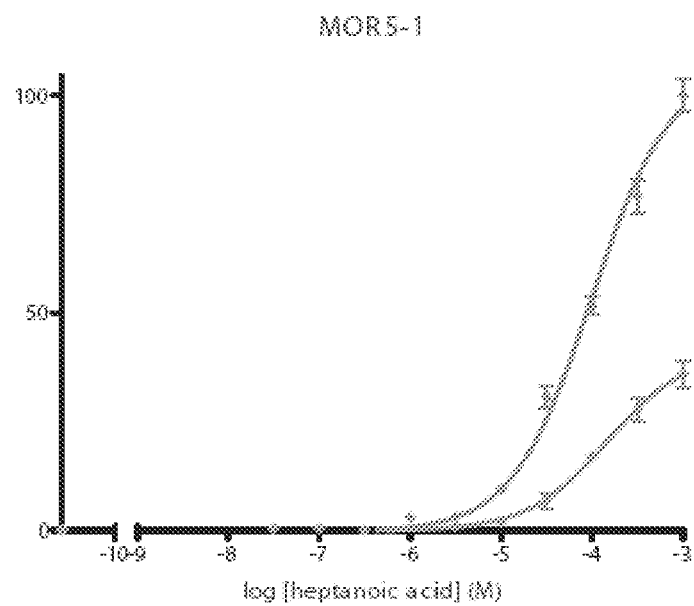
Figure 6A:
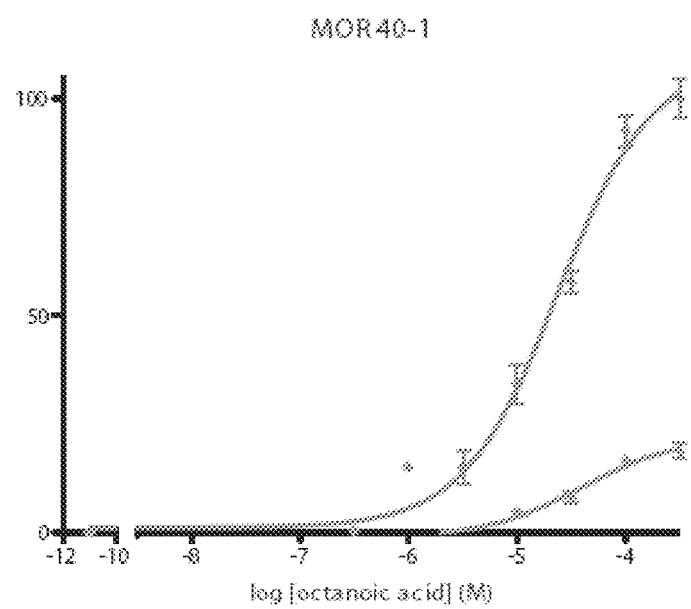
Figure 6B:
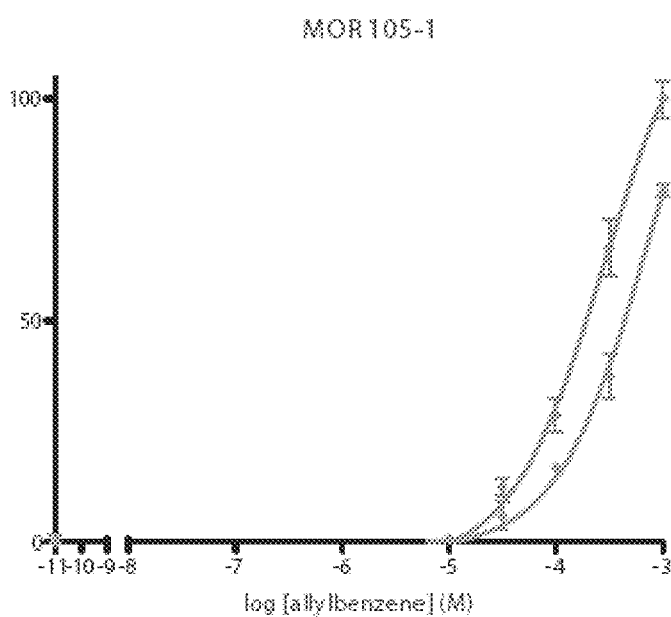
Figure 6C:
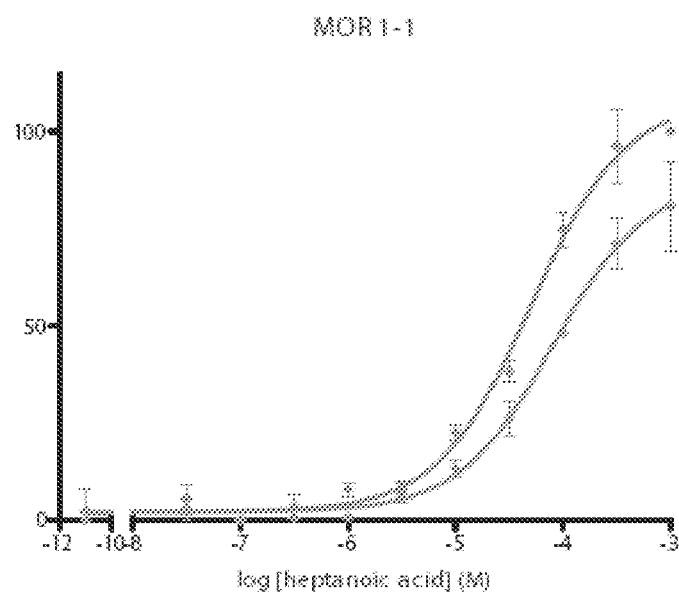
Figure 6D:
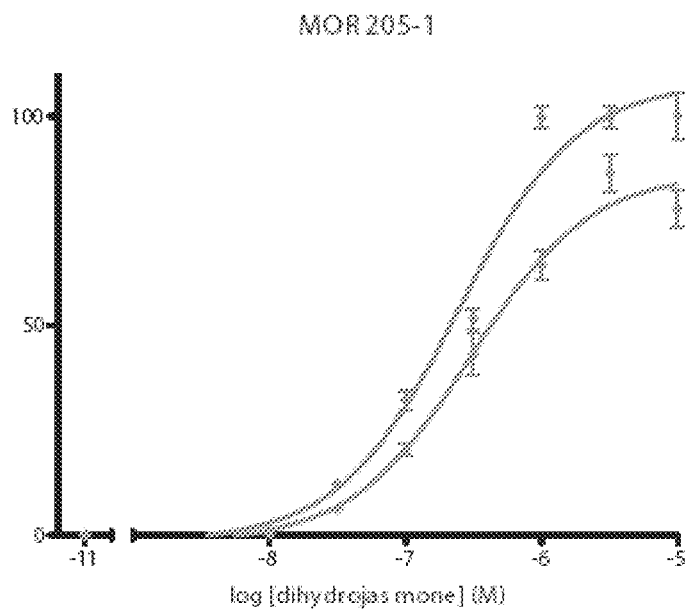
Figure 6E:
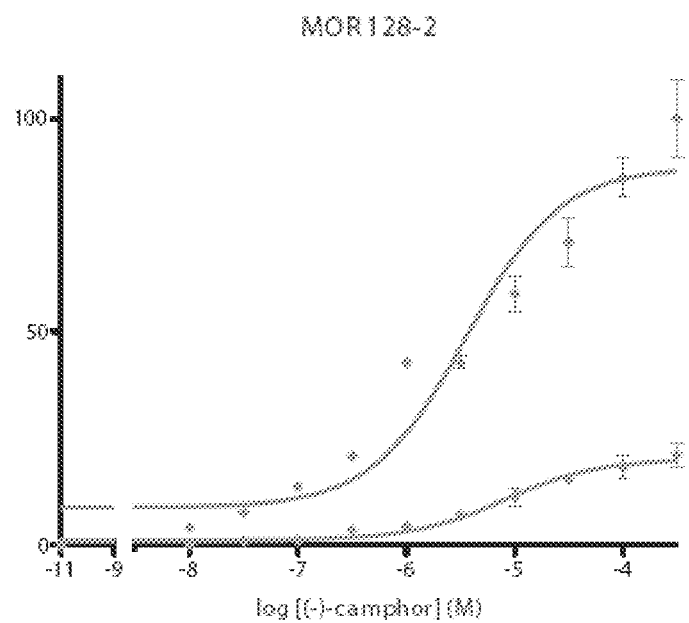
Figure 6F:
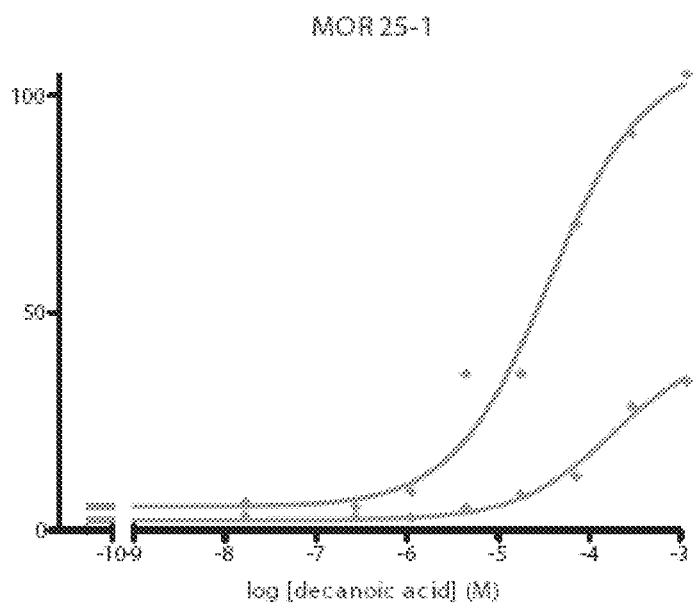
Figure 6G:
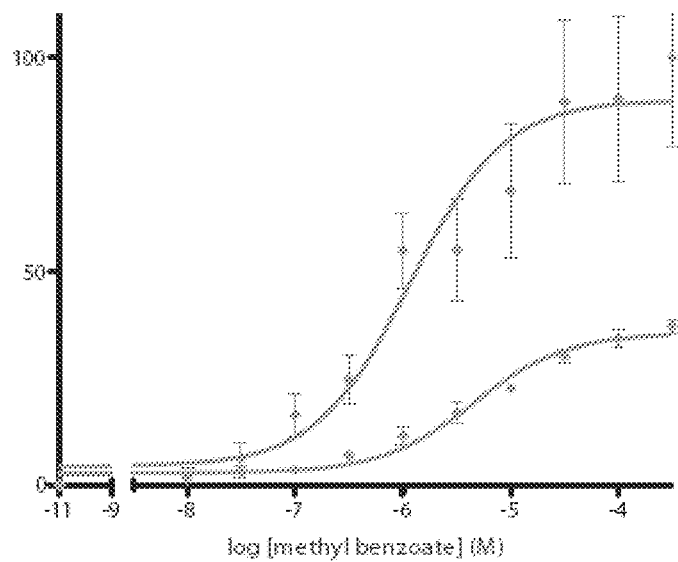
Figure 6H:
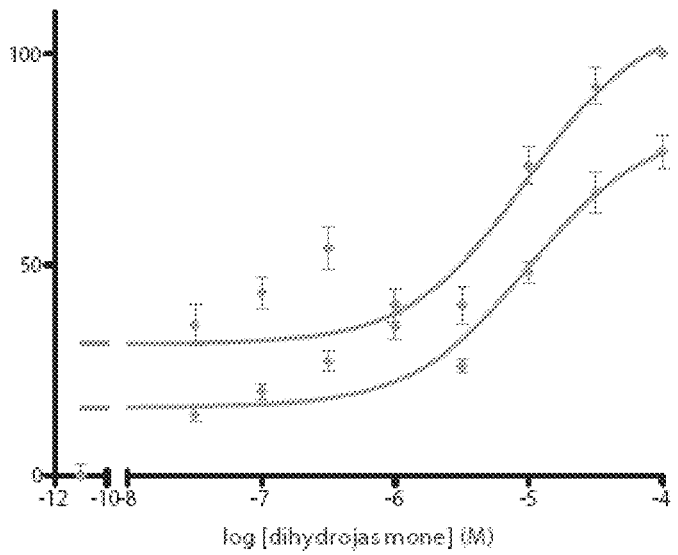
Figure 6I:
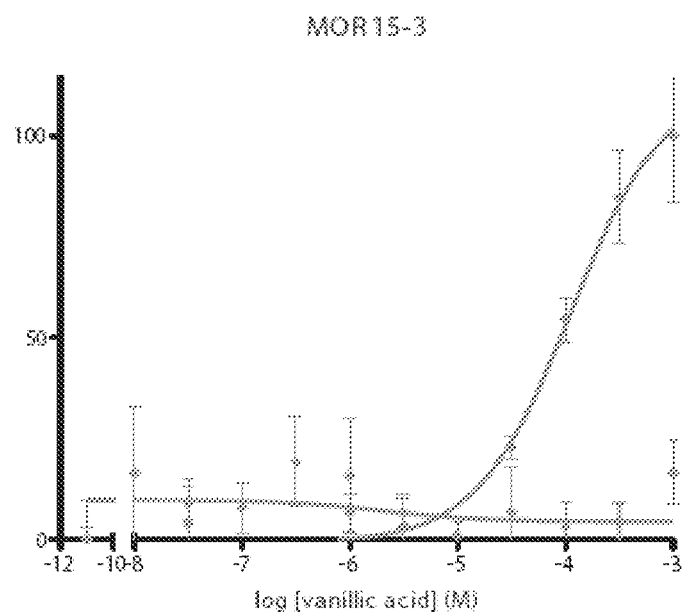
Figure 6J:
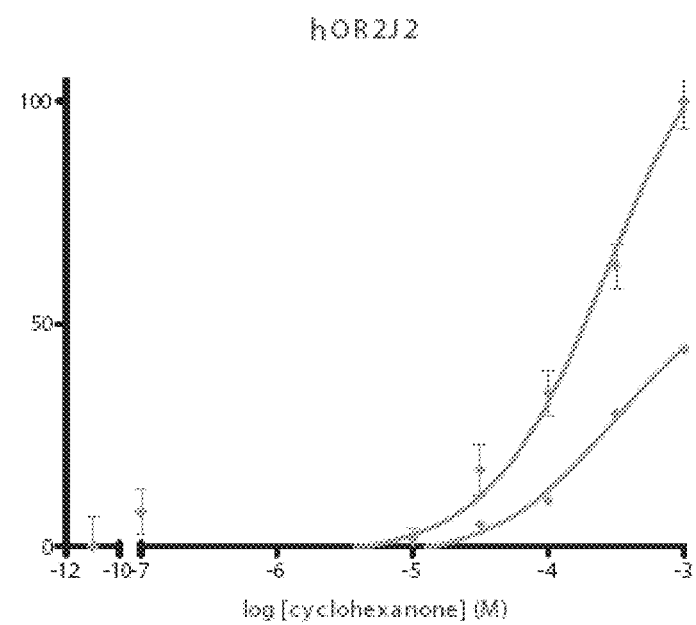
Figure 6K:
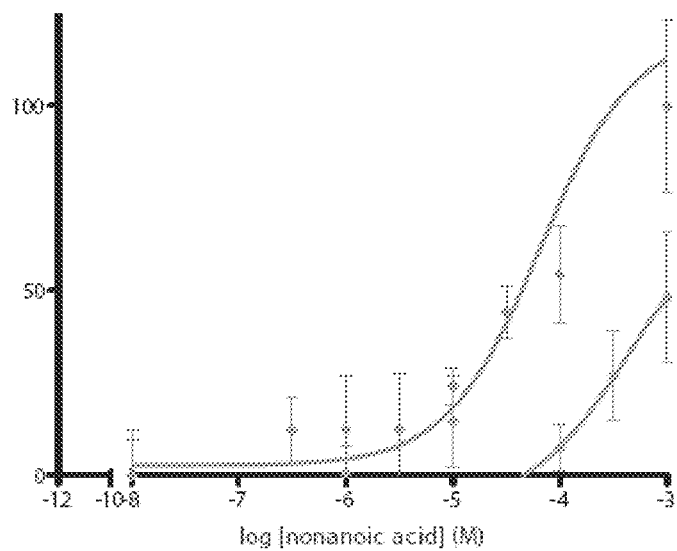
Figure 6L:
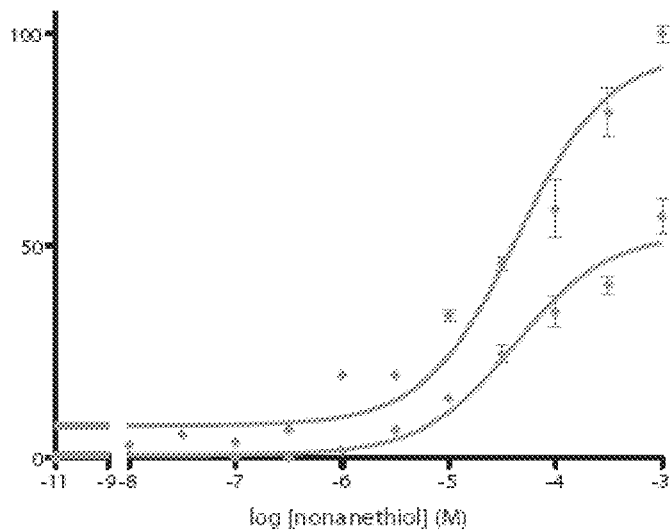
Figure 6M:
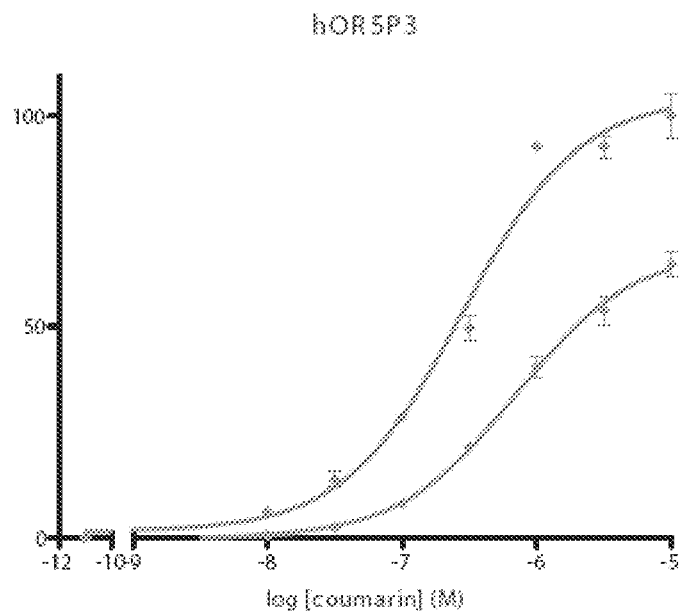
Figure 6N:
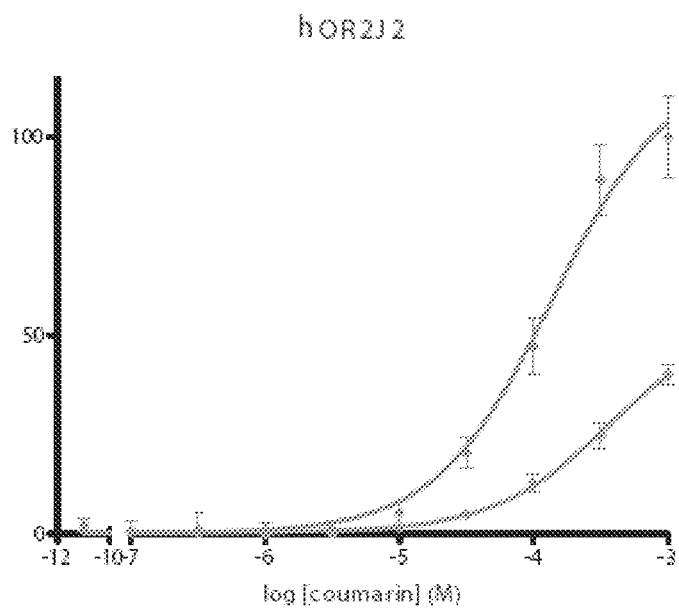
Figure 6O:
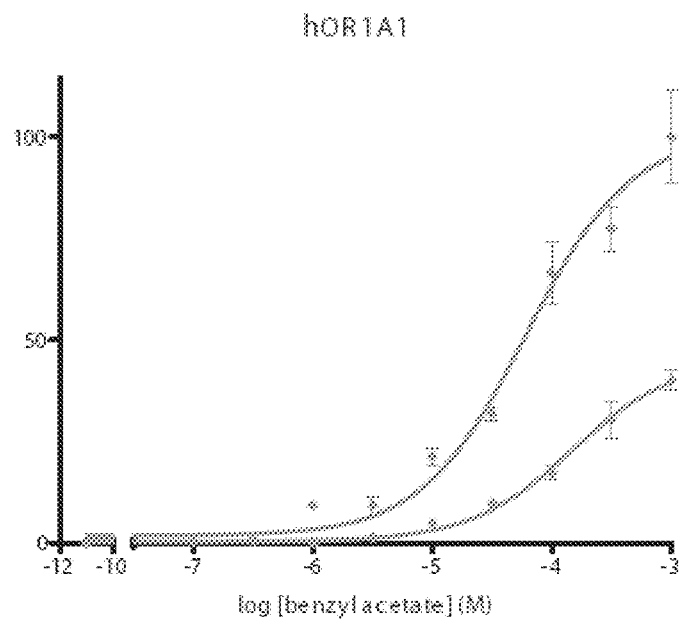
Figure 6P:
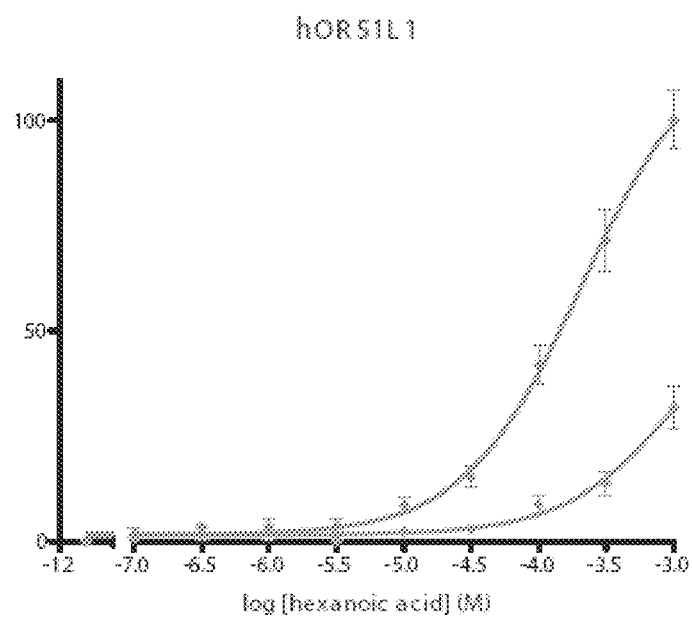
Figure 6Q:
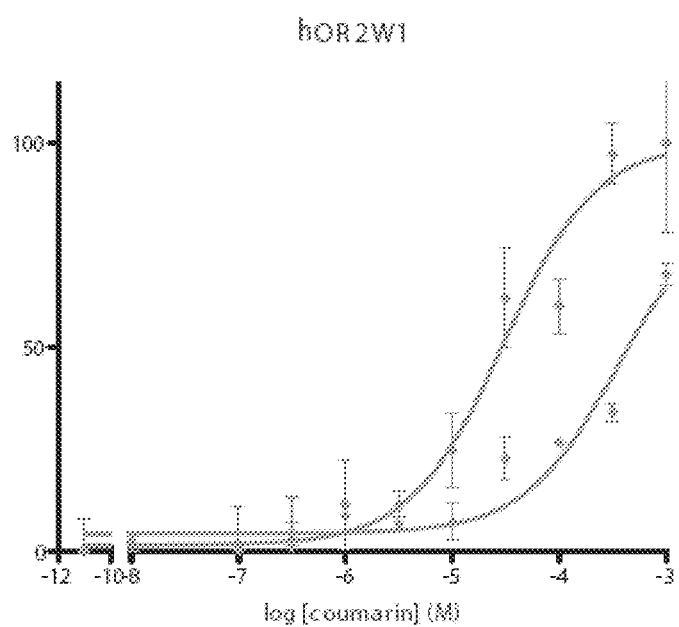

To facilitate understanding of the invention, a number of terms are defined below.

As used herein, the term "muscarinic receptor" refers to the G-protein coupled muscarinic acetylcholine receptors (mAChs) found in the plasma membranes of neurons and other cells and respond to acetylcholine. There are five subtypes of muscarinic receptors, termed M1-M5. The term "Muscarinic Acetylcholine Receptor" when used in reference to proteins or nucleic acid refers to a Muscarinic Acetylcholine Receptor protein or nucleic acid encoding a Muscarinic Acetylcholine Receptor protein of the present invention. The term Muscarinic Acetylcholine Receptor encompasses both proteins that are identical to wild-type Muscarinic Acetylcholine Receptors (e.g., M1, M2, M3, M4 and M5) and those that are derived from wild-type Muscarinic Acetylcholine Receptors (e.g. variants of Muscarinic Acetylcholine Receptor polypeptides of the present invention). In some embodiments, the "Muscarinic Acetylcholine Receptor" is a wild type Muscarinic Acetylcholine Receptor nucleic acid (mRNA) (e.g., SEQ ID NOs: 1-5) or a polypeptide encoded by the wild type Muscarinic Acetylcholine Receptor amino acid sequence (e.g., SEQ ID NOs:7-11).

As used herein, the term "odorant receptor" refers to odorant receptors generated from olfactory sensory neurons. Examples of odorant receptors include, but are not limited to, OR-S6, Olfr62, S6/79, S18, S46, S50, MOR23-1, MOR31-4, MOR31-6, MOR32-5 and MOR32-11.

As used herein, the term "odorant receptor cell surface localization" or equivalent terms refer to the molecular transport of an odorant receptor to a cell surface membrane. Examples of cell surface localization includes, but is not limited to, localization to cilia at the tip of a dendrite, and localization to an axon terminal.

As used herein, the term "odorant receptor functional expression" or equivalent terms, refer to an odorant receptor's ability to interact with an odorant receptor ligand (e.g., an odiferous molecule).

As used herein, the term "olfactory disorder," "olfactory dysfunction," "olfactory disease" or similar term refers to a disorder, dysfunction or disease resulting in a diminished olfactory sensation (e.g., smell aberration). Examples of olfactory disorders, dysfunctions and/or diseases include, but are not limited to, anosmia, hyposmia, dysomia, phantosmia, hyperosmia, olfactory agnosia, head trauma, upper respiratory infections, tumors of the anterior cranial fossa, Kallmann syndrome, Foster Kennedy syndrome, Parkinson's disease, Alzheimer's disease, Huntington chorea, and exposure to toxic chemicals or infections. Diminished olfactory sensation is classified as anosmia—absence of smell sensation; hyposmia—decreased smell sensation; dysosmia—distortion of smell sensation; cacosmia—sensation of a bad or foul smell; and parosmia—sensation of smell in the absence of appropriate stimulus.

As used herein, the term "M3," "muscarinic acetylcholine receptor $M_3$," "type 3 muscarinic acetylcholine receptor," or similar terms, when used in reference to a protein or nucleic acid refers to a M3 protein or nucleic acid encoding a M3 protein of the present invention. M3 is a muscarinic acetylcholine receptor encoded by the human gene CHRM3 (see, e.g., Goyal R K, et al., (1989) N. Engl. J. Med. 321 (15): 1022-9; herein incorporated by reference in its entirety). In experiments conducted during the course of developing embodiments for the present invention, it was demonstrated that the interaction of ORs with the type 3 muscarinic acetylcholine receptor M3, which is coexpressed with ORs in olfactory sensory neurons (OSNs), is important for the response of ORs to cognate odor ligands. For example, it was shown that in HEK293T cells, ORs and M3 can be coprecipitated, and coexpression of M3 increases the potency and efficacy of odor-elicited responses of a broad range of ORs. In addition, by monitoring the odor response of acutely dissociated mice OSNs, odor-dependent activation of OSNs is attenuated by M3-selective antagonists was demonstrated. In parallel, it was shown that when M3 is coexpressed, OR activation can be further enhanced by muscarinic agonists and inhibited by muscarinic antagonists in HEK293T cells. Furthermore, it was shown that M3-dependent potentiation of OR signaling is synergistic with that of RTP1S, an accessory factor required for efficient OR membrane-targeting. However, coexpression of M3 does not seem to enhance the cell-surface expression of ORs, suggesting that M3 acts through mechanism independent of RTP1, for example, by enhancing the response of ORs already at the cell surface. Finally, OR activation by cognate odors transactivates M3 in the absence of M3 agonist. The crosstalk between ORs and M3 suggests, for example, that the functional coupling of ORs and M3 is important for robust OR activation. The term M3 encompasses both proteins that are identical to wild-type M3 and those that are derived from wild type M3 (e.g., variants of M3 polypeptides of the present invention) or chimeric genes constructed with portions of M3 coding regions). In some embodiments, the "M3" is a wild type M3 nucleic acid (mRNA) (SEQ ID NO:3) or polypeptide encoded by the wild type amino acid sequence (SEQ ID NO: 9). Examples of M3 agonists include, but are not limited to, acetylcholine, bethanechol, carbachol, oxotremorine, L-689,660 (e.g., a mixed M1/M3 agonist), and pilocarpine. Examples of M3 antagonists include, but are not limited to, atropine, 4-DAMP (1,1-Dimethyl-4-diphenylacetoxypiperidinium iodide), DAU-5884 (8-Methyl-8-azabicyclo-3-endo[1.2.3]oct-3-yl-1,4-dihydro-2-oxo-3(2H)-quinazolinecarboxylic acid ester), dicycloverine, J-104,129 ((aR)-a-Cyclopentyl-a-hydroxy-N-[1-(4-methyl-3-pentenyl)-4-piperidinyl]benzeneacetamide), tolterodine, oxybutynin, ipratropium, darifenacin, titropium, and Zamifenacin ((3R)-1-[2-(1-,3-Benzodioxol-5-yl)ethyl]-3-(diphenylmethoxy)piperidine).

As used herein, the term "M1," "muscarinic acetylcholine receptor $M_1$," "type 1 muscarinic acetylcholine receptor," or similar terms, when used in reference to a protein or nucleic acid refers to a M1 protein or nucleic acid encoding a M1 protein of the present invention. M1 is a muscarinic acetylcholine receptor encoded by the human gene CHRM1, localized to 11q13. The term M1 encompasses both proteins that are identical to wild-type M1 and those that are derived from wild type M1 (e.g., variants of M1 polypeptides of the present invention) or chimeric genes constructed with portions of M1 coding regions). In some embodiments, the "M1" is a wild type M1 nucleic acid (mRNA) (SEQ ID NO:1) or polypeptide encoded by the wild type amino acid sequence (SEQ ID NO: 7). Examples of M1 agonists include, but are not limited to, acetylcholine, muscarine, carbachol, oxotremorine, L-689,660 (e.g. a mixed M1/M3 agonist), McN-A-343 (e.g., a mixed M1/M4 agonist), vedaclidine, and xanomeline. Examples of M1 allosteric modulators include, but are not limited to, benzylquinolone carboxylic acid, VU-0090157 and VU-0029767 (see, e.g., Shirey J K, (November 2009) J. Neurosci. 29 (45): 14271-86; Marlo J E, et al., (2008) Mol. Pharmacol. 75 (3): 577; each herein incorporated by refernece in its entirety). Examples of M1 antagonists include, but are not limited to, atropine, dicycloverine, tolterodine, oxybutynin, ipratropium, mamba toxin MT7, pirenzepine, and telenzepine.

As used herein, the term "M2," "muscarinic acetylcholine receptor M2," "type 2 muscarinic acetylcholine receptor," or similar terms, when used in reference to a protein or nucleic acid refers to a M2 protein or nucleic acid encoding a M2 protein of the present invention. M2 is a muscarinic acetylcholine receptor encoded by the human gene CHRM2. The term M2 encompasses both proteins that are identical to wild-type M2 and those that are derived from wild type M2 (e.g., variants of M2 polypeptides of the present invention) or chimeric genes constructed with portions of M2 coding regions). In some embodiments, the "M2" is a wild type M2 nucleic acid (mRNA) (SEQ ID NO:2) or polypeptide encoded by the wild type amino acid sequence (SEQ ID NO: 8). Examples of M2 agonists include, but are not limited to, bethanechol and (2S,2'R,3'S,5'R)-1-methyl-2-(2-methyl-1, 3-oxathiolan-5-yl)pyrrolidine 3-sulfoxide methyl iodide (selective for M2 but only partial agonist) (see, e.g., Scapecchi S, et al., J. Med. Chem. 49 (6): 1925-31; herein incorporated by reference in its entirety). Examples of M2 antagonists include, but are not limited to, dimethindene, Otenzepad-11-[2-[(Diethylamino)methyl]-1-piperidinyl]acetyl)-5,11-dihydro-6H-pyrido[2,3-b][1,4]benzodiazepin-6-one), AQRA-741-11-([4-[4-(Diethylamino)butyl]-1-piperidinyl] acetyl)-5,11-dihydro-6H-pyrido[2,3-b][1,4]benzodiazepin-6-one), and AFDX-384 (mixed M2/M4 antagonist)-N-[2-[2-[(Dipropylamino)methyl]-1-piperidinyl]ethyl]-5,6-dihydro-6-oxo-11H-pyrido[2,3-b][1,4]benzodiazepine-11-carboxamide).

As used herein, the term "M4," "muscarinic acetylcholine receptor M4," "type 4 muscarinic acetylcholine receptor," or similar terms, when used in reference to a protein or nucleic acid refers to a M4 protein or nucleic acid encoding a M4 protein of the present invention. M4 is a muscarinic acetylcholine receptor encoded by the human gene CHRM4. The term M4 encompasses both proteins that are identical to wild-type M4 and those that are derived from wild type M4 (e.g., variants of M4 polypeptides of the present invention) or chimeric genes constructed with portions of M4 coding regions). In some embodiments, the "M4" is a wild type M4 nucleic acid (mRNA) (SEQ ID NO:4) or polypeptide encoded by the wild type amino acid sequence (SEQ ID NO: 10). Examples of M4 agonists include, but are not limited to, acetylcholine, carbachol, oxotremorine, LY-2033298, VU-0152100, VU-0152099 (see, e.g., Chan W Y, et al (2008) PNAS 105 (31); Brady A E, et al. (2008) J. Pharmacol. Exp. Ther. 327 (3): 941-53; each herein incorporated by reference in its entirety). Examples of M4 antagonists include, but are not limited to, AFDX-384 (mixed M4/M4 antagonist)-N-[2-[2-[(Dipropylamino)methyl]-1-piperidinyl]ethyl]-5,6-dihydro-6-oxo-11H-pyrido[2,3-b][1,4]benzodiazepine-11-carboxamide), himbacine, tropicamide, and PD-102,807 (3,6a,11,14-Tetrahydro-9-methoxy-2-methyl-(12H)-isoquino[1,2-b]pyrrolo[3,2-f][1,3]benzoxazine-1-carboxylic acid ethyl ester).

As used herein, the term "M5," "muscarinic acetylcholine receptor M5," "type 5 muscarinic acetylcholine receptor," or similar terms, when used in reference to a protein or nucleic acid refers to a M5 protein or nucleic acid encoding a M5 protein of the present invention. M5 is a muscarinic acetylcholine receptor encoded by the human gene CHRM5. The term M5 encompasses both proteins that are identical to wild-type M5 and those that are derived from wild type M5 (e.g., variants of M5 polypeptides of the present invention) or chimeric genes constructed with portions of M5 coding regions). In some embodiments, the "M5" is a wild type M5 nucleic acid (mRNA) (SEQ ID NO:5) or polypeptide encoded by the wild type amino acid sequence (SEQ ID NO: 11). Examples of M5 agonists include, but are not limited to, milameline ((E)-1,2,5,6-Tetrahydro-1-methyl-3-pyridinecarboxaldehyde-O-methyloxime), and sabcomeline. An example of a M5 allosteric modulator is VU-0238429 (see, e.g., Bridges, et al. (2009) J. Med. Chem. 52 (11): 3445-8; herein incorporated by reference in its entirety). An examples of an M5 antagonists is xanomeline.

As used herein, the term "RTP" when used in reference to proteins or nucleic acid refers to a RTP protein or nucleic acid encoding a RTP protein. RTP polypeptides have been shown to assist in cell surface localization of odorant receptors (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety). The term RTP encompasses both proteins that are identical to wild-type RTPs (e.g., RTP1, RTP2, RTP3, and RTP4) and those that are derived from wild-type RTP (e.g. variants of RTP polypeptides including but not limited to RTP1S, RTP1-A, RTP1-B, RTP1-C, RTP1-D, RTP1-E, RTP1-A1, RTP1-D1, RTP-D2, RTP-D3, or chimeric genes constructed with portions of RTP1 coding regions (e.g., RTP1-A1-A, RTP1-A1-D2, RTP1-A1-D1, RTP4-A1-A, RTP4-A1-D2, and RTP4-A1-D1.

As used herein, the term "REEP" when used in reference to proteins or nucleic acid refers to a REEP protein or nucleic acid encoding a REEP protein. REEP polypeptides have been shown to assist in cell surface localization of odorant receptors (see, e.g., U.S. Pat. Nos. 7,425,445, 7,838, 288, 7,691,592; U.S. Patent Application Publication Nos. 2010/0222561, 2009/0124003, 2009/0092997; each herein incorporated by reference in its entirety). The term REEP encompasses both proteins that are identical to wild-type REEPs (e.g., REEP1, REEP2, REEP3, REEP4, REEP5, and REEP6) and those that are derived from wild-type REEP (e.g. variants of REEP polypeptides).

As used herein, the terms "subject" and "patient" refer to any animal, such as a mammal like a dog, cat, bird, livestock, and preferably a human. Specific examples of "subjects" and "patients" include, but are not limited to, individuals with an olfactory disorder, and individuals with olfactory disorder-related characteristics or symptoms.

As used herein, the phrase "symptoms of an olfactory disorder" and "characteristics of an olfactory disorder" include, but are not limited to, a diminished olfactory sensation (e.g., smell aberration).

The phrase "under conditions such that the symptoms are reduced" refers to any degree of qualitative or quantitative reduction in detectable symptoms of olfactory disorders, including but not limited to, a detectable impact on the rate of recovery from disease, or the reduction of at least one symptom of an olfactory disorder.

The term "siRNAs" refers to short interfering RNAs. Methods for the use of siRNAs are described in U.S. Patent App. No.: 20030148519/A1 (herein incorporated by reference). In some embodiments, siRNAs comprise a duplex, or double-stranded region, of about 18-25 nucleotides long;

often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

The term "gene" refers to a nucleic acid (e.g., DNA) sequence that comprises coding sequences necessary for the production of a polypeptide, RNA (e.g., including but not limited to, mRNA, tRNA and rRNA) or precursor (e.g., muscarinic acetylcholine receptor (e.g., M1, M2, M3, M4, M5)). The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "muscarinic acetylcholine receptor (e.g., M1, M2, M3, M4, M5) gene," or similar terms, refer to the full-length respective muscarinic acetylcholine receptor (e.g., M1, M2, M3, M4, M5) nucleotide sequence (e.g., contained in SEQ ID NOs:1, 2, 3, 4, and 5, respecrtively). However, it is also intended that the term encompass fragments of the muscarinic acetylcholine receptor (e.g., M1, M2, M3, M4, M5) sequences, chimeric genes constructed with portions of muscarinic acetylcholine receptor (e.g., M1, M2, M3, M4, M5) coding regions, mutants of the muscarinic acetylcholine receptor (e.g., M1, M2, M3, M4, M5) sequences, as well as other domains within the full-length muscarinic acetylcholine receptor (e.g., M1, M2, M3, M4, M5) nucleotide sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified," "mutant," "polymorphism," and "variant" refer to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence 5'-"A-G-T-3'," is complementary to the sequence 3'-"T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Complementarity can include the formation of base pairs between any type of nucleotides, including non-natural bases, modified bases, synthetic bases and the like.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The term "inhibition of binding," when used in reference to nucleic acid binding, refers to inhibition of binding caused by competition of homologous sequences for binding to a target sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_m$" as used herein refers to the Michaelis-Menton constant for an enzyme and is defined as the concentration of the specific substrate at which a given enzyme yields one-half its maximum velocity in an enzyme catalyzed reaction.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$=81.5+0.41(% G+C), when a nucleic acid is in aqueous solution at 1 M NaCl (See e.g., Anderson and Young, Quantitative Filter Hybridization, in *Nucleic Acid Hybridization* [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85-100% identity, preferably about 70-100% identity). With medium stringency conditions, nucleic acid base pairing will occur between nucleic acids with an intermediate frequency of complementary base sequences (e.g., hybridization under "medium stringency" conditions may occur between homologs with about 50-70% identity). Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4$ $H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The present invention is not limited to the hybridization of probes of about 500 nucleotides in length. The present invention contemplates the use of probes between approximately 10 nucleotides up to several thousand (e.g., at least 5000) nucleotides in length. One skilled in the relevant understands that stringency conditions may be altered for probes of other sizes (See e.g., Anderson and Young, Quantitative Filter Hybridization, in *Nucleic Acid Hybridization* [1985] and Sambrook et al., Molecular Cloning: A Laboratory Manual, Cold Spring Harbor Press, NY [1989]).

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman [Smith and Waterman, *Adv. Appl. Math.* 2: 482 (1981)] by the homology alignment algorithm of Needleman and Wunsch [Needleman and Wunsch, *J. Mol. Biol.* 48:443 (1970)], by the search for similarity method of Pearson and Lipman [Pearson and Lipman, *Proc. Natl. Acad. Sci.* (*USA.*) 85:2444 (1988)], by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention (e.g., a muscarinic acetylcholine receptor (e.g., M1, M2, M3, M4, M5)).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

The term "polymorphic locus" is a locus present in a population that shows variation between members of the population (i.e., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

As used herein, the term "genetic variation information" or "genetic variant information" refers to the presence or absence of one or more variant nucleic acid sequences (e.g., polymorphism or mutations) in a given allele of a particular gene (e.g., a muscarinic acetylcholine receptor (e.g., M1, M2, M3, M4, M5) gene of the present invention).

As used herein, the term "detection assay" refers to an assay for detecting the presence or absence of variant nucleic acid sequences (e.g., polymorphisms or mutations) in a given allele of a particular gene (e.g., a muscarinic acetylcholine receptor (e.g., M1, M2, M3, M4, M5) gene).

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," refers to a nucleic acid sequence or structure to be detected or characterized. Thus, the "target" is sought to be sorted out from other nucleic acid sequences. A "segment" is defined as a region of nucleic acid within the target sequence.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a muscarinic acetylcholine receptor (e.g., M1, M2, M3, M4, M5) includes, by way of example, such nucleic acid in cells ordinarily expressing a muscarinic acetylcholine receptor (e.g., M1, M2, M3, M4, M5) where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets, which specify stop codons (i.e., TAA, TAG, TGA).

As used herein, the term "purified" or "to purify" refers to the removal of contaminants from a sample. For example, muscarinic acetylcholine receptor (e.g., M1, M2, M3, M4, M5) antibodies are purified by removal of contaminating non-immunoglobulin proteins; they are also purified by the removal of immunoglobulin that does not bind a muscarinic acetylcholine receptor (e.g., M1, M2, M3, M4, M5) polypeptide. The removal of non-immunoglobulin proteins and/or the removal of immunoglobulins that do not bind a muscarinic acetylcholine receptor (e.g., M1, M2, M3, M4, M5) polypeptide results in an increase in the percent of muscarinic acetylcholine receptor (e.g., M1, M2, M3, M4, M5)-reactive immunoglobulins in the sample. In another example, recombinant muscarinic acetylcholine receptor (e.g., M1, M2, M3, M4, M5) polypeptides are expressed in bacterial host cells and the polypeptides are purified by the removal of host cell proteins; the percent of recombinant muscarinic acetylcholine receptor (e.g., M1, M2, M3, M4, M5) polypeptides is thereby increased in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein, is used to indicate a protein that does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., *Molecular Cloning: A Laboratory Manual*, Cold Spring Harbor Press, NY, pp 9.31-9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign, heterologous, or autologous gene that is placed into an organism by introducing the gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene. The term "autologous gene" is intended to encompass variants (e.g., polymorphisms or mutants) of the naturally occurring gene. The term transgene thus encompasses the replacement of the naturally occurring gene with a variant form of the gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "overexpression" and "overexpressing" and grammatical equivalents, are used in reference to levels of mRNA to indicate a level of expression approximately 3-fold higher than that typically observed in a given tissue in a control or non-transgenic animal.

Levels of mRNA are measured using any of a number of techniques known to those skilled in the art including, but not limited to Northern blot analysis (See, Example 10, for a protocol for performing Northern blot analysis).

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding Muscarinic Acetylcholine Receptors (M1, M2, M3, M4, M5) (e.g., SEQ ID NOs:1, 2, 3, 4 and/or 5) or fragments thereof may be employed as hybridization probes. In this case, the muscarinic acetylcholine receptor (e.g., M1, M2, M3, M4, M5) encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "response," when used in reference to an assay, refers to the generation of a detectable signal (e.g., accumulation of reporter protein, increase in ion concentration, accumulation of a detectable chemical product).

As used herein, the term "reporter gene" refers to a gene encoding a protein that may be assayed. Examples of reporter genes include, but are not limited to, luciferase (See, e.g., deWet et al., Mol. Cell. Biol. 7:725 [1987] and U.S. Pat. Nos. 6,074,859; 5,976,796; 5,674,713; and 5,618,682; all of which are incorporated herein by reference), green fluorescent protein (e.g., GenBank Accession Number U43284; a number of GFP variants are commercially available from CLONTECH Laboratories, Palo Alto, Calif.), chloramphenicol acetyltransferase, β-galactosidase, alkaline phosphatase, and horse radish peroxidase.

DETAILED DESCRIPTION OF THE INVENTION

Odor perception in mammals is a complex process mediated by the activation of ORs expressed at the cilia of millions of olfactory sensory neurons (OSNs) lining the olfactory epithelium (see, e.g., L. Buck, R. Axel, Cell 65, 175 (Apr. 5, 1991); S. Firestein, Nature 413, 211 (2001); each herein incorporated by reference in its entirety). Upon activation by cognate odorants, ORs, which are Class A GPCRs, interact with the stimulatory G protein $G_{\alpha olf}$. Release of $G_{\alpha olf}$ from the βγ subunit then activates type III adenylyl cyclase (ACIII), an enzyme that rapidly catalyzes the cyclization of AMP (see, e.g., L. B. Buck, Annual review of neuroscience 19, 517 (1996); G. M. Shepherd, Neuron 13, 771 (October, 1994); R. R. Reed, Neuron 8, 205 (February, 1992); D. Lancet, N. Ben-Arie, Curr Biol 3, 668 (Oct. 1, 1993); each herein incorporated by reference in its entirety). A rise in cytosolic cAMP triggers the activation of cAMP-gated $Ca^{2+}$ channels, ultimately resulting in membrane depolarization and action-potential generation.

While the above pathways for OR activation has been the established paradigm for OR signalling, others have proposed that some odors activate a secondary signaling pathway that involves the secondary messenger IP3, but the molecular mechanisms through which the IP3 pathway is activated is not well understood (see, e.g., K. Klasen et al., Cell Signal 22, 150 (Jan); I. Boekhoff, E. Tareilus, J. Strotmann, H. Breer, Embo J 9, 2453 (August, 1990); each herein incorporated by reference in its entirety) and is complicated by the heterogeneity of ORs.

This heterogeneity is part due to existence of a large mammalian OR repertoire: more than 350 human and 1000 mouse ORs have been identified thus far. While much is now known about the ligand specificity of other GPCRs, the odor discrimination and specificity of most ORs remain poorly characterized, despite the fact that mammalian ORs were discovered more than 15 years ago (see, e.g., L. Buck, R. Axel, Cell 65, 175 (Apr. 5, 1991); herein incorporated by reference in its entirety).

Evidence thus far suggests that odor recognition in mammals depends on complex receptor-ligand interactions that result in the activation of a repertoire of ORs expressed by defined subsets of OSNs (see, e.g., B. Malnic, J. Hirono, T. Sato, L. B. Buck, Cell 96, 713 (Mar. 5, 1999); H. Saito, Q. Chi, H. Zhuang, H. Matsunami, J. D. Mainland, Sci Signal 2, ra9 (2009); each herein incorporated by reference in its entirety). Efforts toward understanding OR-ligand interactions have been impeded by poor OR activation in heterologous cell systems. Several cofactors are now used, in combination, to improve OR activation in heterologous cells (see, e.g., P. Mombaerts, Nat Rev Neurosci 5, 263 (April, 2004); L. E. Von Dannecker, A. F. Mercadante, B. Malnic, Proc Natl Acad Sci USA 103, 9310 (Jun. 13, 2006); each herein incorporated by reference in its entirety). For example, it has been previously demonstrated that coexpressing transmembrane, olfactory-specific Receptor Transporting Proteins RTP1 and RTP2 along with ORs in HEK293T cells significantly increase the functional cell-surface expression of ORs (see, e.g., H. Saito, M. Kubota, R. W. Roberts, Q. Chi, H. Matsunami, Cell 119, 679 (Nov. 24, 2004); H. Zhuang, H. Matsunami, J Biol Chem 282, 15284 (May 18, 2007); U.S. Pat. Nos. 7,425,445, 7,838,288, 7,691, 592; U.S. Patent Application Publication Nos. 2010/0222561, 2009/0124003, 2009/0092997; each herein incorporated by reference in its entirety). ORs that are N-terminally-tagged with the first 20 amino acids of rhodopsin (Rho-tag) are frequently used in heterologous cells because Rho-tag enhances the membrane targeting of some ORs (see, e.g., D. Krautwurst, K. W. Yau, R. R. Reed, Cell 95, 917 (1998); herein incorporated by reference in its entirety).

In addition to the accessory factors mentioned above, it has been found that the cell-surface expression of one receptor, OR-M71, can be enhanced when non-OR GPCRs, including the beta2-adrenergic receptor (32AR and purinergic receptor P2Y1, are coexpressed in HEK293 cells. However, this enhancement applies only to OR-M71 and a closely related receptor, but not to other ORs (see, e.g., C. Hague et al., Proc Natl Acad Sci USA 101, 13672 (Sep. 14, 2004); C. F. Bush et al., J Biol Chem 282, 19042 (Jun. 29, 2007); each herein incorporated by reference in its entirety). These findings have led to dramatic improvements in OR activation in vitro, and more importantly, support the idea that ORs do not function alone, but require a number of accessory proteins.

While GPCR heteromerization is not well-understood, such interactions have been shown to be essential for the function of a number of GPCRs through a variety of mechanisms (see, e.g., G. Milligan, Biochim Biophys Acta 1768, 825 (April, 2007); S. C. Prinster, C. Hague, R. A. Hall, Pharmacol Rev 57, 289 (Sep. 1, 2005); each herein incorporated by reference in its entirety). For example, heteromerizaton of $GABA_BR1$ and $GABA_BR2$ is required for the proper trafficking of $GABA_B$ receptors in neurons (see, e.g., F. H. Marshall, Current Opinion in Pharmacology 1, 40 (2001); herein incorporated by reference in its entirety). In other instances, however, heteromer formation appears to regulate GPCR signaling. For example, heteromerization is required for the reciprocal modulation of beta2-adrenergic receptors (32AR and angiotensin II type 1 AT1 receptors in cardiomyocytes. When (32AR activity is blocked, the ATI receptor is functionally decoupled from Gq, independent of angiotensin binding. Conversely, when the AT1 receptor is blocked, the β2AR is decoupled from Gs, leading to the loss of downstream cAMP signaling (see, e.g., L. Luttrell, Molecular Biotechnology 39, 239 (2008); L. Barki-Harrington, L. M. Luttrell, H. A. Rockman. (2003), vol. 108, pp. 1611-1618; each herein incorporated by reference in its entirety). However, apart from several other accepted examples, the general physiological significance of GPCR heteromers has been debated in some cases (see, e.g., G. Milligan, Biochim Biophys Acta 1768, 825 (April, 2007); M. Chabre, M. le Maire, Biochemistry 44, 9395 (2005); S. AbdAlla, H. Lother, U. Quitterer, Nature 407, 94 (Sep. 7, 2000); J. L. Hansen et al., J Biol Chem 284, 1831 (Jan. 16, 2009); each herein incorporated by reference in its entirety).

Experiments conducted during the course of developing embodiments for the present invention demonstrated that the interaction of ORs with the type 3 muscarinic acetylcholine receptor M3 (see, e.g., F.-Y. Zeng, J. Wess, J. Biol. Chem. 274, 19487 (Jul. 2, 1999, 1999); herein incorporated by reference in its entirety), which is coexpressed with ORs in olfactory sensory neurons (OSNs), is important for the response of ORs to cognate odor ligands. For example, it was shown that in HEK293T cells, ORs and M3 can be coprecipitated, and coexpression of M3 increases the potency and efficacy of odor-elicited responses of a broad range of ORs. In addition, by monitoring the odor response of acutely dissociated mice OSNs, odor-dependent activation of OSNs is attenuated by M3-selective antagonists was demonstrated. In parallel, it was shown that when M3 is coexpressed, OR activation can be further enhanced by muscarinic agonists and inhibited by muscarinic antagonists in HEK293T cells. Furthermore, it was shown that M3-dependent potentiation of OR signaling is synergistic with that of RTP1S, an accessory factor required for efficient OR membrane-targeting. However, coexpression of M3 does not seem to enhance the cell-surface expression of ORs, suggesting that M3 acts through mechanism independent of RTP1, for example, by enhancing the response of ORs already at the cell surface. Finally, OR activation by cognate odors transactivates M3 in the absence of M3 agonist. The crosstalk between ORs and M3 suggests, for example, that the functional coupling of ORs and M3 is important for robust OR activation.

The identification and use of proteins involved in the modulation of OR activity (e.g., inhibition, enhancement (e.g., M3)) provides numerous research, diagnostic, drug screening, and therapeutic applications. For example, the nucleic acids and proteins of the present invention permit the selective and controllable presentation of ORs on test cells to, among other things, identify new ORs, characterize ORs, identify OR ligands, correlate olfactory responses to the molecular interactions underlying such response, identify and characterize groups of ORs and ligands responsible for olfactory responses and health conditions, and identify, select, and characterize regulators of OR response to study and control olfactory responses. The present invention, also, thus provides means for manipulating olfactory responses and the molecular basis for such response in vitro and in vivo. Numerous commercial applications are thus made possible, including the production, characterization, and use of in vitro or in vivo cell arrays expressing desired localized ORs for screening (e.g., high-throughput screening) compounds or use as synthetic olfactory systems. Any industry, including food industries, health industries, cosmetic industries, militaries, sanitary agencies, animal sniffers (e.g., for drugs, explosives, accident victims, etc.), among many others will find use of the compositions and methods of the present invention.

Accordingly, the present invention relates to polypeptides capable of modulating odorant receptor activation. In particular, the present invention provides polypeptides (e.g., type 3 muscarinic actetylcholine receptor M3) capable of enhancing odorant receptor activation. The present invention further provides assays for the detection of ligands specific for various odorant receptors. Additionally, the present invention provides methods of screening for polypeptide polymorphisms and mutations associated with odorant receptor activation (e.g., polymorphisms and mutations associated with muscarinic actetylcholine receptor polypeptides (e.g., M1, M2, M3, M4, M5)), as well as methods of screening for therapeutic agents, ligands, and modulators of such proteins.

Exemplary compositions and methods of the present invention are described in more detail in the following sections: I. Muscarinic Acetylcholine Receptor Polynucleotides; II. Muscarinic Acetylcholine Receptor Polypeptides; III. Detection of Muscarinic Acetylcholine Receptor Alleles; IV. Generation of Muscarinic Acetylcholine Receptor Antibodies; V. Gene Therapy Using Muscarinic Acetylcholine Receptor; VI. Transgenic Animals Expressing Exogenous Muscarinic Acetylcholine Receptor Genes and Homologs, Mutants, and Variants Thereof; VII. Drug Screening Using Muscarinic Acetylcholine Receptor; VIII. Pharmaceutical Compositions Containing Muscarinic Acetylcholine Receptor Nucleic Acid, Peptides, and Analogs; IX. RNAi for Muscarinic Acetylcholine Receptor; and X. Identification of Odorant Receptor Ligands.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Muscarinic Acetylcholine Receptor Polynucleotides

As described above, the present invention provides novel proteins capable of modulating odorant receptor activation. In particular, the present invention provides Muscarinic Acetylcholine Receptor genes and polypeptides (e.g., type 1 Muscarinic Acetylcholine Receptor (M1); type 2 Muscarinic Acetylcholine Receptor (M2); type 3 Muscarinic Acetylcholine Receptor (M3); type 4 Muscarinic Acetylcholine Receptor (M4), type 5 Muscarinic Acetylcholine Receptor (M5)). In some embodiments, M1, M2, M3, M4 and M5, and variants thereof, are capable of altering (e.g., inhibiting or enhancing) odorant receptor activation. In some embodiments, M3, and variants thereof, are capable of enhancing odorant receptor activation. In some embodiments, coexpression of M3 and RTP1S results in enhanced odorant receptor activation.

Accordingly, the present invention provides nucleic acids encoding muscarinic acetylcholine receptor (e.g., M1, M2, M3, M4, M5) genes, homologs, variants (e.g., polymorphisms and mutants), including but not limited to, those described in SEQ ID NOs:1-5 (see, e.g., NCBI Reference Sequences NM_001112697.1 (M1), NM_203491.2 (M2), NM_033269.4 (M3), NM_007699.2 (M4), NM_205783.2 (M5); each herein incorporated by reference in its entirety) (see, e.g., FIGS. 21-25). The present invention provides nucleic acids encoding RTP1S (SEQ ID NO: 6) (see, e.g., Gen Bank: EU070411.1; herein incorporated by reference in its entirety). Table 2 describes exemplary Muscarinic Acetylcholine Receptor and RTP genes and polypeptides of the present invention.

TABLE 2

Muscarinic Acetylcholine Receptor and RTP1S Genes and Polypeptides

| Gene | SEQ ID NO (Nucleic acid) | SEQ ID NO (Polypeptide) |
|---|---|---|
| M1 | 1 | 7 |
| M2 | 2 | 8 |
| M3 | 3 | 9 |
| M4 | 4 | 10 |
| M5 | 5 | 11 |
| RTP1S | 6 | |

In some embodiments, the present invention provides polynucleotide sequences that are capable of hybridizing to SEQ ID NOs: 1-6 under conditions of low to high stringency as long as the polynucleotide sequence capable of hybridizing encodes a protein that retains a biological activity of the naturally occurring Muscarinic Acetylcholine Receptor (M1, M2, M3, M4 and/or M5) and/or RTP1S protein. In some embodiments, the protein that retains a biological activity of a naturally occurring Muscarinic Acetylcholine Receptor (M1, M2, M3, M4 and/or M5) and/or RTP protein is 70% homologous to the wild-type Muscarinic Acetylcholine Receptor (M1, M2, M3, M4 and/or M5) and/or RTP1S, preferably 80% homologous to the wild-type Muscarinic Acetylcholine Receptor (M1, M2, M3, M4 and/or M5) and/or RTP1S, more preferably 90% homologous to the wild-type Muscarinic Acetylcholine Receptor (M1, M2, M3, M4 and/or M5) and/or RTP1S, and most preferably 95% homologous to wild-type the Muscarinic Acetylcholine Receptor (M1, M2, M3, M4 and/or M5) and/or RTP1S. In some embodiments, hybridization conditions are based on the melting temperature ($T_m$) of the nucleic acid binding complex and confer a defined "stringency" as explained above (see e.g., Wahl, et al., Meth. Enzymol., 152:399-407 (1987), incorporated herein by reference).

In other embodiments of the present invention, additional alleles of Muscarinic Acetylcholine Receptor (M1, M2, M3, M4 and/or M5) and/or RTP1S genes are provided. In some embodiments, alleles result from a polymorphism or mutation (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence. Additional examples include truncation mutations (e.g., such that the encoded mRNA does not produce a complete protein).

In still other embodiments of the present invention, the nucleotide sequences of the present invention may be engineered in order to alter a Muscarinic Acetylcholine Receptor (M1, M2, M3, M4 and/or M5) and/or RTP1S coding sequence for a variety of reasons, including but not limited to, alterations which modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of M1, M2, M3, M4 and/or M5 may be extended utilizing the nucleotide sequence in various methods known in the art to detect upstream sequences such as promoters and regulatory elements. For example, it is contemplated that restriction-site polymerase chain reaction (PCR) will find use in the present invention. This is a direct method that uses universal primers to retrieve unknown sequence adjacent to a known locus (Gobinda et al., PCR Methods Applic., 2:318-22 (1993); herein incorporated by reference in its entirety). First, genomic DNA is amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR can be used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template. In still other embodiments, walking PCR is utilized. Walking PCR is a method for targeted gene walking that permits retrieval of unknown sequence (Parker et al., Nucleic Acids Res., 19:3055-60 [1991]). The PROMOTER-FINDER kit (Clontech) uses PCR, nested primers and special libraries to "walk in" genomic DNA. This process avoids the need to screen libraries and is useful in finding intron/exon junctions.

Preferred libraries for screening for full length cDNAs include mammalian libraries that have been size-selected to include larger cDNAs. Also, random primed libraries are preferred, in that they will contain more sequences that contain the 5' and upstream gene regions. A randomly primed library may be particularly useful in case where an oligo d(T) library does not yield full-length cDNA. Genomic mammalian libraries are useful for obtaining introns and extending 5' sequence.

In other embodiments of the present invention, variants of the disclosed M1, M2, M3, M4 and/or M5 sequences are provided. In some embodiments, variants result from polymorphisms or mutations (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that it is possible to modify the structure of a peptide having a function (e.g., M1, M2, M3, M4 and/or M5 function) for such purposes as altering the biological activity (e.g., modulated M1, M2, M3, M4 and/or M5 function). Such modified peptides are considered functional equivalents of peptides having an activity of a M1, M2, M3, M4 and/or M5 peptide as defined herein. A modified peptide can be produced in which the nucleotide sequence encoding the polypeptide has been altered, such as by substitution, deletion, or addition. In some embodiments, these modifications do not significantly reduce the biological activity of the modified M1, M2, M3, M4 and/or M5 genes. In other words, construct "X" can be evaluated in order to determine whether it is a member of the genus of modified or variant M1, M2, M3, M4 and/or M5 of the present invention as defined functionally, rather than structurally. In some embodiments, the activity of variant M1, M2, M3, M4 and/or M5 polypeptides is evaluated by methods described herein (e.g., the generation of transgenic animals or the use of signaling assays).

Moreover, as described above, variant forms of M1, M2, M3, M4 and/or M5 genes are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of M1, M2, M3, M4 and/or M5 containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, 2nd ed, WH Freeman and Co., 1981). Whether a change in the amino acid sequence of a peptide results in a functional polypeptide can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter a M1, M2, M3, M4 and/or M5 coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

II. Muscarinic Acetylcholine Receptor Polypeptides

In other embodiments, the present invention provides muscarinic acetylcholine receptor (e.g., M1, M2, M3, M4, M5) polynucleotide sequences that encode muscarinic acetylcholine receptor (e.g., M1, M2, M3, M4, M5) polypeptide sequences (e.g., the polypeptides of SEQ ID NOs: 7, 8, 9, 10 and 11, respectively). In some embodiments, the present invention provides a polypeptide encoded by a nucleic acid selected from the group consisting of SEQ ID NOs: 1, 2, 3, 4 and 5 and variants thereof that are at least 80% identical to SEQ ID NOs: 1, 2, 3, 4, or 5. In further embodiments, the protein is at least 90% identical to SEQ ID NOs: 1, 2, 3, 4 or 5. In even further embodiments, the protein is at least 95% identical to SEQ ID NOs: 1, 2, 3, 4 or 5. Other embodiments of the present invention provide fragments, fusion proteins or functional equivalents of muscarinic acetylcholine receptor (e.g., M1, M2, M3, M4, M5) proteins. In some embodiments, the present invention provides mutants of muscarinic acetylcholine receptor (e.g., M1, M2, M3, M4, M5) polypeptides. In still other embodiments of the present invention, nucleic acid sequences corresponding to muscarinic acetylcholine receptor (e.g., M1, M2, M3, M4, M5) variants, homologs, and mutants may be used to generate recombinant DNA molecules that direct the expression of the muscarinic acetylcholine receptor (e.g., M1, M2, M3, M4, M5) variants, homologs, and mutants in appropriate host cells. In some embodiments of the present invention, the polypeptide may be a naturally purified product, in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be non-glycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NOs: 1-5 that encode substantially the same or a functionally equivalent amino acid sequence, may be used to clone and express muscarinic acetylcholine receptor (e.g., M1, M2, M3, M4, M5) proteins. In general, such polynucleotide sequences hybridize to one of SEQ ID NOs: 1-5 under conditions of high to medium stringency as described above. As will be understood by those of skill in the art, it may be advantageous to produce muscarinic acetylcholine receptor (e.g., M1, M2, M3, M4, M5) encoding nucleotide sequences possessing non-naturally occurring codons. Therefore, in some embodiments, codons preferred by a particular prokaryotic or eukaryotic host (Murray et al., Nucl. Acids Res., 17 [1989]) are selected, for example, to increase the rate of muscarinic acetylcholine receptor (e.g., M1, M2, M3, M4, M5) expression or to produce recombinant RNA transcripts having desirable properties, such as a longer half-life, than transcripts produced from naturally occurring sequence.

In some embodiments, muscarinic acetylcholine receptor (e.g., M1, M2, M3, M4, M5) polypeptides are used to modulate (e.g., inhibit, enhance) odorant receptor activation.

1. Vectors for Production of Muscarinic Acetylcholine Receptors (M1, M2, M3, M4, M5)

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host.

In particular, some embodiments of the present invention provide recombinant constructs comprising one or more of the sequences as broadly described above (e.g., SEQ ID NOs: 1-5). In some embodiments of the present invention, the constructs comprise a vector, such as a plasmid or viral vector, into which a sequence of the invention has been inserted, in a forward or reverse orientation. In still other embodiments, the heterologous structural sequence (e.g., SEQ ID NOs: 1-5) is assembled in appropriate phase with translation initiation and termination sequences. In some embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the E. coli lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of genes in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in E. coli).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

2. Host Cells for Production of Muscarinic Acetylcholine Receptor (e.g., M1, M2, M3, M4, M5) Polypeptides In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces*, and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), C127, 3T3, 293, 293T, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., [1989].

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

In some embodiments, the present invention provides a cell line (e.g., heterologous 293T cell lines, Hana3A cell lines) comprising coexpression of an odorant receptor (e.g., human odorant receptor, murine odorant receptor, synthetic odorant receptor) localized to the cell surface and a Muscarinic Acetylcholine Receptor (M1, M2, M3, M4, and/or M5). In some embodiments, cell lines (e.g., heterologous 293T cell lines, Hana3A cell lines) are provided comprising coexpression of an odorant receptor (e.g., human odorant receptor, murine odorant receptor, synthetic odorant receptor) localized to the cell surface and M3 so as to provide enhanced OR activation. In some embodiments, cell lines (e.g., heterologous 293T cell lines, Hana3A cell lines) are provided comprising coexpression of an odorant receptor (e.g., human odorant receptor, murine odorant receptor, synthetic odorant receptor) localized to the cell surface, M3, and a polypeptide known to assist in cell surface localization of odorant receptors (e.g., REEP polypeptides, RTP polypeptides (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety) so as to provide enhanced OR activation. In some embodiments, the polypeptide known to assist in cell surface localization of odorant receptors is any variant or wild type form of REEP and/or RTP. In some embodiments the polypeptide known to assist in cell surface localization of odorant receptors is any variant or wild type form of RTP1. In some embodiments the polypeptide known to assist in cell surface localization of odorant receptors is an RTP1S polypeptide.

In some embodiments, cell lines (e.g., heterologous 293T cell lines, Hana3A cell lines) are provided comprising coexpression of an odorant receptor (e.g., human odorant receptor, murine odorant receptor, synthetic odorant receptor) localized to the cell surface, M3, and an M3 agonist (e.g., acetylcholine, bethanechol, carbachol, oxotremorine, L-689, 660 (e.g., a mixed M1/M3 agonist), and pilocarpine) so as to provide enhanced OR activation. In some embodiments, the cells further express a polypeptide known to assist in cell surface localization of odorant receptors (e.g., REEP polypeptides, RTP polypeptides (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety). In some embodiments, the polypeptide known to assist in cell surface localization of odorant receptors is any variant or wild type form of REEP and/or RTP. In some embodiments the polypeptide known to assist in cell surface localization of odorant receptors is any variant or wild type form of RTP1. In some embodiments the polypeptide known to assist in cell surface localization of odorant receptors is an RTP1S polypeptide.

In some embodiments, cell lines (e.g., heterologous 293T cell lines, Hana3A cell lines) are provided comprising coexpression of an odorant receptor (e.g., human odorant receptor, murine odorant receptor, synthetic odorant receptor) localized to the cell surface, M3, an M3 agonist, and a polypeptide known to assist in cell surface localization of odorant receptors (e.g., REEP polypeptides, RTP polypeptides (see, e.g., U.S. Pat. Nos. 7,425,445, 7,838,288, 7,691,592; U.S. Patent Application Publication Nos. 2010/0222561, 2009/0124003, 2009/0092997; each herein incorporated by reference in its entirety) (e.g., RTP1S) so as to provide enhanced OR activation. In some embodiements, the odorant receptor is tagged with a reporting agent (e.g., glutathione-S-transferase (GST), c-myc, 6-histidine (6X-His), green fluorescent protein (GFP), maltose binding protein (MBP), influenza A virus haemagglutinin (HA), b-galactosidase, and GAL4). The cell lines are not limited to particular odorant receptors. In some embodiments, the odorant receptors expressed in the cell line include, but are not limited to, OR-S6, Olfr62, OR-EG, S6/79, S18, S46, S50, MOR23-1, MOR31-4, MOR31-6, MOR32-5 and MOR32-11. In some embodiments, cell lines expressing odorant receptors are used in the classification of an odorant receptor's functional expression (e.g., ligand specificity). In even further embodiments, cell lines expressing odorant receptors are used in the classification of an animal's olfactory sensation.

3. Purification of Muscarinic Acetylcholine Receptor (e.g., M1, M2, M3, M4, M5) Polypeptides The present invention also provides methods for recovering and purifying muscarinic acetylcholine receptor (e.g., M1, M2, M3, M4, M5) polypeptides from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In other embodiments of the present invention, protein-refolding steps can be used as necessary, in completing configuration of the mature protein. In still other embodiments of the present invention, high performance liquid chromatography (HPLC) can be employed for final purification steps.

The present invention further provides polynucleotides having a coding sequence of a muscarinic acetylcholine receptor (e.g., M1, M2, M3, M4, M5) gene (e.g., SEQ ID NOs: 1-5) fused in frame to a marker sequence that allows for purification of the polypeptide of the present invention. A non-limiting example of a marker sequence is a hexahistidine tag which may be supplied by a vector, preferably a pQE-9 vector, which provides for purification of the polypeptide fused to the marker in the case of a bacterial host, or, for example, the marker sequence may be a hemagglutinin (HA) tag when a mammalian host (e.g., COS-7 cells) is used. The HA tag corresponds to an epitope derived from the influenza hemagglutinin protein (Wilson et al., Cell, 37:767 [1984]).

4. Truncation Mutants of Muscarinic Acetylcholine Receptor (e.g., M1, M2, M3, M4, M5) Polypeptides In addition, the present invention provides fragments of muscarinic acetylcholine receptor (e.g., M1, M2, M3, M4, M5) polypeptides (i.e., truncation mutants). In some embodiments of the present invention, when expression of a portion of the muscarinic acetylcholine receptor (e.g., M1, M2, M3, M4, M5) protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751 [1987]) and *Salmonella typhimurium* and its in vitro activity has been demonstrated on recombinant proteins (Miller et al., Proc. Natl. Acad. Sci. USA 84:2718 [1990]). Therefore, removal of an N-terminal methionine, if desired, can be achieved either in vivo by expressing such recombinant polypeptides in a host which produces MAP (e.g., *E. coli* or CM89 or *S. cerivisiae*), or in vitro by use of purified MAP.

5. Fusion Proteins Containing Muscarinic Acetylcholine Receptor (e.g., M1, M2, M3, M4, M5)

The present invention also provides fusion proteins incorporating all or part of the muscarinic acetylcholine receptor (e.g., M1, M2, M3, M4, M5) polypeptides of the present invention. Accordingly, in some embodiments of the present invention, the coding sequences for the polypeptide can be incorporated as a part of a fusion gene including a nucleotide sequence encoding a different polypeptide. It is contemplated that this type of expression system will find use under conditions where it is desirable to produce an immunogenic fragment of a muscarinic acetylcholine receptor (e.g., M1, M2, M3, M4, M5) protein. In some embodiments of the present invention, the VP6 capsid protein of rotavirus is used as an immunologic carrier protein for portions of a muscarinic acetylcholine receptor (e.g., M1, M2, M3, M4, M5) polypeptide, either in the monomeric form or in the form of a viral particle. In other embodiments of the present invention, the nucleic acid sequences corresponding to the portion of a muscarinic acetylcholine receptor (e.g., M1, M2, M3, M4, M5) polypeptide against which antibodies are to be raised can be incorporated into a fusion gene construct which includes coding sequences for a late vaccinia virus structural protein to produce a set of recombinant viruses expressing fusion proteins comprising a portion of muscarinic acetylcholine receptor (e.g., M1, M2, M3, M4, M5) as part of the virion. It has been demonstrated with the use of immunogenic fusion proteins utilizing the hepatitis B surface antigen fusion proteins that recombinant hepatitis B virions can be utilized in this role as well. Similarly, in other embodiments of the present invention, chimeric constructs coding for fusion proteins containing a portion of a muscarinic acetylcholine receptor (e.g., M1, M2, M3, M4, M5) polypeptide and the poliovirus capsid protein are created to enhance immunogenicity of the set of polypeptide antigens (See e.g., EP Publication No. 025949; and Evans et al., Nature 339:385 [1989]; Huang et al., J. Virol., 62:3855 [1988]; and Schlienger et al., J. Virol., 66:2 [1992]).

In still other embodiments of the present invention, the multiple antigen peptide system for peptide-based immunization can be utilized. In this system, a desired portion of a muscarinic acetylcholine receptor (e.g., M1, M2, M3, M4, M5) is obtained directly from organo-chemical synthesis of the peptide onto an oligomeric branching lysine core (see e.g., Posnett et al., J. Biol. Chem., 263:1719 [1988]; and Nardelli et al., J. Immunol., 148:914 [1992]). In other embodiments of the present invention, antigenic determinants of the muscarinic acetylcholine receptor (e.g., M1, M2, M3, M4, M5) proteins can also be expressed and presented by bacterial cells.

In addition to utilizing fusion proteins to enhance immunogenicity, it is widely appreciated that fusion proteins can also facilitate the expression of proteins, such as a muscarinic acetylcholine receptor (e.g., M1, M2, M3, M4, M5) protein of the present invention. Accordingly, in some embodiments of the present invention, muscarinic acetylcholine receptor (e.g., M1, M2, M3, M4, M5) polypeptides can be generated as glutathione-S-transferase (i.e., GST fusion proteins). It is contemplated that such GST fusion proteins will enable easy purification of muscarinic acetylcholine receptor (e.g., M1, M2, M3, M4, M5) polypeptides, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of a muscarinic acetylcholine receptor (e.g., M1, M2, M3, M4, M5) polypeptide, can allow purification of the expressed muscarinic acetylcholine receptor (e.g., M1, M2, M3, M4, M5) fusion protein by affinity chromatography using a $Ni^{2+}$ metal resin. In still another embodiment of the present invention, the purification leader sequence can then be subsequently removed by treatment with enterokinase (See e.g., Hochuli et al., J. Chromatogr., 411:177 [1987]; and Janknecht et al., Proc. Natl. Acad. Sci. USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments can be carried out using anchor primers which give rise to complementary overhangs between two consecutive gene fragments which can subsequently be annealed to generate a chimeric gene sequence (See e.g., Current Protocols in Molecular Biology, supra).

6. Variants of Muscarinic Acetylcholine Receptors (e.g., M1, M2, M3, M4, M5)

Still other embodiments of the present invention provide mutant or variant forms of muscarinic acetylcholine receptor (e.g., M1, M2, M3, M4, M5) polypeptides (i.e., muteins). It is possible to modify the structure of a peptide having an activity of a muscarinic acetylcholine receptor (e.g., M1, M2, M3, M4, M5) polypeptide of the present invention for such purposes as enhancing therapeutic or prophylactic efficacy, disabling the protein, or stability (e.g., ex vivo shelf life, and/or resistance to proteolytic degradation in vivo). Such modified peptides are considered functional equivalents of peptides having an activity of the subject muscarinic acetylcholine receptor (e.g., M1, M2, M3, M4, M5) proteins as defined herein. A modified peptide can be produced in which the amino acid sequence has been altered, such as by amino acid substitution, deletion, or addition.

Moreover, as described above, variant forms (e.g., mutants or polymorphic sequences) of the subject muscarinic acetylcholine receptor (e.g., M1, M2, M3, M4, M5) proteins are also contemplated as being equivalent to those peptides and DNA molecules that are set forth in more detail. For example, as described above, the present invention encompasses mutant and variant proteins that contain conservative or non-conservative amino acid substitutions.

This invention further contemplates a method of generating sets of combinatorial mutants of the present muscarinic acetylcholine receptor (e.g., M1, M2, M3, M4, M5) proteins, as well as truncation mutants, and is especially useful for identifying potential variant sequences (i.e., mutants or polymorphic sequences) that are involved in neurological disorders (e.g., olfactory disorders) or resistance to neurological disorders. The purpose of screening such combinatorial libraries is to generate, for example, novel muscarinic acetylcholine receptor (e.g., M1, M2, M3, M4, M5) variants that can act as either agonists or antagonists, or alternatively, possess novel activities all together.

Therefore, in some embodiments of the present invention, muscarinic acetylcholine receptor (e.g., M1, M2, M3, M4, M5) variants are engineered by the present method to provide altered (e.g., increased or decreased) biological activity. In other embodiments of the present invention, combinatorially-derived variants are generated which have a selective potency relative to a naturally occurring muscarinic acetylcholine receptors (e.g., M1, M2, M3, M4, M5). Such proteins, when expressed from recombinant DNA constructs, can be used in gene therapy protocols.

Still other embodiments of the present invention provide muscarinic acetylcholine receptor (e.g., M1, M2, M3, M4, M5) variants that have intracellular half-lives dramatically different than the corresponding wild-type protein. For example, the altered protein can be rendered either more stable or less stable to proteolytic degradation or other cellular process that result in destruction of, or otherwise inactivate muscarinic acetylcholine receptor (e.g., M1, M2, M3, M4, M5) polypeptides. Such variants, and the genes which encode them, can be utilized to alter the location of muscarinic acetylcholine receptor (e.g., M1, M2, M3, M4, M5) expression by modulating the half-life of the protein. For instance, a short half-life can give rise to more transient muscarinic acetylcholine receptor (e.g., M1, M2, M3, M4, M5) biological effects and, when part of an inducible expression system, can allow tighter control of muscarinic acetylcholine receptor (e.g., M1, M2, M3, M4, M5) levels within the cell. As above, such proteins, and particularly their recombinant nucleic acid constructs, can be used in gene therapy protocols.

In still other embodiments of the present invention, muscarinic acetylcholine receptor (e.g., M1, M2, M3, M4, M5) variants are generated by the combinatorial approach to act as antagonists, in that they are able to interfere with the ability of the corresponding wild-type protein to regulate cell function.

In some embodiments of the combinatorial mutagenesis approach of the present invention, the amino acid sequences for a population of muscarinic acetylcholine receptor (e.g., M1, M2, M3, M4, M5) homologs, variants or other related proteins are aligned, preferably to promote the highest homology possible. Such a population of variants can include, for example, muscarinic acetylcholine receptor (e.g., M1, M2, M3, M4, M5) homologs from one or more species, or muscarinic acetylcholine receptor (e.g., M1, M2, M3, M4, M5) variants from the same species but which differ due to mutation or polymorphisms. Amino acids that appear at each position of the aligned sequences are selected to create a degenerate set of combinatorial sequences.

In a preferred embodiment of the present invention, the combinatorial muscarinic acetylcholine receptor (e.g., M1, M2, M3, M4, M5) library is produced by way of a degenerate library of genes encoding a library of polypeptides which each include at least a portion of potential muscarinic acetylcholine receptor (e.g., M1, M2, M3, M4, M5) protein sequences. For example, a mixture of synthetic oligonucleotides can be enzymatically ligated into gene sequences such that the degenerate set of potential muscarinic acetylcholine receptor (e.g., M1, M2, M3, M4, M5) sequences are expressible as individual polypeptides, or alternatively, as a set of larger fusion proteins (e.g., for phage display) containing the set of muscarinic acetylcholine receptor (e.g., M1, M2, M3, M4, M5) sequences therein.

There are many ways by which the library of potential muscarinic acetylcholine receptor (e.g., M1, M2, M3, M4, M5) homologs and variants can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential muscarinic acetylcholine receptor (e.g., M1, M2, M3, M4, M5) sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273-289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science 249:386 [1980]; Roberts et al., Proc. Natl. Acad. Sci. USA 89:2429 [1992]; Devlin et al., Science 249: 404 [1990]; Cwirla et al., Proc. Natl. Acad. Sci. USA 87: 6378 [1990]; each of which is herein incorporated by reference; as well as U.S. Pat. Nos. 5,223,409, 5,198,346, and 5,096,815; each of which is incorporated herein by reference).

It is contemplated that the muscarinic acetylcholine receptor (e.g., M1, M2, M3, M4, M5) nucleic acids of the present invention (e.g., SEQ ID NOs:1-5, and fragments and variants thereof) can be utilized as starting nucleic acids for directed evolution. These techniques can be utilized to develop muscarinic acetylcholine receptor (e.g., M1, M2, M3, M4, M5) variants having desirable properties such as increased or decreased biological activity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold, Nat. Biotech., 14, 458 [1996]; Leung et al., Technique, 1:11 [1989]; Eckert and Kunkel, PCR Methods Appl., 1:17-24 [1991]; Caldwell and Joyce, PCR Methods Appl., 2:28 [1992]; and Zhao and Arnold, Nuc. Acids. Res., 25:1307 [1997]). After mutagenesis, the resulting clones are selected for desirable activity (e.g., screened for muscarinic acetylcholine receptor (e.g., M1, M2, M3, M4, M5) activity). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith, Nature, 370: 324 [1994]; U.S. Pat. Nos. 5,837,458; 5,830,721; 5,811,238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNase treatment, the staggered extension process (STEP), and random priming in vitro recombination. In the DNase mediated method, DNA segments isolated from a pool of positive mutants are cleaved into random fragments with DNaseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer, Nature, 370:398 [1994]; Stemmer, Proc. Natl. Acad. Sci. USA, 91:10747 [1994]; Crameri et al., Nat. Biotech., 14:315 [1996]; Zhang et al., Proc. Natl. Acad. Sci. USA, 94:4504 [1997]; and Crameri et al., Nat. Biotech., 15:436 [1997]). Variants produced by directed evolution can be screened for muscarinic acetylcholine receptor (e.g., M1, M2, M3, M4, M5) activity by the methods described herein.

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis or recombination of muscarinic acetylcholine receptor (e.g., M1, M2, M3, M4, M5) homologs or variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected.

7. Chemical Synthesis of Muscarinic Acetylcholine Receptor (e.g., M1, M2, M3, M4, M5) Polypeptides In an alternate embodiment of the invention, the coding sequence of a muscarinic acetylcholine receptor (e.g., M1, M2, M3, M4, M5) is synthesized, whole or in part, using chemical methods well known in the art (See e.g., Caruthers et al., Nucl. Acids Res. Symp. Ser., 7:215 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807 [1981]). In other embodiments of the present invention, the protein itself is produced using chemical methods to synthesize either an entire muscarinic acetylcholine receptor (e.g., M1, M2, M3, M4, M5) amino acid sequence or a portion thereof. For example, peptides can be synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science 269:202 [1995]) and automated synthesis may be achieved, for example, using ABI 431A Peptide Synthesizer (Perkin Elmer) in accordance with the instructions provided by the manufacturer. Additionally, the amino acid sequence of a muscarinic acetylcholine receptor (e.g., M1, M2, M3, M4, M5) polypeptide, or any part thereof, may be altered during direct synthesis and/or combined using chemical methods with other sequences to produce a variant polypeptide.

III. Detection of Muscarinic Acetylcholine Receptor (e.g., M1, M2, M3, M4, M5) Alleles In some embodiments, the present invention provides methods of detecting the presence of wild type or variant (e.g., mutant or polymorphic) muscarinic acetylcholine receptor (e.g., M1, M2, M3, M4, M5) nucleic acids or polypeptides. The detection of mutant muscarinic acetylcholine receptor (e.g., M1, M2, M3, M4, M5) polypeptides finds use in the diagnosis of disease (e.g., olfactory disorder).

A. Detection of Variant Muscarinic Acetylcholine Receptor (e.g., M1, M2, M3, M4, M5) Alleles In some embodiments, the present invention provides alleles of a muscarinic acetylcholine receptor (e.g., M1, M2, M3, M4, M5) that increase a patient's susceptibility to olfactory disorders. Any mutation that results in an altered phenotype (e.g., diminished olfactory sensing abilility) is within the scope of the present invention.

Accordingly, the present invention provides methods for determining whether a patient has an increased susceptibility to olfactory disorders by determining, directly or indirectly, whether the individual has a variant muscarinic acetylcholine receptor (e.g., M1, M2, M3, M4, M5) allele. In other embodiments, the present invention provides methods for providing a prognosis of increased risk for olfactory disorder to an individual based on the presence or absence of one or more variant muscarinic acetylcholine receptor (e.g., M1, M2, M3, M4, M5) alleles.

A number of methods are available for analysis of variant (e.g., mutant or polymorphic) nucleic acid or polypeptide sequences. Assays for detection variants (e.g., polymorphisms or mutations) via nucleic acid analysis fall into several categories including, but not limited to, direct sequencing assays, fragment polymorphism assays, hybridization assays, and computer based data analysis. Protocols and commercially available kits or services for performing multiple variations of these assays are available. In some embodiments, assays are performed in combination or in hybrid (e.g., different reagents or technologies from several assays are combined to yield one assay). The following exemplary assays are useful in the present invention: directs sequencing assays, PCR assays, mutational analysis by dHPLC (e.g., available from Transgenomic, Omaha, Nebr. or Varian, Palo Alto, Calif.), fragment length polymorphism assays (e.g., RFLP or CFLP (See e.g. U.S. patents U.S. Pat. Nos. 5,843,654; 5,843,669; 5,719,208; and 5,888,780; each of which is herein incorporated by reference)), hybridization assays (e.g., direct detection of hybridization, detection of hybridization using DNA chip assays (See e.g., U.S. Pat. Nos. 6,045,996; 5,925,525; 5,858,659; 6,017,696; 6,068,818; 6,051,380; 6,001,311; 5,985,551; 5,474,796; PCT Publications WO 99/67641 and WO 00/39587, each of which is herein incorporated by reference), enzymatic detection of hybridization (See e.g., U.S. Pat. Nos. 5,846,717, 6,090,543; 6,001,567; 5,985,557; 5,994,069; 5,962,233; 5,538,848; 5,952,174 and 5,919,626, each of which is herein incorporated by reference)), polymorphisms detected directly or indirectly (e.g., detecting sequences (other polymorphisms) that are in linkage disequilibrium with the polymorphism to be indentified; for example, other sequences in the SPG-6 locus may be used; this method is described in U.S. Pat. No. 5,612,179 (herein incorporated by reference)) and mass spectrometry assays.

In addition, assays for the detection of variant muscarinic acetylcholine receptor (e.g., M1, M2, M3, M4, M5) proteins find use in the present invention (e.g., cell free translation methods, See e.g., U.S. Pat. No. 6,303,337, herein incorporated by reference) and antibody binding assays. The generation of antibodies that specifically recognize mutant versus wild type proteins are discussed below.

B. Kits for Analyzing Risk of Olfactory disorders

The present invention also provides kits for determining whether an individual contains a wild-type or variant (e.g., mutant or polymorphic) allele or polypeptide of a muscarinic acetylcholine receptor (e.g., M1, M2, M3, M4, M5). In some embodiments, the kits are useful determining whether the subject is at risk of developing an olfactory disorder (e.g., anosmia, hyposmia, dysomia, phantosmia, hyperosmia, olfactory agnosia, upper respiratory infections, tumors of the anterior cranial fossa, and Kallmann syndrome, Foster Kennedy syndrome, Parkinson's disease, Alzheimer's disease, Huntington chorea). The diagnostic kits are produced in a variety of ways. In some embodiments, the kits contain at least one reagent for specifically detecting a mutant muscarinic acetylcholine receptor (e.g., M1, M2, M3, M4, M5) allele or protein. In some embodiments, the reagent is a nucleic acid that hybridizes to nucleic acids containing the mutation and that does not bind to nucleic acids that do not contain the mutation. In other embodiments, the reagents are primers for amplifying the region of DNA containing the mutation. In still other embodiments, the reagents are antibodies that preferentially bind either the wild-type or mutant muscarinic acetylcholine receptor (e.g., M1, M2, M3, M4, M5) proteins.

In some embodiments, the kit contains instructions for determining whether the subject is at risk for an olfactory disorder (e.g., anosmia, hyposmia, dysomia, phantosmia, hyperosmia, olfactory agnosia, upper respiratory infections, tumors of the anterior cranial fossa, and Kallmann syndrome, Foster Kennedy syndrome, Parkinson's disease, Alzheimer's disease, Huntington chorea). In some embodiments, the instructions specify that risk for developing an olfactory disorder is determined by detecting the presence or absence of a mutant muscarinic acetylcholine receptor (e.g., M1, M2, M3, M4, M5) allele in the subject, wherein subjects having an mutant allele are at greater risk for developing an olfactory disorder.

The presence or absence of a disease-associated mutation in a muscarinic acetylcholine receptor (e.g., M1, M2, M3, M4, M5) gene can be used to make therapeutic or other medical decisions. For example, couples with a family history of odorant receptor related diseases may choose to conceive a child via in vitro fertilization and pre-implantation genetic screening. In this case, fertilized embryos are screened for mutant (e.g., disease associated) alleles of a muscarinic acetylcholine receptor (e.g., M1, M2, M3, M4, M5) gene and only embryos with wild type alleles are implanted in the uterus.

In other embodiments, in utero screening is performed on a developing fetus (e.g., amniocentesis or chorionic villi screening). In still other embodiments, genetic screening of newborn babies or very young children is performed. The early detection of a muscarinic acetylcholine receptor (e.g., M1, M2, M3, M4, M5) allele known to be associated with an olfactory disorder allows for early intervention (e.g., genetic or pharmaceutical therapies).

In some embodiments, the kits include ancillary reagents such as buffering agents, nucleic acid stabilizing reagents, protein stabilizing reagents, and signal producing systems (e.g., florescence generating systems as Fret systems). The test kit may be packaged in any suitable manner, typically with the elements in a single container or various containers as necessary along with a sheet of instructions for carrying out the test. In some embodiments, the kits also preferably include a positive control sample.

C. Bioinformatics

In some embodiments, the present invention provides methods of determining an individual's risk of developing an olfactory disorder (e.g., anosmia, hyposmia, dysomia, phantosmia, hyperosmia, olfactory agnosia, upper respiratory infections, tumors of the anterior cranial fossa, and Kallmann syndrome, Foster Kennedy syndrome, Parkinson's disease, Alzheimer's disease, Huntington chorea) based on the presence of one or more variant alleles of a muscarinic acetylcholine receptor (e.g., M1, M2, M3, M4, M5) gene. In some embodiments, the analysis of variant data is processed by a computer using information stored on a computer (e.g., in a database). For example, in some embodiments, the present invention provides a bioinformatics research system comprising a plurality of computers running a multi-platform object oriented programming language (See e.g., U.S. Pat. No. 6,125,383; herein incorporated by reference). In some embodiments, one of the computers stores genetics data (e.g., the risk of contacting an muscarinic acetylcholine receptor (e.g., M1, M2, M3, M4, M5) related olfactory disorder associated with a given polymorphism, as well as the sequences). In some embodiments, one of the computers stores application programs (e.g., for analyzing the results of detection assays). Results are then delivered to the user (e.g., via one of the computers or via the internet).

For example, in some embodiments, a computer-based analysis program is used to translate the raw data generated by the detection assay (e.g., the presence, absence, or amount of a given muscarinic acetylcholine receptor (e.g., M1, M2, M3, M4, M5) allele or polypeptide) into data of predictive value for a clinician. The clinician can access the predictive data using any suitable means. Thus, in some embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information providers, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., presence of wild type or mutant muscarinic acetylcholine receptor (e.g., M1, M2, M3, M4, M5) genes or polypeptides), specific for the diagnostic or prognostic information desired for the subject.

The profile data is then prepared in a format suitable for interpretation by a treating clinician. For example, rather than providing raw data, the prepared format may represent a diagnosis or risk assessment (e.g., likelihood of developing an muscarinic acetylcholine receptor (e.g., M1, M2, M3, M4, M5) related olfactory disorder) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the association of a given muscarinic acetylcholine receptor (e.g., M1, M2, M3, M4, M5) allele with olfactory disorders.

IV. Generation of Muscarinic Acetylcholine Receptor (e.g., M1, M2, M3, M4, M5) Antibodies The present invention provides isolated antibodies or antibody fragments (e.g., FAB fragments). Antibodies can be generated to allow for the detection of muscarinic acetylcholine receptor (e.g., M1, M2, M3, M4, M5) proteins (e.g., wild type or mutant) of the present invention. The antibodies may be prepared using various immunogens. In one embodiment, the immunogen is a human muscarinic acetylcholine receptor (e.g., M1, M2, M3, M4, M5) peptide to generate antibodies that recognize human a muscarinic acetylcholine receptor (e.g., M1, M2, M3, M4, M5). Such antibodies include, but are not limited to polyclonal, monoclonal, chimeric, single chain, Fab fragments, Fab expression libraries, or recombinant (e.g., chimeric, humanized, etc.) antibodies, as long as it can recognize the protein. Antibodies can be produced by using a protein of the present invention as the antigen according to a conventional antibody or antiserum preparation process.

Various procedures known in the art may be used for the production of polyclonal antibodies directed against a muscarinic acetylcholine receptor (e.g., M1, M2, M3, M4, M5) polypeptide. For the production of antibody, various host animals can be immunized by injection with the peptide corresponding to the muscarinic acetylcholine receptor (e.g., M1, M2, M3, M4, M5) epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward a muscarinic acetylcholine receptor (e.g., M1, M2, M3, M4, M5), it is contemplated that any technique that provides for the production of antibody molecules by continuous cell lines in culture will find use with the present invention (See e.g., Harlow and Lane, *Antibodies: A Laboratory Manual, Cold Spring Harbor Laboratory Press*, Cold Spring Harbor, N.Y.). These include but are not limited to the hybridoma technique originally developed by Köhler and Milstein (Köhler and Milstein, Nature 256:495-497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77-96 [1985]).

In an additional embodiment of the invention, monoclonal antibodies are produced in germ-free animals utilizing technology such as that described in PCT/US90/02545). Furthermore, it is contemplated that human antibodies will be generated by human hybridomas (Cote et al., Proc. Natl. Acad. Sci. USA 80:2026-2030 [1983]) or by transforming human B cells with EBV virus in vitro (Cole et al., in *Monoclonal Antibodies and Cancer Therapy*, Alan R. Liss, pp. 77-96 [1985]).

In addition, it is contemplated that techniques described for the production of single chain antibodies (U.S. Pat. No. 4,946,778; herein incorporated by reference) will find use in producing muscarinic acetylcholine receptor (e.g., M1, M2, M3, M4, M5) specific single chain antibodies. An additional embodiment of the invention utilizes the techniques described for the construction of Fab expression libraries (Huse et al., Science 246:1275-1281 [1989]) to allow rapid and easy identification of monoclonal Fab fragments with the desired specificity for a muscarinic acetylcholine receptor (e.g., M1, M2, M3, M4, M5) polypeptide.

In other embodiments, the present invention contemplated recombinant antibodies or fragments thereof to the proteins of the present invention. Recombinant antibodies include, but are not limited to, humanized and chimeric antibodies. Methods for generating recombinant antibodies are known in the art (See e.g., U.S. Pat. Nos. 6,180,370 and 6,277,969 and "Monoclonal Antibodies" H. Zola, BIOS Scientific Publishers Limited 2000. Springer-Verlay New York, Inc., New York; each of which is herein incorporated by reference).

It is contemplated that any technique suitable for producing antibody fragments will find use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody will be accomplished by techniques known in the art (e.g., radioimmunoassay, ELISA (enzyme-linked immunosorbant assay), "sandwich" immunoassays, immunoradiometric assays, gel diffusion precipitation reactions, immudiffusion assays, in situ immunoassays (e.g., using colloidal gold, enzyme or radioisotope labels), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

The foregoing antibodies can be used in methods known in the art relating to the localization and structure of a muscarinic acetylcholine receptor (e.g., M1, M2, M3, M4, M5) (e.g., for Western blotting), measuring levels thereof in appropriate biological samples, etc. The antibodies can be used to detect a muscarinic acetylcholine receptor (e.g., M1, M2, M3, M4, M5) in a biological sample from an individual. The biological sample can be a biological fluid, such as, but not limited to, blood, serum, plasma, interstitial fluid, urine, cerebrospinal fluid, and the like, containing cells.

The biological samples can then be tested directly for the presence of a human muscarinic acetylcholine receptor (e.g., M1, M2, M3, M4, M5) using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of a muscarinic acetylcholine receptor (e.g., M1, M2, M3, M4, M5) detected by immunoblotting (Western blotting). Immunoblotting techniques are generally more effective with antibodies generated against a peptide corresponding to an epitope of a protein, and hence, are particularly suited to the present invention.

Another method uses antibodies as agents to alter signal transduction. Specific antibodies that bind to the binding domains of a muscarinic acetylcholine receptor (e.g., M1, M2, M3, M4, M5) or other proteins involved in intracellular signaling can be used to inhibit the interaction between the various proteins and their interaction with other ligands. Antibodies that bind to the complex can also be used therapeutically to inhibit interactions of the protein complex in the signal transduction pathways leading to the various physiological and cellular effects of a muscarinic acetylcholine receptor (e.g., M1, M2, M3, M4, M5).

Such antibodies can also be used diagnostically to measure abnormal expression of a muscarinic acetylcholine receptor (e.g., M1, M2, M3, M4, M5), or the aberrant formation of protein complexes, which may be indicative of a disease state.

V. Gene Therapy Using Muscarinic Acetylcholine Receptors (e.g., M1, M2, M3, M4, M5)

The present invention also provides methods and compositions suitable for gene therapy to alter muscarinic acetylcholine receptor (e.g., M1, M2, M3, M4, M5) expression, production, or function for research, generation of transgenic animals, and/or therapeutic applications. In some embodiments, methods and compositions are provided suitable for gene therapy to additionally alter REEP and/or RTP (e.g., RTP1S) expression. As described above, the present invention provides human muscarinic acetylcholine receptors (e.g., M1, M2, M3, M4, M5) and/or REEP and/or RTP (e.g., RTP1) genes and provides methods of obtaining muscarinic acetylcholine receptor (e.g., M1, M2, M3, M4, M5) and/or REEP and/or RTP (e.g., RTP1) genes from other species. Thus, the methods described below are generally applicable across many species. In some embodiments, it is contemplated that the gene therapy is performed by providing a subject with a wild-type allele of a muscarinic acetylcholine receptor (e.g., M1, M2, M3, M4, M5) and/or REEP and/or RTP (e.g., RTP1S) gene (i.e., an allele that does not contain a muscarinic acetylcholine receptor (e.g., M1, M2, M3, M4, M5) and/or REEP and/or RTP (e.g., RTP1S) disease allele (e.g., free of disease causing polymorphisms or mutations)). Subjects in need of such therapy are identified by the methods described above. In some embodiments, transient or stable therapeutic nucleic acids are used (e.g., antisense oligonucleotides, siRNAs) to reduce or prevent expression of mutant proteins. In other embodiments, genes are deleted to reduce or block desired olfactory senses.

Viral vectors commonly used for in vivo or ex vivo targeting and therapy procedures are DNA-based vectors and retroviral vectors. Methods for constructing and using viral vectors are known in the art (See e.g., Miller and Rosman, BioTech., 7:980-990 [1992]). Preferably, the viral vectors are replication defective, that is, they are unable to replicate autonomously in the target cell. In general, the genome of the replication defective viral vectors that are used within the scope of the present invention lack at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Mol. Cell. Neurosci., 2:320-330 [1991]), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. (J. Clin. Invest., 90:626-630 [1992]; See also, La Salle et al., Science 259:988-990 [1993]); and a defective adeno-associated virus vector (Samulski et al., J. Virol., 61:3096-3101 [1987]; Samulski et al., J. Virol., 63:3822-3828 [1989]; and Lebkowski et al., Mol. Cell. Biol., 8:3988-3996 [1988]).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In a preferred embodiment, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, preference is given, within the scope of the present invention, to type 2 or type 5 human adenoviruses (Ad 2 or Ad 5), or adenoviruses of animal origin (See e.g., WO 94/26914). Those adenoviruses of animal origin that can be used within the scope of the present invention include adenoviruses of canine, bovine, murine (e.g., Mav1, Beard et al., Virol., 75-81 [1990]), ovine, porcine, avian, and simian (e.g., SAV) origin. Preferably, the adenovirus of animal origin is a canine adenovirus, more preferably a CAV2 adenovirus (e.g. Manhattan or A26/61 strain (ATCC VR-800)).

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In a preferred embodiment, the adenoviral vector has a deletion in the E1 region (Ad 1.0). Examples of E1-deleted adenoviruses are disclosed in EP 185,573, the contents of which are incorporated herein by reference. In another preferred embodiment, the adenoviral vector has a deletion in the E1 and E4 regions (Ad 3.0). Examples of E1/E4-deleted adenoviruses are disclosed in WO 95/02697 and WO 96/22378. In still another preferred embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al., Gene 101:195 [1991]; EP 185 573; and Graham, EMBO J., 3:2917 [1984]). In particular, they can be prepared by homologous recombination between an adenovirus and a plasmid that carries, inter alia, the DNA sequence of interest. The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al., J. Gen. Virol., 36:59 [1977]), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing any effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No. 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al., Cell 33:153 [1983]; Markowitz et al., J. Virol., 62:1120 [1988]; PCT/US95/14575; EP 453242; EP178220; Bernstein et al. Genet. Eng., 7:235 [1985]; McCormick, BioTechnol., 3:689 [1985]; WO 95/07358; and Kuo et al., Blood 82:845 [1993]). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("Rous sarcoma virus") and Friend virus. Defective retroviral vectors are also disclosed in WO 95/02697.

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and the GP+envAm-12 cell line (See, WO89/07150). In addition, the recombinant retroviral vectors can contain modifications within the LTRs for suppressing transcriptional activity as well as extensive encapsidation sequences that may include a part of the gag gene (Bender et al., J. Virol., 61:1639 [1987]). Recombinant retroviral vectors are purified by standard techniques known to those having ordinary skill in the art.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker (Feigner et. al., Proc. Natl. Acad. Sci. USA 84:7413-7417 [1987]; See also, Mackey, et al., Proc. Natl. Acad. Sci. USA 85:8027-8031 [1988]; Ulmer et al., Science 259:1745-1748 [1993]). The use of cationic lipids may promote encapsulation of negatively charged nucleic acids, and also promote fusion with negatively charged cell membranes (Feigner and Ringold, Science 337:387-388 [1989]). Particularly useful lipid compounds and compositions for transfer of nucleic acids are described in WO95/18863 and WO96/17823, and in U.S. Pat. No. 5,459,127, herein incorporated by reference.

Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce the vector in vivo as a naked DNA plasmid. Methods for formulating and administering naked DNA to mammalian muscle tissue are disclosed in U.S. Pat. Nos. 5,580,859 and 5,589,466, both of which are herein incorporated by reference.

DNA vectors for gene therapy can be introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al., J. Biol. Chem., 267:963 [1992]; Wu and Wu, J. Biol. Chem., 263:14621 [1988]; and Williams et al., Proc. Natl. Acad. Sci. USA 88:2726 [1991]). Receptor-mediated DNA delivery approaches can also be used (Curiel et al., Hum. Gene Ther., 3:147 [1992]; and Wu and Wu, J. Biol. Chem., 262:4429 [1987]).

VI. Transgenic Animals Expressing Exogenous Muscarinic Acetylcholine Receptor (e.g., M1, M2, M3, M4, M5) Genes and Homologs, Mutants, and Variants Thereof The present invention contemplates the generation of transgenic animals comprising an exogenous muscarinic acetylcholine receptor (e.g., M1, M2, M3, M4, M5) gene or homologs, mutants, or variants thereof. In some embodiments, the transgenic animals further comprise an exogenous REEP and/or RTP gene or homologs, mutants, or variants thereof (e.g., RTP1) (e.g., RTP1S). In some embodiments, the transgenic animal displays an altered phenotype as compared to wild-type animals. In some embodiments, the altered phenotype is the overexpression of mRNA for a muscarinic acetylcholine receptor (e.g., M1, M2, M3, M4, M5) and/or REEP and/or RTP (e.g., RTP1S) gene as compared to wild-type levels of muscarinic acetylcholine receptor (e.g., M1, M2, M3, M4, M5) and/or REEP and/or RTP (e.g., RTP1S) expression. In other embodiments, the altered phenotype is the decreased expression of mRNA for an endogenous muscarinic acetylcholine receptor (e.g., M1, M2, M3, M4, M5) and/or REEP and/or RTP (e.g., RTP1S) gene as compared to wild-type levels of endogenous muscarinic acetylcholine receptor (e.g., M1, M2, M3, M4, M5) and/or REEP and/or RTP (e.g., RTP1S) expression. In some embodiments, the transgenic animals comprise mutant alleles of muscarinic acetylcholine receptor (e.g., M1, M2, M3, M4, M5) and/or REEP and/or RTP (e.g., RTP1S). Methods for analyzing the presence or absence of such phenotypes include Northern blotting, mRNA protection assays, and RT-PCR. In other embodiments, the transgenic mice have a knock out mutation of a muscarinic acetylcholine receptor (e.g., M1, M2, M3, M4, M5) and/or REEP and/or RTP (e.g., RTP1S) gene. In some embodiments, the transgenic animals display an altered susceptibility to olfactory disorders (e.g., anosmia, hyposmia, dysomia, phantosmia, hyperosmia, olfactory agnosia, upper respiratory infections, tumors of the anterior cranial fossa, and Kallmann syndrome, Foster Kennedy syndrome, Parkinson's disease, Alzheimer's disease, Huntington chorea).

Such animals find use in research applications (e.g., identifying signaling pathways that a muscarinic acetylcholine receptor (e.g., M1, M2, M3, M4, M5) and/or REEP and/or RTP (e.g., RTP1S) protein is involved in), as well as drug screening applications (e.g., to screen for drugs that prevent or treat olfactory disorders). For example, in some embodiments, test compounds (e.g., a drug that is suspected of being useful to treat an olfactory disorder) are administered to the transgenic animals and control animals with a wild type muscarinic acetylcholine receptor (e.g., M1, M2, M3, M4, M5) and/or REEP and/or RTP (e.g., RTP1S) allele and the effects evaluated. The effects of the test and control compounds on disease symptoms are then assessed.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter, which allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the micro-injection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad Sci. USA 82:6927 [1985]). Transfection is easily and efficiently obtained by culturing the blastomeres on a monolayer of virus-producing cells (Van der Putten, supra; Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involves the microinjection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., mutants in which a particular domain of muscarinic acetylcholine receptor (e.g., M1, M2, M3, M4, M5) and/or REEP and/or RTP (e.g., RTP1S) is deleted). Methods for homologous recombination are described in U.S. Pat. No. 5,614,396, incorporated herein by reference.

VIII. Compound Screening Using Muscarinic Acetylcholine Receptors (e.g., M1, M2, M3, M4, M5)

In some embodiments, the isolated nucleic acid and polypeptides of Muscarinic Acetylcholine Receptors (M1, M2, M3, M4, M5) of the present invention (e.g., SEQ ID NOS: 1-5, 7-11) and related proteins and nucleic acids are used in drug screening applications for compounds that modulate (e.g., enhance or inhibit) muscarinic acetylcholine receptor (e.g., M1, M2, M3, M4, M5) activity and/or and/or odor receptor activity. The present invention further provides methods of identifying ligands and signaling pathways of the muscarinic acetylcholine receptor (e.g., M1, M2, M3, M4, M5) proteins of the present invention.

The present invention is not limited to a particular mechanism. Indeed, an understanding of the mechanism is not necessary to practice the present invention. Nonetheless, based upon OR activity experiments conducted during the course of the present invention, it is contemplated that muscarinic acetylcholine receptor (e.g., M1, M2, M3, M4, M5) family proteins function in modulator odorant receptor activity. In some embodiments, it is contemplated that M3 proteins function in the enhancement of odorant cell activity (e.g., odorant receptor activity). In some embodiments, it is contemplated that M2 and/or M4 proteins function in the inhibition of odorant cell activity (e.g., odorant receptor activity).

In some embodiments, the present invention provides methods of screening compounds for the ability to modulate (e.g., inhibit, enhance) muscarinic acetylcholine receptor (e.g., M1, M2, M3, M4, M5) activity and/or odorant receptor activity mediated by natural ligands (e.g., identified using the methods described above). Such compounds find use in the treatment of disease mediated by Muscarinic Acetylcholine Receptors (M1, M2, M3, M4, M5) (e.g., olfactory disorders), the alteration of olfactory sensory responses, and the like.

In some embodiments, the present invention provides methods of screening compounds for an ability to interact with mutant muscarinic acetylcholine receptor (e.g., M1, M2, M3, M4, M5) nucleic acid and/or mutant muscarinic acetylcholine receptor (e.g., M1, M2, M3, M4, M5) polypeptides, while simultaneously not interacting with wild type muscarinic acetylcholine receptor (e.g., M1, M2, M3, M4, M5) nucleic acid (e.g., SEQ ID NOS:1-5) and/or wild type muscarinic acetylcholine receptor (e.g., M1, M2, M3, M4, M5) polypeptides (e.g., SEQ ID NOS:7-11). Such compounds find use in the treatment of olfactory disorders facilitated by the presence of mutant forms of muscarinic acetylcholine receptor (e.g., M1, M2, M3, M4, M5) nucleic acids and/or proteins.

In some embodiments, the activity of cell surface localized ORs in cells expressing exogenous muscarinic acetylcholine receptor (e.g., M1, M2, M3, M4, M5) polypeptides is assessed in response to compounds (e.g., candidate or ligands or inhibitors).

One technique uses muscarinic acetylcholine receptor (e.g., M1, M2, M3, M4, M5) antibodies or OR antibodies, generated as discussed above. Such antibodies are capable of specifically binding to a muscarinic acetylcholine receptor (e.g., M1, M2, M3, M4, M5) or OR peptides and compete with a test compound for binding to a muscarinic acetylcholine receptor (e.g., M1, M2, M3, M4, M5) or OR peptides. Similar screens can be carried out with small molecule libraries, aptamers, etc.

The present invention contemplates the use of cell lines transfected with muscarinic acetylcholine receptor (e.g., M1, M2, M3, M4, M5) genes and variants thereof for screening compounds for activity, and in particular to high throughput screening of compounds from combinatorial libraries (e.g., libraries containing greater than $10^4$ compounds). In some embodiments, the cell lines are further transfected with REEP and/or RTP (e.g., RTP1S) genes and variants thereof. The cell lines of the present invention can be used in a variety of screening methods. In some embodiments, the cells can be used in second messenger assays that monitor signal transduction following activation of cell-surface receptors. In other embodiments, the cells can be used in reporter gene assays that monitor cellular responses at the transcription/translation level.

In second messenger assays, the host cells are preferably transfected as described above with vectors encoding muscarinic acetylcholine receptor (e.g., M1, M2, M3, M4, M5) genes or variants or mutants thereof. In some embodiments, the cell lines are further transfected with REEP and/or RTP (e.g., RTP1S) genes and variants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors or of ORs localized at the cell membrane. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75 [1996]), and plate-reading systems. In some embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

The ability of the test compound to modulate a muscarinic acetylcholine receptor (e.g., M1, M2, M3, M4, M5) binding to a compound, e.g., an odorant receptor, can also be evaluated. This can be accomplished, for example, by coupling the compound, e.g., the substrate, with a radioisotope or enzymatic label such that binding of the compound, e.g., the substrate, to muscarinic acetylcholine receptor (e.g., M1, M2, M3, M4, M5) can be determined by detecting the labeled compound, e.g., substrate, in a complex.

Alternatively, a muscarinic acetylcholine receptor (e.g., M1, M2, M3, M4, M5) is coupled with a radioisotope or enzymatic label to monitor the ability of a test compound to modulate muscarinic acetylcholine receptor (e.g., M1, M2, M3, M4, M5) binding to a muscarinic acetylcholine receptor (e.g., M1, M2, M3, M4, M5) substrate in a complex. For example, compounds (e.g., substrates) can be labeled with $^{125}I$, $^{35}S$ $^{14}C$ or $^3H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., an odorant receptor) to interact with a muscarinic acetylcholine receptor (e.g., M1, M2, M3, M4, M5) with or without the labeling of any of the interactants can be evaluated. For example, a microphysiometer can be used to detect the interaction of a compound with a muscarinic acetylcholine receptor (e.g., M1, M2, M3, M4, M5) without the labeling of either the compound or the muscarinic acetylcholine receptor (e.g., M1, M2, M3, M4, M5) (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and a muscarinic acetylcholine receptor (e.g., M1, M2, M3, M4, M5) polypeptide.

In yet another embodiment, a cell-free assay is provided in which a muscarinic acetylcholine receptor (e.g., M1, M2, M3, M4, M5) protein or biologically active portion thereof is contacted with a test compound and the ability of the test compound to bind to the muscarinic acetylcholine receptor (e.g., M1, M2, M3, M4, M5) protein or biologically active portion thereof is evaluated. Preferred biologically active portions of muscarinic acetylcholine receptor (e.g., M1, M2, M3, M4, M5) proteins to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in 1 5 the assay should be maximal. An FRET binding event can be conveniently measured through standard fluorometric detection means well known in the art (e.g., using a fluorimeter).

Modulators of muscarinic acetylcholine receptor (e.g., M1, M2, M3, M4, M5) expression can also be identified. For example, a cell or cell free mixture is contacted with a candidate compound and the expression of muscarinic acetylcholine receptor (e.g., M1, M2, M3, M4, M5) mRNA or protein evaluated relative to the level of expression of the muscarinic acetylcholine receptor (e.g., M1, M2, M3, M4, M5) mRNA or protein in the absence of the candidate compound. When expression of the muscarinic acetylcholine receptor (e.g., M1, M2, M3, M4, M5) mRNA or protein is greater in the presence of the candidate compound than in its absence, the candidate compound is identified as a stimulator of a muscarinic acetylcholine receptor (e.g., M1, M2, M3, M4, M5) mRNA or protein expression. Alternatively, when expression of muscarinic acetylcholine receptor (e.g., M1, M2, M3, M4, M5) mRNA or protein is less (i.e., statistically significantly less) in the presence of the candidate compound than in its absence, the candidate compound is identified as an inhibitor of muscarinic acetylcholine receptor (e.g., M1, M2, M3, M4, M5) mRNA or protein expression. The level of muscarinic acetylcholine receptor (e.g., M1, M2, M3, M4, M5) mRNA or protein expression can be determined by methods described herein for detecting muscarinic acetylcholine receptor (e.g., M1, M2, M3, M4, M5) mRNA or protein.

A modulating agent can be identified using a cell-based or a cell free assay, and the ability of the agent to modulate the activity of a muscarinic acetylcholine receptor (e.g., M1, M2, M3, M4, M5) protein can be confirmed in vivo, e.g., in an animal such as an animal model for a disease (e.g., an animal with an muscarinic acetylcholine receptor (e.g., M1, M2, M3, M4, M5) related olfactory disorder).

B. Therapeutic Agents

This invention further pertains to novel agents identified by the above-described screening assays. Accordingly, it is within the scope of this invention to further use an agent identified as described herein (e.g., a muscarinic acetylcholine receptor (e.g., M1, M2, M3, M4, M5) modulating agent or mimetic, a muscarinic acetylcholine receptor (e.g., M1, M2, M3, M4, M5) specific antibody, a muscarinic acetylcholine receptor (e.g., M1, M2, M3, M4, M5)—binding partner, or an OR agonist or inhibitor) in an appropriate animal model (such as those described herein) to determine the efficacy, toxicity, side effects, or mechanism of action, of treatment with such an agent. Furthermore, as described above, novel agents identified by the above-described screening assays can be, e.g., used for treatments of olfactory disorders (e.g., including, but not limited to, olfactory disorders).

VIII. Pharmaceutical Compositions Containing Muscarinic Acetylcholine Receptor (e.g., M1, M2, M3, M4, M5) Nucleic Acid, Peptides, and Analogs The present invention further provides pharmaceutical compositions which may comprise all or portions of muscarinic acetylcholine receptor (e.g., M1, M2, M3, M4, M5) polynucleotide sequences, muscarinic acetylcholine receptor (e.g., M1, M2, M3, M4, M5) polypeptides, inhibitors or antagonists of muscarinic acetylcholine receptor (e.g., M1, M2, M3, M4, M5) bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by mutant muscarinic acetylcholine receptor (e.g., M1, M2, M3, M4, M5) alleles (e.g., anosmia, hyposmia, dysomia, phantosmia, hyperosmia, olfactory agnosia, upper respiratory infections, tumors of the anterior cranial fossa, and Kallmann syndrome, Foster Kennedy syndrome, Parkinson's disease, Alzheimer's disease, Huntington chorea). Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, muscarinic acetylcholine receptor (e.g., M1, M2, M3, M4, M5) nucleotide and muscarinic acetylcholine receptor (e.g., M1, M2, M3, M4, M5) amino acid sequences can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert. In another embodiment of the present invention, muscarinic acetylcholine receptor (e.g., M1, M2, M3, M4, M5) polynucleotide sequences or muscarinic acetylcholine receptor (e.g., M1, M2, M3, M4, M5) amino acid sequences may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of a muscarinic acetylcholine receptor (e.g., M1, M2, M3, M4, M5) may be that amount that suppresses olfactory disorder related symptoms. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of a muscarinic acetylcholine receptor (e.g., M1, M2, M3, M4, M5), conditions indicated on the label may include treatment of condition related to olfactory disorders.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts muscarinic acetylcholine receptor (e.g., M1, M2, M3, M4, M5) levels.

A therapeutically effective dose refers to that amount of a muscarinic acetylcholine receptor (e.g., M1, M2, M3, M4, M5) that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.01 to 100,000 micrograms, up to a total dose of about 1 g, depending upon the route of administration. Guidance as to particular dosages and methods of delivery is provided in the literature (See, U.S. Pat. Nos. 4,657,760; 5,206,344; or 5,225,212, all of which are herein incorporated by reference). Those skilled in the art will employ different formulations for a muscarinic acetylcholine receptors (e.g., M1, M2, M3, M4, M5) than for the inhibitors of muscarinic acetylcholine receptor (e.g., M1, M2, M3, M4, M5). Administration to the bone marrow may necessitate delivery in a manner different from intravenous injections.

IX. RNAi for Muscarinic Acetylcholine Receptors (e.g., M1, M2, M3, M4, M5)

RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

As discussed above, the present invention provides RNAi for inhibiting the expression of the muscarinic acetylcholine receptor (e.g., M1, M2, M3, M4, M5) polypeptide in cells, ORs, or pathway components involved in the expression or activity of such components.

A. Designing and Testing RNAi for Muscarinic Acetylcholine Receptor (e.g., M1, M2, M3, M4, M5)

In order to design siRNAs for muscarinic acetylcholine receptors (e.g., M1, M2, M3, M4, M5) (e.g. that target muscarinic acetylcholine receptor (e.g., M1, M2, M3, M4, M5) mRNA) software design tools are available in the art (e.g. on the Internet). For example, Oligoengine's web page has one such design tool that finds RNAi candidates based on Elbashir's (Elbashir et al, Methods 2002; 26: 199-213, herein incorporated by reference) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously.

siRNA candidate molecules that are generated can be, for example, screened in an animal model of an olfactory disorder for the quantitative evaluation of muscarinic acetylcholine receptor (e.g., M1, M2, M3, M4, M5) expression in vivo using similar techniques as described above.

B. Expression Cassettes

Muscarinic acetylcholine receptor (e.g., M1, M2, M3, M4, M5) specific siRNAs of the present invention may be synthesized chemically. Chemical synthesis can be achieved by any method known or discovered in the art. Alternatively, muscarinic acetylcholine receptor (e.g., M1, M2, M3, M4, M5) specific siRNAs of the present invention may be synthesized by methods which comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex siRNA, where the two strands are synthesized separately and annealed, can also be synthesized chemically by any method known or discovered in the art. Alternatively, ds siRNA are synthesized by methods that comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA specific for muscarinic acetylcholine receptors (e.g., M1, M2, M3, M4, M5). In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. The term "gene" in the expression cassette refers to a nucleic acid sequence that comprises coding sequences necessary for the production of a siRNA. Thus, a gene includes but is not limited to coding sequences for a strand of a ds siRNA.

Generally, a DNA expression cassette comprises a chemically synthesized or recombinant DNA molecule containing at least one gene, or desired coding sequence for a single strand of a ds siRNA, and appropriate nucleic acid sequences necessary for the expression of the operably linked coding sequence, either in vitro or in vivo. Expression in vitro may include expression in transcription systems and in transcription/translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the eye), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

C. Vectors

In other aspects of the present invention, the compositions comprise a vector comprising a gene encoding an siRNA specific for a muscarinic acetylcholine receptor (e.g., M1, M2, M3, M4, M5) or preferably at least one expression cassette comprising a promoter and a gene which encodes a sequence necessary for the production of a siRNA specific for a muscarinic acetylcholine receptor (e.g., M1, M2, M3, M4, M5) (an siRNA gene). The vectors may further comprise marker genes, reporter genes, selection genes, or genes of interest, such as experimental genes. Vectors of the present invention include cloning vectors and expression vectors. Expression vectors may be used in in vitro transcription/translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, OC (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising a siRNA gene (specific for a muscarinic acetylcholine receptor (e.g., M1, M2, M3, M4, M5)) is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Enhancers useful in the present invention include, but are not limited to, a cytomegalovirus early promoter enhancer, the polyoma enhancer on the late side of the replication origin, and adenovirus enhancers.

Preferably the design of a vector is configured to deliver the RNAi for more permanent inhibition. For example the pSilencer siRNA expression vector offered by Ambion, the pSuper RNAi system offered by Oligoengine, and the Gne-Silencer System offered by IMGENEX. These are all plasmid vector based RNAis. BD Biosciences offer the RNAi-Ready pSIREN Vectors, that allow both a Plasmid-based vectors and an Adenoviral or a Retroviral delivery formats. Ambion is expected to release an adenoviral vector for siRNA shortly. For the design of a vector there is no limitation regarding the folding pattern since there is no concern regarding the formation of a hairpin or at least there are no studies that found any difference in performance related to the mRNA folding pattern. Therefore, SEQ ID NOS: 1-5, for example, may be used with in a Vector (both Plasmid and Viral) delivery systems.

It is noted that Ambion offers a design tool for a vector on their web page, and BD Biosciences offers a manual for the design of a vector, both of which are useful for designing vectors for siRNA.

D. Transfecting Cells

In yet other aspects, the present invention provides compositions comprising cells transfected by an expression cassette of the present invention as described above, or by a vector of the present invention, where the vector comprises an expression cassette (or simply the siRNA gene) of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, 293T, C127, 3T3, HeLa, and BHK cell lines. Specific examples of host cells in vivo include tumor tissue and eye tissue.

The cells may be transfected transiently or stably (e.g. DNA expressing the siRNA is stably integrated and expressed by the host cell's genome). The cells may also be transfected with an expression cassette of the present invention, or they are transfected with an expression vector of the present invention. In some embodiments, transfected cells are cultured mammalian cells, preferably human cells. In other embodiments, they are tissue, organ, or organismal cells.

In the present invention, cells to be transfected in vitro are typically cultured prior to transfection according to methods which are well known in the art, as for example by the preferred methods as defined by the American Tissue Culture Collection. In certain embodiments of the present invention, cells are transfected with siRNAs that are synthesized exogenously (or in vitro, as by chemical methods or in vitro transcription methods), or they are transfected with expression cassettes or vectors, which express siRNAs within the transfected cell.

In some embodiments, cells are transfected with siRNAs by any method known or discovered in the art which allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498, herein incorporated by reference).

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267:963; Wu and Wu (1988) J. Biol. Chem., 263: 14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429). In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127, herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In some embodiments, the transfecting agent is OLIGO-FECTAMINE. OLIGOFECTAMINE is a lipid based transfection reagent. Additional example of lipid based transfection reagents that were designed for the transfection of dsRNAis are the Transit-TKO reagent which is provided by Mirus (Madison, Wis.) and the jetSI which was introduced by Polyplus-trasfection SAS. In addition, the Silencer siRNA Transfection Kit provided by Ambion's includes siPORT Amine and siPORT Lipid transfection agents. Roche offers the Fugene 6 transfection reagents that are also lipid based. There is an option to use electroporation in cell culture. Preferably a plasmid vector delivery system is transfected into the cell with OLIGOFECTAMINE provided by Invitrogen or with siPORT XP-1 transfection agent provided by Ambion.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

E. Kits

The present invention also provides kits comprising at least one expression cassette comprising a siRNA gene specific for a muscarinic acetylcholine receptor (e.g., M1, M2, M3, M4, M5). In some aspects, a transcript from the expression cassette forms a double stranded siRNA of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a siRNA gene, such that at least one gene encodes one strand of a siRNA that combines with a strand encoded by a second cassette to form a ds siRNA; the ds siRNA so produced is any of the embodiments described above. These cassettes may comprise a promoter and a sequence encoding one strand of a ds siRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a ds siRNA and a processing site between the sequences encoding each strand such that, when the gene is transcribed, the transcript is processed, such as by cleavage, to result in two separate strands which can combine to form a ds siRNA, as described above.

In some embodiments, the present invention provides kits comprising; a) a composition comprising small interfering RNA duplexes (siRNAs) configured to inhibit expression of the muscarinic acetylcholine receptor (e.g., M1, M2, M3, M4, M5) protein, and b) printed material with instructions for employing the composition for treating a target cell expressing a muscarinic acetylcholine receptor (e.g., M1, M2, M3, M4, M5) protein via expression of a muscarinic acetylcholine receptor (e.g., M1, M2, M3, M4, M5) mRNA under conditions such that the muscarinic acetylcholine receptor (e.g., M1, M2, M3, M4, M5) mRNA is cleaved or otherwise disabled. In certain embodiments, the printed material comprises instructions for employing the composition for treating eye disease.

F. Generating Muscarinic Acetylcholine Receptor (e.g., M1, M2, M3, M4, M5) Specific siRNA The present invention also provides methods of synthesizing siRNAs specific for muscarinic acetylcholine receptor (e.g., M1, M2, M3, M4, M5) (e.g. human muscarinic acetylcholine receptors (e.g., M1, M2, M3, M4, M5)) or specific for mutant or wild type forms of muscarinic acetylcholine receptors (e.g., M1, M2, M3, M4, M5). The siRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells. Therefore, the present invention also provides methods of transfecting host cells with siRNAs synthesized in vitro; in particular embodiments, the siRNAs are synthesized by in vitro transcription. The present invention further provides methods of silencing the muscarinic acetylcholine receptor (e.g., M1, M2, M3, M4, M5) gene in vivo by transfecting cells with siRNAs synthesized in vitro. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors which direct synthesis of siRNAs in vivo. The present invention also provides methods of silencing genes in vivo by transfecting cells with expression cassettes or vectors that direct synthesis of siRNAs in vivo.

X. Identification of Odorant Receptor Ligands

The present invention provides methods for identifying ligands specific for odorant receptors. The present invention is not limited to a particular method for indentifying ligands specific for odorant receptors. In some embodiments, the present invention provides a cell line (e.g., heterologous 293T cell line) expressing an odorant receptor of interest (e.g., any human odorant receptor) localized to the cell surface, and one or more Muscarinic Acetylcholine Receptors (M1, M2, M3, M4, M5). In some embodiments, the Muscarinic Acetylcholine Receptor is M3. In some embodiments, the cell lines further express RTP1S. In some embodiments, the cell lines further have an M3 agonist. Activation of an odorant receptor results in an increase in cAMP. As such, in some embodiments, the cell line further comprises a cAMP responsive element linked with a reporting agent (e.g., luciferase) for detecting odorant receptor activation. An odiferous molecule is exposed to the cell line. If the odiferous molecule is a ligand specific for the odorant receptor, luciferase expression or a change in luciferase expression is detectable.

EXAMPLES

The following examples are provided to demonstrate and further illustrate certain some embodiments of the present invention and are not to be construed as limiting the scope thereof.

Example I

This example shows that coexpression of a non-OR GPCR increases OR activation. To identify a non-OR GPCR that interacts with ORs and modulates OR signaling, potential receptors were screened from a candidate library that consists of non-chemosensory GPCRs previously shown to be expressed in the olfactory epithelium using quantitative RT-PCR analysis (see, e.g., J. B. Regard, I. T. Sato, S. R. Coughlin, Cell 135, 561 (Oct. 31, 2008); herein incorporated by reference in its entirety). To determine whether the expression of these GPCRs affect the function of ORs, each of the GPCRs were coexpressed with one of three untagged (FIGS. 1A, 1B and 1C) or N-terminal rhodopsin tagged (Rho-tagged) (FIG. 1D, 1E, 1F) ORs: OR-S6 (FIG. 1A and FIG. 1D), OR-EG (FIGS. 1B and 1E), and Olfr62 (FIGS. 1C and 1F) in HEK293T cells in the presence of OR-trafficking proteins RTP1S and an olfactory GTP/GDP exchange factor Ric-8b (see, e.g., L. E. Von Dannecker, A. F. Mercadante, B. Malnic, Proc Natl Acad Sci USA 103, 9310 (Jun. 13, 2006); H. Saito, M. Kubota, R. W. Roberts, Q. Chi, H. Matsunami, Cell 119, 679 (Nov. 24, 2004); H. Zhuang, H. Matsunami, J Biol Chem 282, 15284 (May 18, 2007); each herein incorporated by reference in its entirety). These OR-expressing cells were next stimulated with cognate odors and the activation of the ORs measured using a cAMP-response element (CRE)-based luciferase reporter system that quantifies OR activation based on cAMP production (see, e.g., H. Saito, M. Kubota, R. W. Roberts, Q. Chi, H. Matsunami, Cell 119, 679 (Nov. 24, 2004); H. Zhuang, H. Matsunami, J Biol Chem 282, 15284 (May 18, 2007); S. Katada, T. Nakagawa, H. Kataoka, K. Touhara, Biochem Biophys Res Commun 305, 964 (Jun. 13, 2003); H. Zhuang, H. Matsunami, Nat Protoc 3, 1402 (2008); each herein incorporated by reference in its entirety). Of the 22 GPCRs that were cloned and tested (see Table 1), coexpression of a number of these GPCRs increased OR response upon odor stimulation in each of the three receptors tested (T-test, $p<0.05$ after Bonferroni correction) (see FIGS. 1A-1F). Of these, only the type 3 muscarinic acetylcholine receptor (M3) consistently increased the response of all untagged (FIGS. 1A-C) and tagged (FIG. 1D-F) receptors tested. Similar results were obtained using Hana3A cells, which are HEK293T-derived cells that stably express the previously identified accessory factors (see FIG. 2) (see, e.g. H. Saito, M. Kubota, R. W. Roberts, Q. Chi, H. Matsunami, Cell 119, 679 (Nov. 24, 2004); herein incorporated by reference in its entirety).

TABLE 1

Listed in the order as presented in FIG. 1 are the full names of the 22 GPCRs tested in the luciferase assay screen for OR potentiation. The numbered items correspond to each acronym as shown in FIG. 1.

1. mammalian expression vector PCI
2. adenosine $A_{2B}$ receptor
3. alpha-2A adrenergic receptor
4. beta-2 adrenergic receptor
5. muscarinic acetylcholine receptor 3
6. cysteinyl leukotriene receptor 1
7. GPR126
8. dopamine receptor D2
9. sphingosine-1-phosphate receptor 1
10. protease-activated receptor
11. frizzled receptor 1
12. frizzled receptor 3
13. frizzled receptor 6
14. frizzled receptor 7
15. lung seven transmembrane receptor 2
16. 5-hydroxytryptamine receptors
17. interleukin 8 receptor, beta
18. purinergic P2Y receptor, G-Protein Coupled 1
19. purinergic P2Y receptor, G-Protein Coupled 2
20. lysophosphatidic acid receptor 6/purinergic P2Y receptor, G-Protein Coupled 5
21. GABA B-like receptor
22. prostaglandin E2 receptor
23. tachikinin receptor 1

Muscarinic acetylcholine receptors, like mammalian ORs, are also class A GPCRs, and are known to function in a number of physiological processes. To understand the role of all muscarinic acetylcholine receptors in OR activity, the five muscarinic receptor family members with the three ORs were tested using the luciferase assay described above. It was found that whereas the odd, Gq-coupled subfamily members M1, M3 and M5 enhanced the activation of the ORs, the even, $G_i$-coupled subfamily members M2 and M4 inhibited the function of the ORs (see FIG. 3).

Example II

This example demonstrates that M3 is expressed in olfactory sensory neurons (OSNs). To determine whether M3 is expressed by olfactory sensory neurons (OSNs), mRNA in situ hybridizations were performed on sections of the olfactory epithelium. It was found that M3 is expressed in the OSNs, which can be distinguished as the cell population that strongly expresses the Olfactory Marker Protein (OMP) (FIG. 4A, 4B, 4C). Furthermore, immunostaining was performed on sections of the olfactory epithelium to assess whether M3 protein expression patterns are colocalize with the olfactory cilia where ORs are localized. Consistent with the idea that M3 plays an important role in olfactory signaling, M3 signal was localized at the cilia in the olfactory epithelium, with similar localization as adenylyl cyclase III (FIG. 4D, 4E, 4F, 4G). In marked contrast, M1 and M5, as well as M2, were not well-expressed at the olfactory cilia (FIG. 4E, 4F) (see, also, FIG. 5). While not limited to a particular mechanism, while all three odd-membered muscarinic receptors potentiate OR signaling, only M3 is expressed, suggesting, for example, that M1 and M5 do not have a role in OR potentiation, and that the effect observed with M1 and M5 may, for example, be a result of the high sequence homology among the subfamily members (>60% homologous).

Example III

This example shows that M3 enhances the function of wide variety of mammalian ORs. M3 was coexpressed with a large set mouse and human ORs for which ligands have been identified. A diverse set of Rho-tagged ORs was expressed, as well as previously known accessory factor RTP1S in HEK293T cells either with or without M3. In each case, it was observed that M3 enhanced the activation of ORs upon ligand stimulation, either by lowering the EC50 value and/or increasing maximal OR response (FIG. 6A-??). The degree of enhancement was OR-dependent, though greater relative enhancement was observed when M3 was coexpressed with ORs that showed weaker odor responses without M3. That M3 interacts with a large number of diverse ORs further supports the idea that M3 is physiologically important for olfactory signaling.

Example IV

This example shows that potentiation of ORs by M3 is modulated by muscarinic agonist and antagonist in heterologous cells. Given that GPCRs that form heteromeric interactions often show functional co-modulation, experiments were conducted to determine if altering M3 activity directly affects the odor-mediated activation of ORs. To address this question, M3 and OR-S6 were coexpressed in HEK293T cells and stimulated with nonanedioic acid (OR-S6 ligand) in the presence of either carbachol (muscarinic agonist) or atropine (muscarinic antagonist). Carbachol alone did not induce the reporter gene expression at the concentration tested ($10^{-7}$M) (FIG. 7). Co-stimulation with carbachol further enhanced OR-S6 activation. Conversely, the presence of atropine hindered the potentiation effect of M3 (FIG. 8). This effect was only observed in the presence of M3, consistent with the idea that the activation state of M3 is an important factor in determining M3's effect on OR signaling.

Example V

Figure 9A:
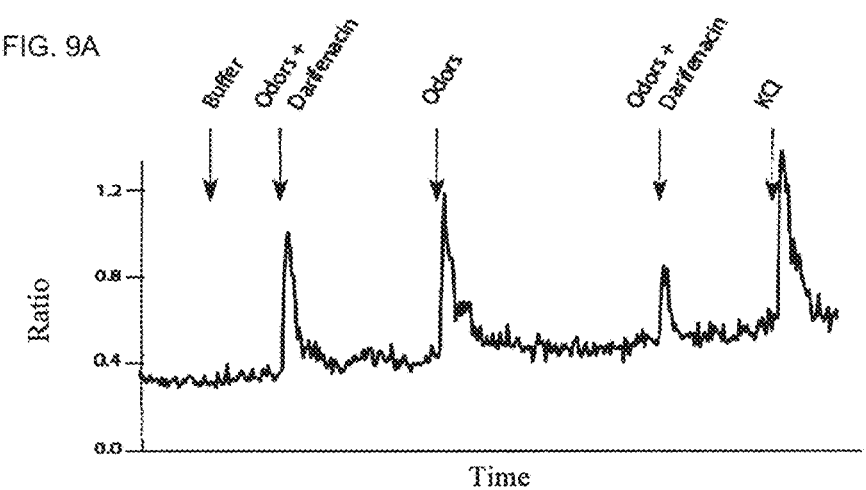
FIGS. 9A-D show that M3-selective antagonist darifenecin and pfHHSiD attenuate odor-mediated responses of OSNs.
Figure 9B:
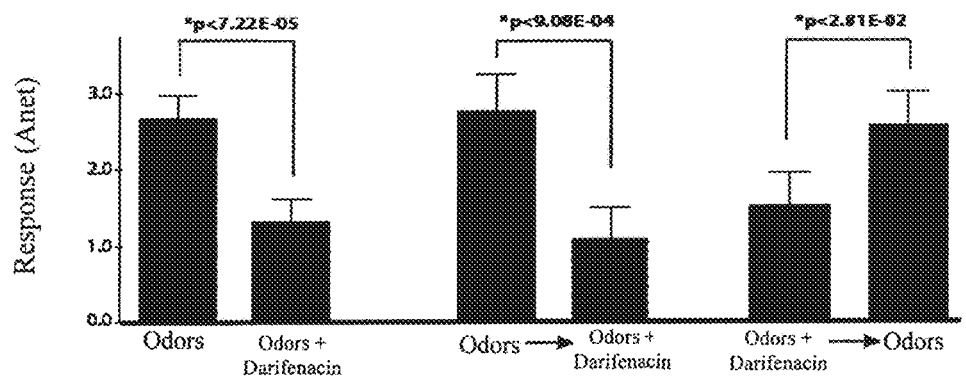
Figure 9C:
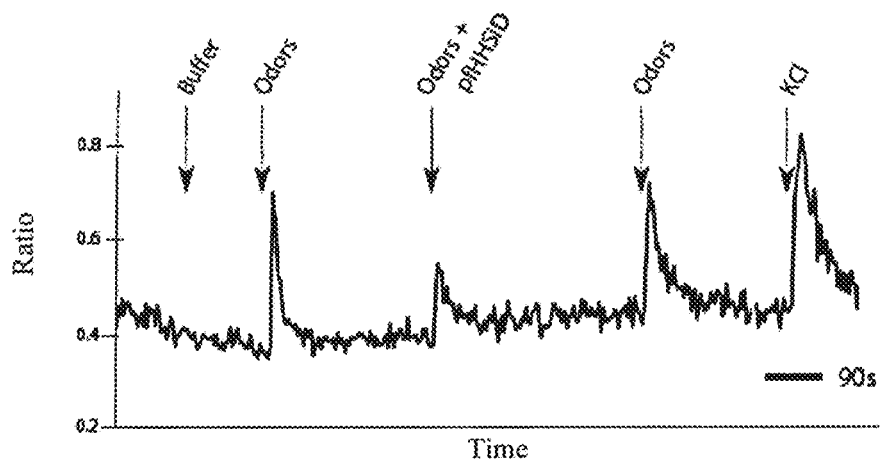
Figure 9D:
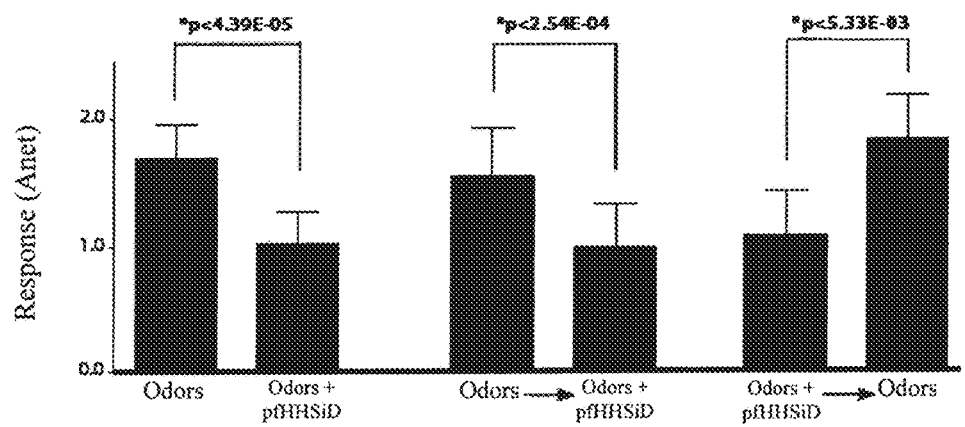
Figure 10A:
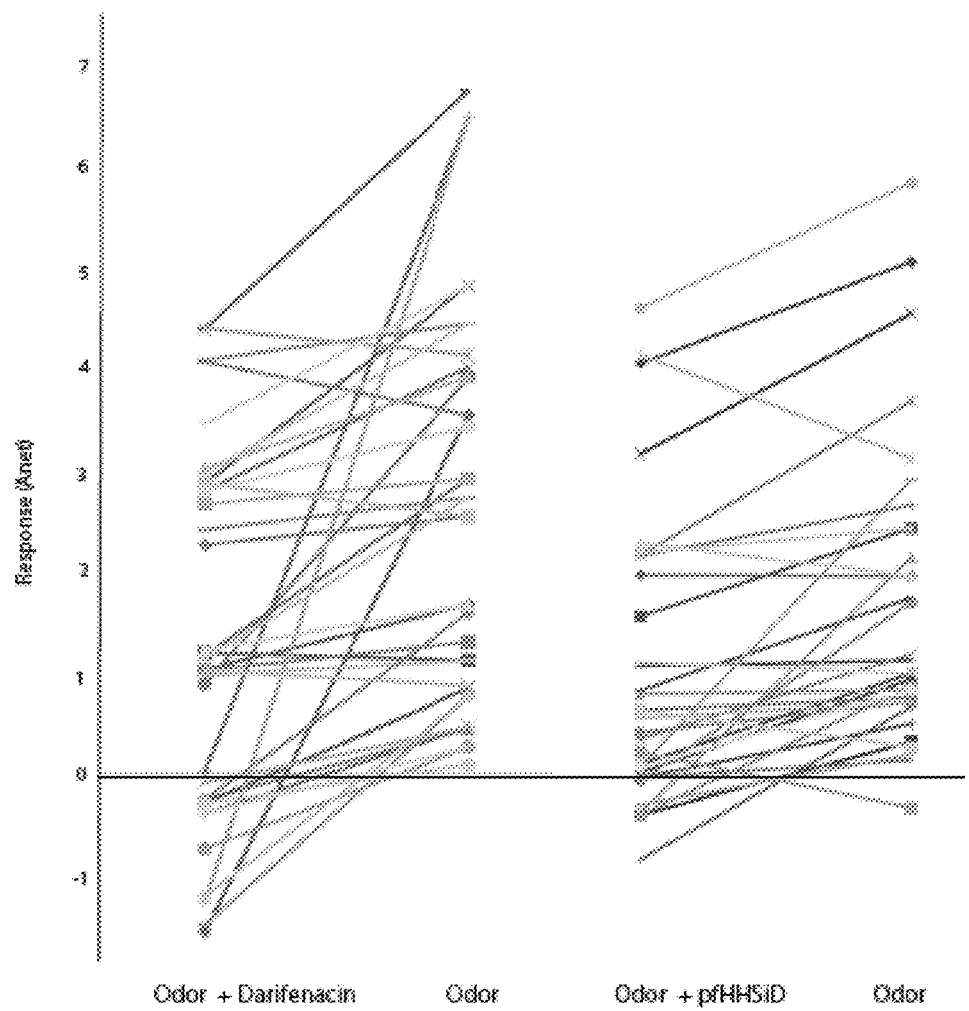
FIGS. 10A-B show detailed response curves and response values of OSN. Each paired recording of OSN responses used for statistical analysis in FIG. 9 are shown as FIG. 10A: single neuron response profiles
Figure 10B:
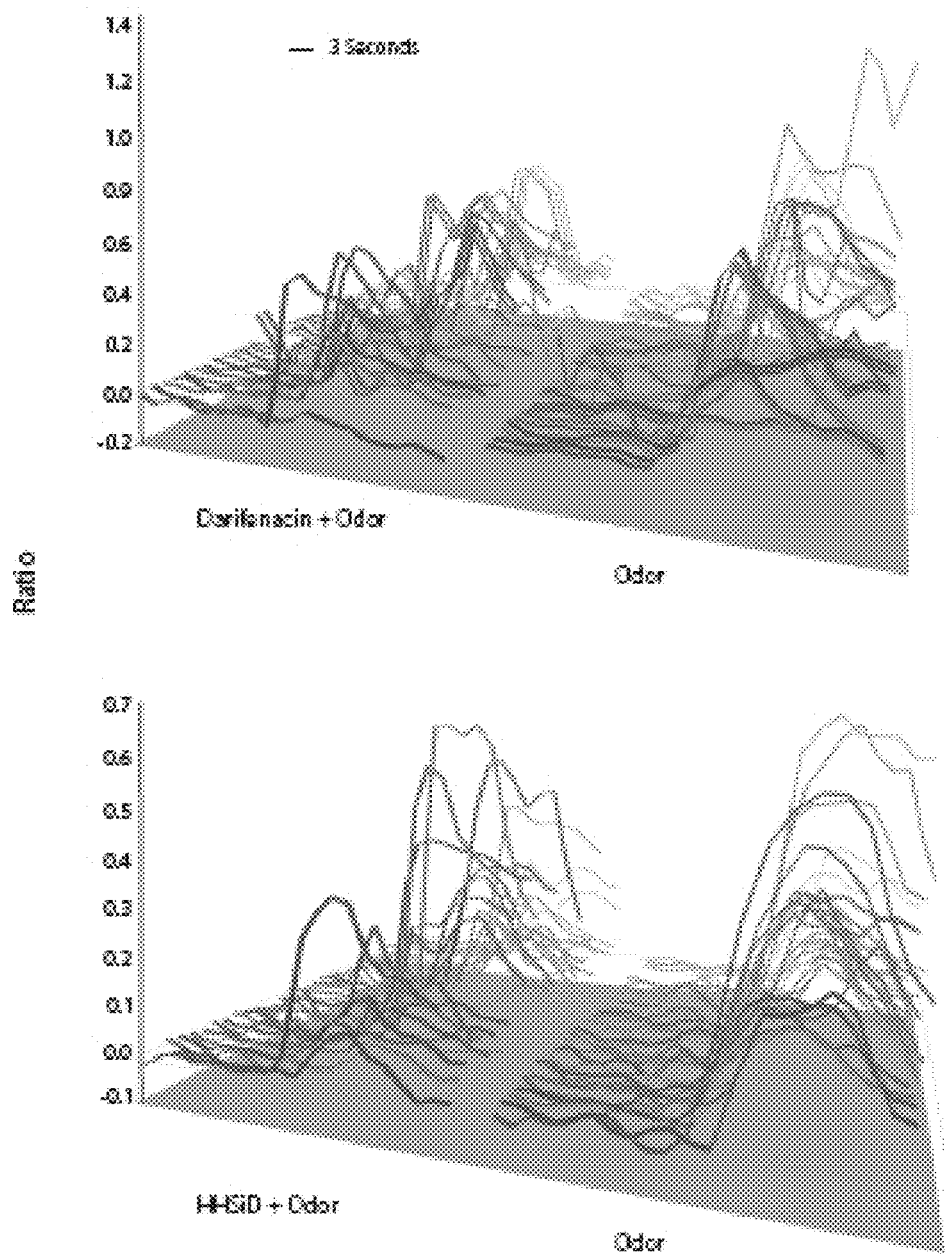

This example shows that M3-selective agonists attenuate the OSN activation. If the state of M3 activation influences odor response as a result of direct receptor-receptor interaction in vivo, then it is likely that M3 antagonists will inhibit the activation of OSNs. Because odor stimulation of OSNs leads to transient increases in intracellular calcium, calcium imaging analysis was used to monitor OSNs activation. Comparisons were made between responses of individual, acutely-dissociated OSNs from mice to either a mixture of 10 odorants or the same mixture containing either darifenacin and pfHHSiD, two different M3-selective antagonists. When OSNs were stimulated with odors containing darifenacin, the calcium responses of each OSN that responded to the odors were significantly attenuated (FIGS. 9 and 10). The decrease was independent of the sequence of the stimulation, as administering the odor mixture or the odor mixture plus darifenacin first yielded similar results (FIG. 9B). Consistent with observations made in heterologous cells (FIG. 6), the degree of inhibition was different in different neurons that were assumed to express different ORs (FIG. 10). Equivalent results were observed using pfHHSiD, another M3-selective antagonist (FIGS. 9C and 9D, and FIG. 10). While not limited to a particular mechanism, together, these results support the idea that, for example, M3 enhances the function of ORs and that the state of M3 activation affects the odor-mediated activation of ORs in OSNs.

Example VI

Figure 11A:
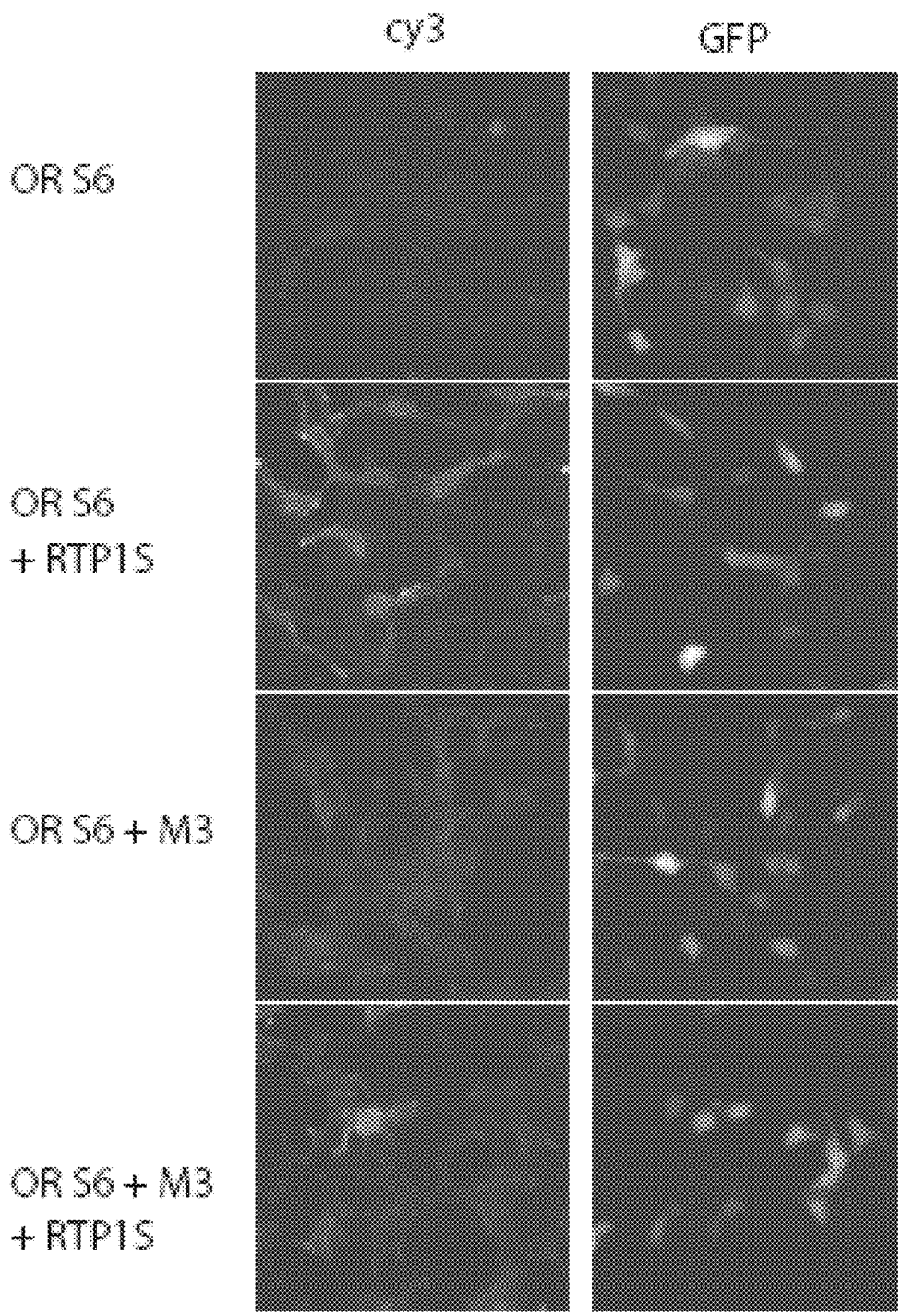
FIGS. 11A-B show that co-expression of M3 does not increase the cell-surface expression of ORs. HEK293T cells were transfected Rho-tagged OR-S6 along with RTP1, M3, or both RTP1 and M3 and cell surface expression was determined using cell surface immunostaining (FIG. 11A) or quantified using FACs analysis (FIG. 11B). Cell surface expression of ORs increased significantly in the cells transfected with RTP1 only, but not in cells transfected with M3 only. Cotransfecting M3 along with RTP1 did not significantly increase cell surface expression of either OR when compared to RTP1-transfected cells.
Figure 11B:
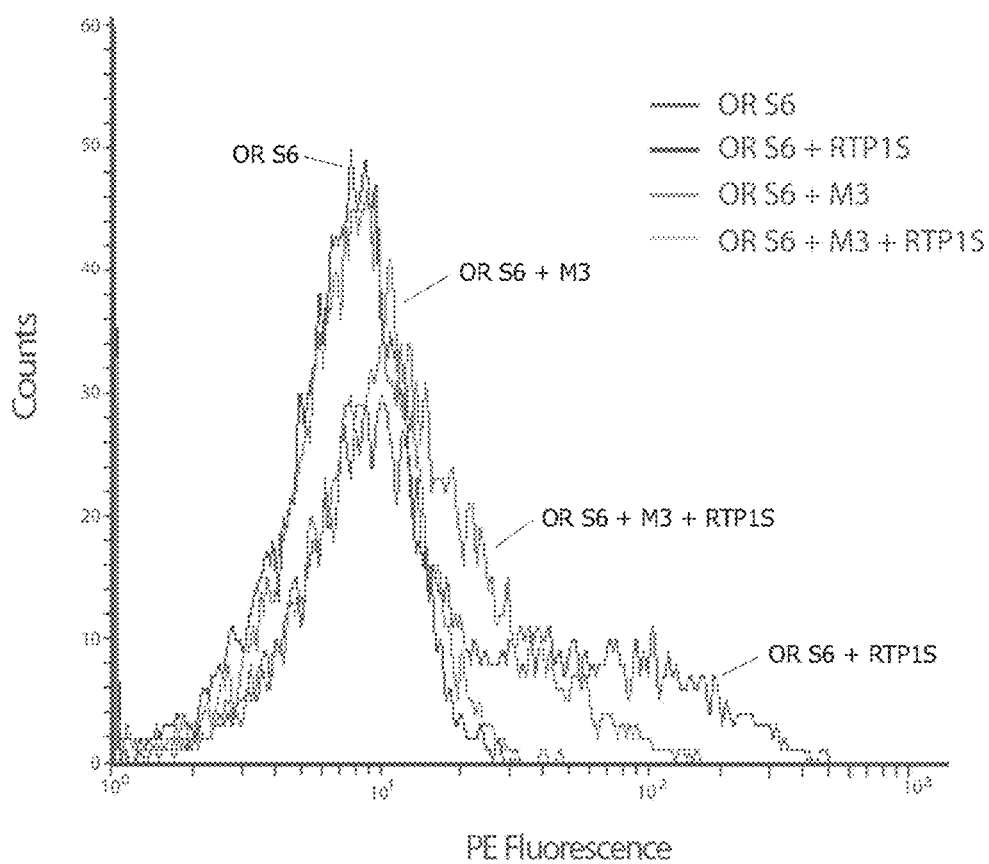

This example shows that expression of M3 does not increase the cell-surface expression of OR. Since previously identified cofactors RTP1 and RTP2, as well as the β2AR and P2Y1 receptors, promote the cell surface trafficking of ORs (see, e.g., H. Saito, M. Kubota, R. W. Roberts, Q. Chi, H. Matsunami, Cell 119, 679 (Nov. 24, 2004); C. Hague et al., Proc Natl Acad Sci USA 101, 13672 (Sep. 14, 2004); C. F. Bush et al., J Biol Chem 282, 19042 (Jun. 29, 2007); each herein incorporated by reference in its entirety), it was hypothesized that M3 performs a similar role. However, analysis using live-cell immunostaining and fluorescence-activated cell sorting (FACS) of HEK293T cells expressing Rho-tagged ORs or Rho-tagged ORs in the presence of M3, revealed that M3 did not increase relative density of OR-S6 at the cell surface, thus precluding the possibility that M3 functions by supporting OR trafficking (FIGS. 11A and 11B).

Example VII

Figure 12A:
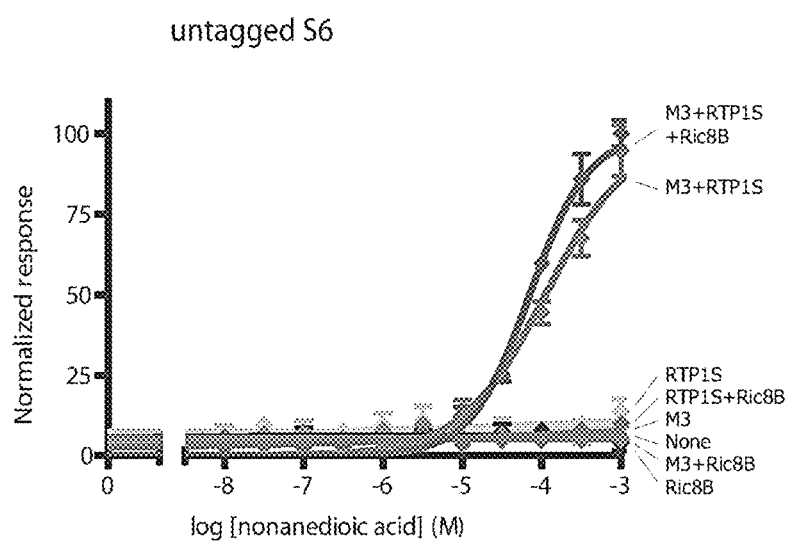
FIGS. 12A-D showM3 potentiation of OR activity is synergistic with mRTP and tag-independent. Dose response curves of luciferase assays performed in HEK293T cells that were transfected with a combination mRTP, Ric-8B, and M3 in cells expressing
Figure 12B:
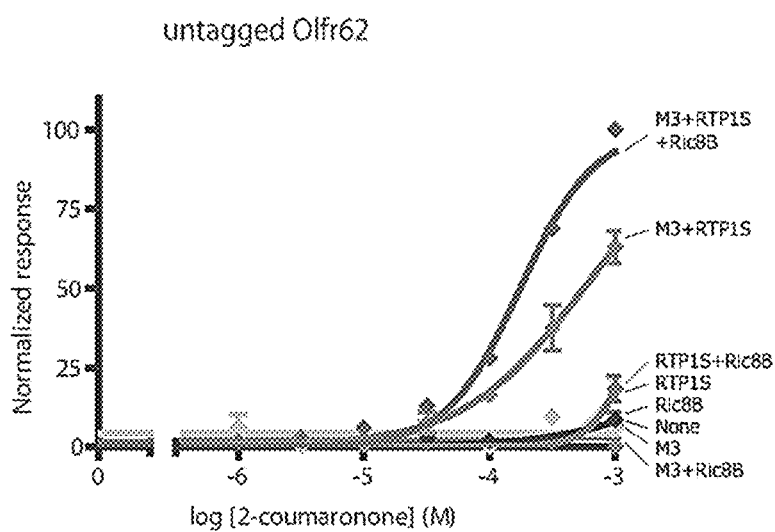
Figure 12C:
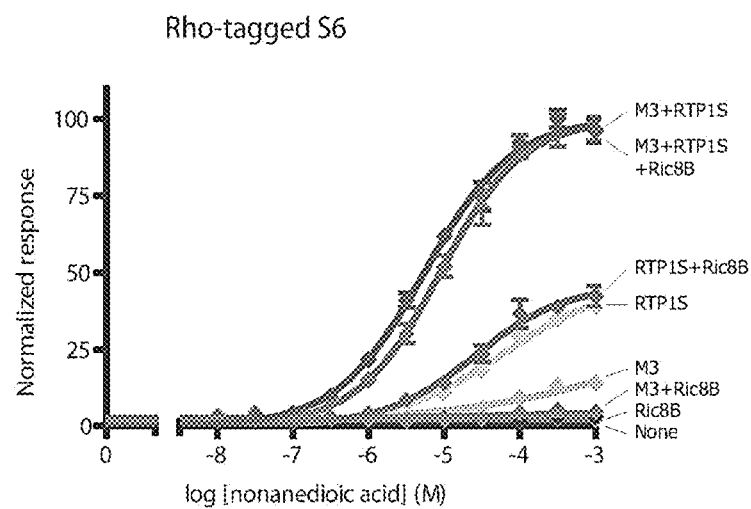
Figure 12D:
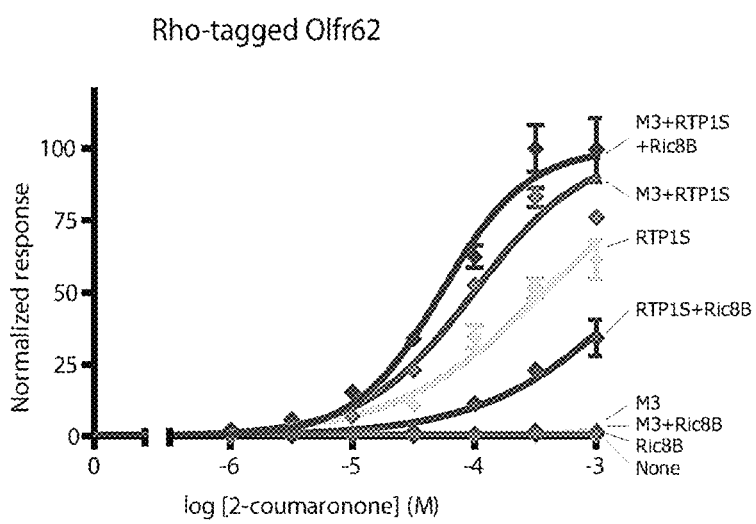
Figure 13A:
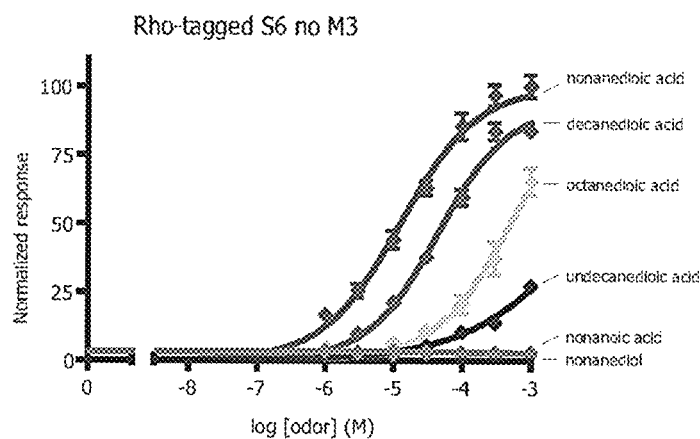
FIGS. 13A-D show M3 expression does not affect the ligand specificity of ORs. Dose response curves of luciferase assays performed in HEK293T cells expressing
Figure 13B:
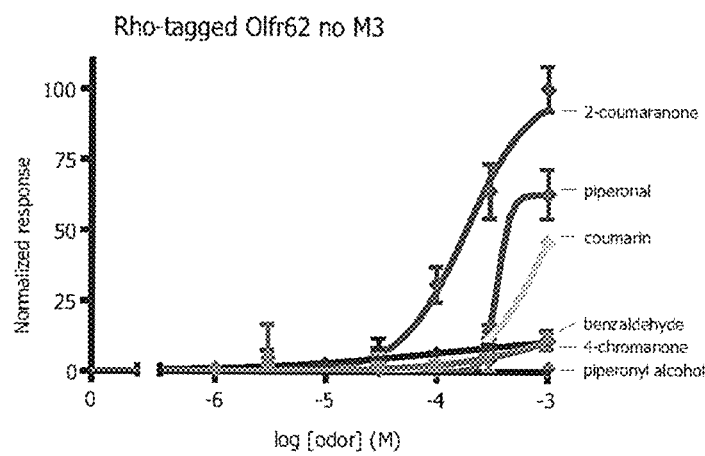
Figure 13C:
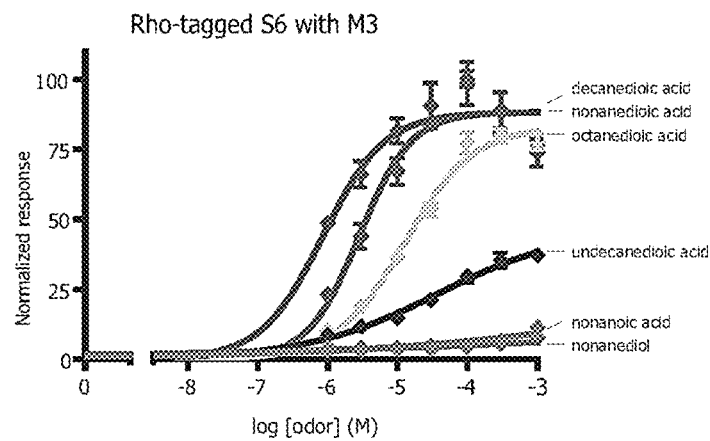
Figure 13D:
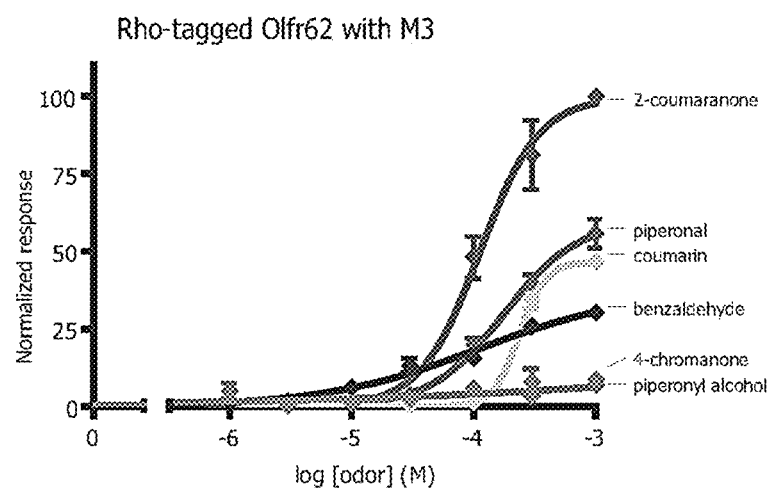

This example demonstrates that M3 shows synergistic effects with RTP1. One way to better understand the mechanism through which M3 acts is to determine whether the potentiation of ORs by M3 is dependent on the expression of other accessory factors. To do this, either Rho-tagged or untagged ORs (OR-S6 or Olfr62) was cotransfected with a combination of M3, RTP1S, and Ric-8B in HEK293T cells and measured OR responses by generating dose-response curves. It was found that while untagged ORs showed relatively poor odor responses in the presence of M3 or RTP1S alone, the response was dramatically enhanced when both M3 and RTP1S were coexpressed with ORs (FIGS. 12A and 12B). When this assay was performed with Rho-tagged ORs, similar synergism was observed between M3 and RTP1S, though OR responses were significantly enhanced as compared to the untagged receptors (FIGS. 12C and 12D). Ric8b did not significantly affect OR responses in our assay. While not limited to a particular mechanism, these results suggest, for example, that M3 and RTP1S synergistically enhance the function of ORs, indicating that M3 acts by enhancing the signaling of ORs that are membrane-targeted by the RTPs and further supports the idea that M3's functional role is unique from that of previously identified accessory proteins.

Figure 7A:
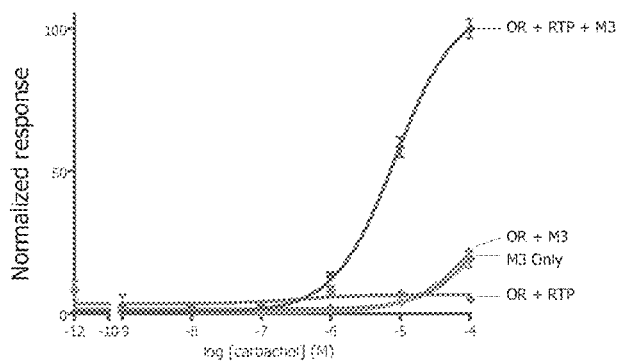
FIGS. 7A-C show the effects of Carbachol, Forskolin, and Ionomycin on cells expressing M3, OR and RTP1S. Stimulation of cells expressing M3, OR, and RTP1S with carbachol were shown to not significantly alter cAMP levels at concentrations lower than $10^{-6}$M. However, at higher concentrations carbachol induced higher responses, apparently through transactivation of OR signaling. This response was not observed in the absence of M3 (FIG. 7A). Slight increase due at 1 mM carbachol concentrations may be attributed, for example, to low-level endogenous M3 expression in HEK293T cells. Administration of Forskolin showed that in the presence of M3, OR activation can be increased in the absence of odor, suggesting that, for example, M3 and OR interaction potentiates OR signaling downstream of odor binding (FIG. 7B). Ionomycin had no effect on OR activation both with or without M3, confirming that, for example, the M3-OR interaction is not simply due to cross-talk of the cAMP and $Ca^{2+}$ secondary messenger pathways in the CRE-luc reporter activation (FIG. 7C).
Figure 7B:
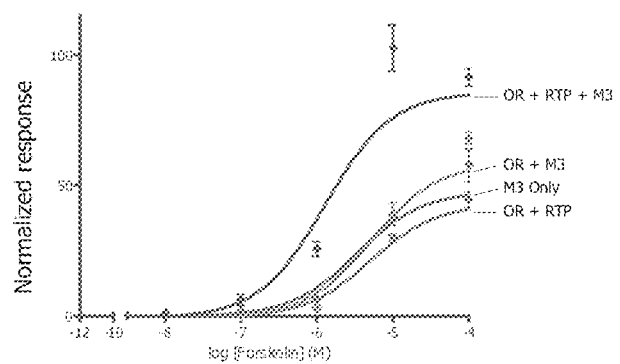
Figure 7C:
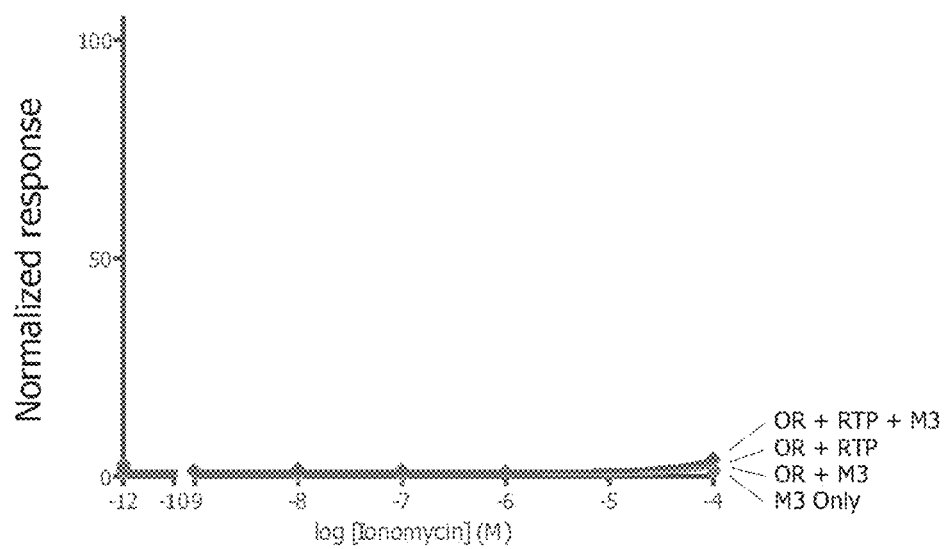

To determine if functional interactions between OR and M3 alters the native signaling pathways of these two receptors, HEK293T cells coexpressing OR, RTP, and M3 were stimulated with forskolin, an adenylyl cyclase activator. Enhanced responses were observed only when OR-S6, RTP1S and M3 were all coexpressed, suggesting that, for example, cell surface OR and M3 coexpression together potentiate adenylyl cyclase activation without OR ligands (FIG. 7B). This is consistent with the idea that M3 facilitates efficient signal transduction. When stimulated with ionomycin, a calcium ionophore, reporter gene responses were not seen, indicating that, for example, ionomycin has no effects (FIG. 7C). Finally when stimulated with an M3 agonist carbachol, dramatic synergistic effects were observed when cells were stimulated with more than 1 uM of carbachol, but only when OR, RTP and M3 were coexpressed. While not limited to a particular mechanism, these results suggest, for example, that at high concentrations of carbachol, M3 activation can lead to transctivation of ORs (FIG. 7A).

Example VIII

This example shows that M3 does not affect the ligand specificity of ORs. To determine whether coexpressing M3 alters the ligand specificity of ORs, cells that express either ORs or ORs and M3 were stimulated with a number of known OR ligands or non-ligands. It was found that for both OR-S6 and Olfr62, M3 potentiated each odor-specific response without altering the relative response levels among the odors, suggesting that M3 plays little or no role in OR ligand selectivity (FIG. 13).

Example IX

Figure 14:
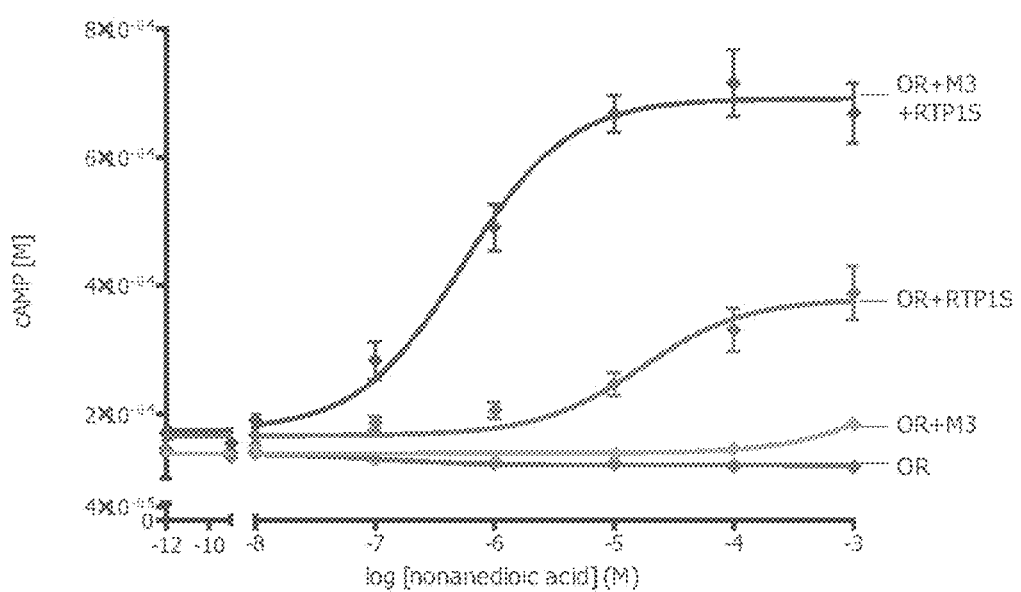
FIG. 14 shows that M3 increases cAMP production upon OR activation. Dose response curves of cAMP assays performed in HEK293T cells that were transfected with 1. OR-S6 only, 2. OR-S6 and M3, 3. OR-S6 and RTP, and 4. OR-S6, RTP1S, and M3. Note the significant increase in [cAMP] when OR-S6 was coexpressed with M3 and RTP, in comparison to cotransfection with either alone. Data were obtained from triplicate samples and the experiment was replicated four times.

This example shows that M3 increases cAMP production upon OR activation. To verify that M3 does not increase the luciferase reporter gene activity by mechanisms independent of OR-mediated cAMP production, the changes in cAMP levels in cells coexpressing OR-S6 and accessory factor RTP1S with and without M3 following odor stimulation were quantified. When OR, RTP1S, and M3 were coexpressed, the background level was slightly higher than other conditions. Following stimulation with the OR-S6 ligand nonanedioic acid, a dramatic increase in cellular cAMP levels in cells coexpressing M3 was observed, mirroring the results obtained in the luciferase gene reporter assays (FIG. 14). While not limited to a particular mechanism, these results confirm that, for example, M3 modulates the OR signal transduction pathway at or upstream to cAMP production.

Figure 15:
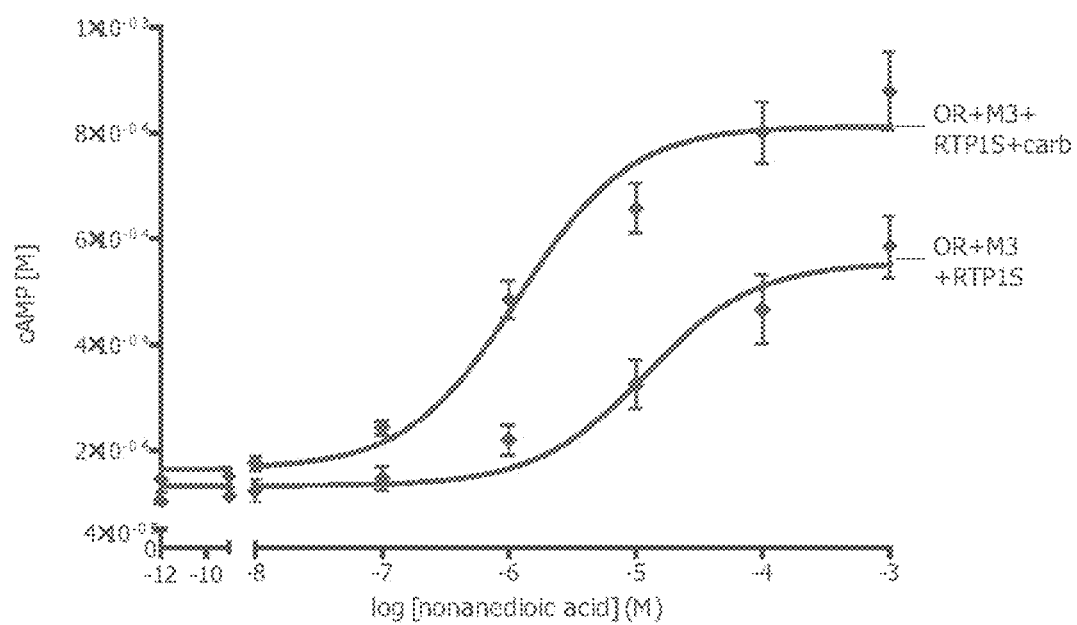
FIG. 15 shows cAMP production is further increased upon costimulation with nonspecific M3 agonist carbachol. Dose response curves of cAMP assays performed in HEK293T cells that were transfected with OR-S6, RTP1S, and M3. Costimulation with $10^{-7M}$ carbachol further stimulates production of cAMP in cells cotransfected with M3 and RTP1S. Data were obtained from triplicate samples and the experiment was replicated twice.
Figure 16A:
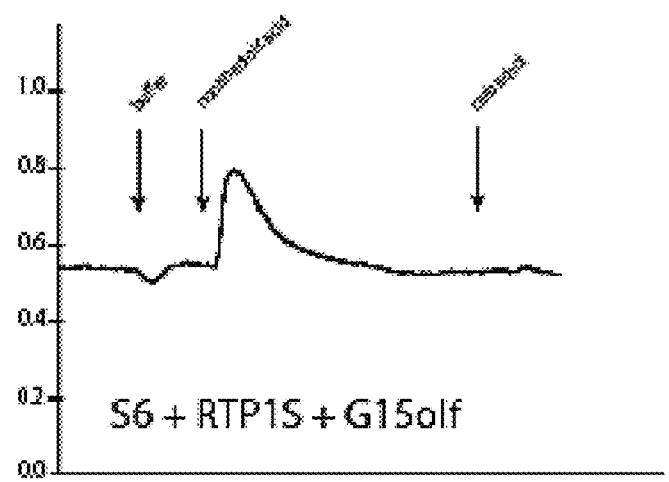
FIGS. 16A-F show that activation of OR-S6 leads to calcium release mediated by M3 activation.
Figure 16B:
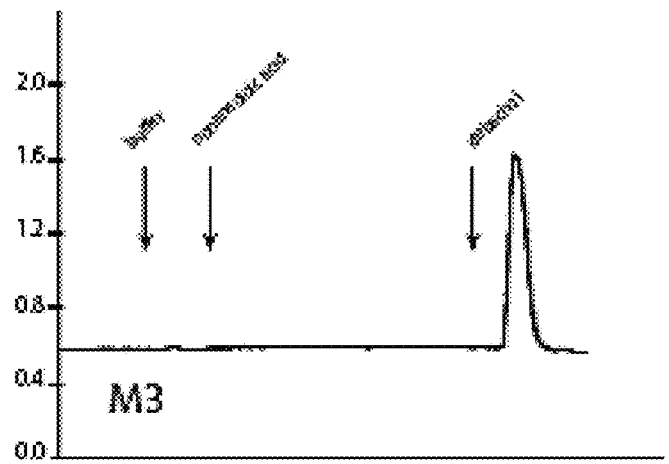
Figure 16C:
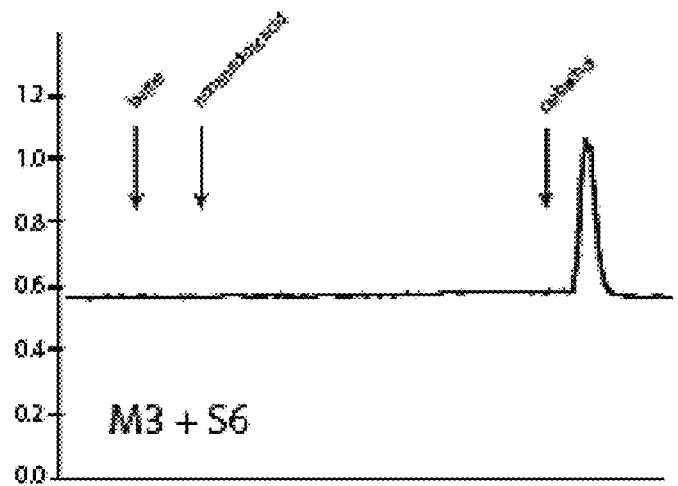
Figure 16D:
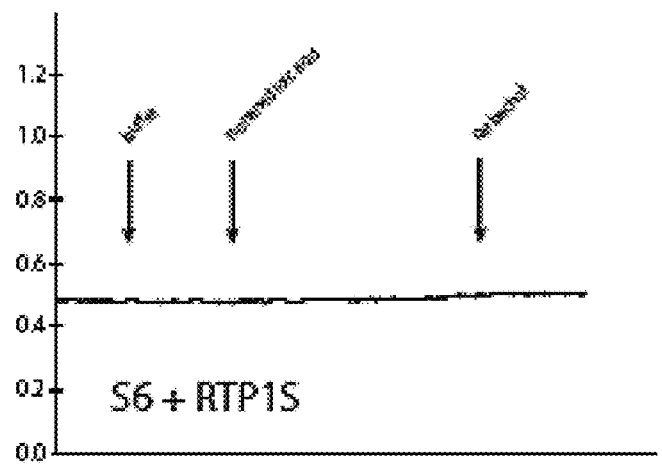
Figure 16E:
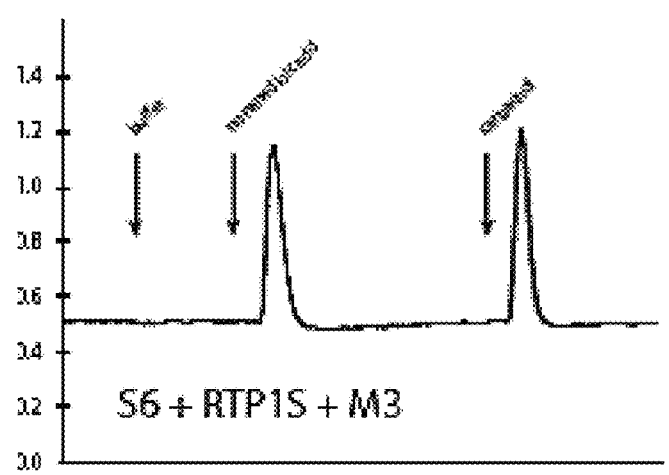
Figure 16F:
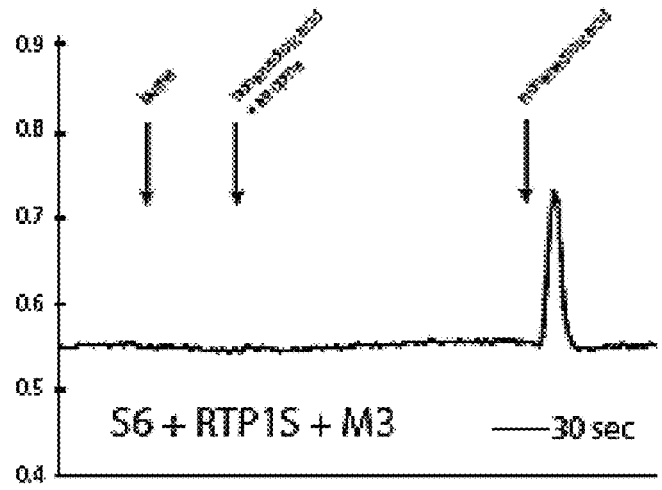

Using this same assay, it was also that the rise in cAMP following OR stimulation is even more dramatic in the presence of carbachol at $10^{-7}$M (FIG. 15).

Example X

This example shows that activation of the OR leads to transactivation of M3. Since M3 potentiates OR signaling, the possibility that OR activation may also enhance M3 signaling was considered. M3 was expressed, both with and without OR-S6 and its accessory factors in HEK293T cells, and monitored calcium release following stimulation with carbachol or odor. No calcium response was observed when HEK293T cells expressing OR-S6 alone were stimulated with nonanedioic acid. As a positive control for OR expression, cells coexpressing ORs and $G_{\alpha15olf}$, a promiscuous, chimeric G-protein, was shown to generate a calcium response following stimulation with nonanedioic acid (FIG. 16) (see, e.g., H. Zhuang, H. Matsunami, J Biol Chem 282, 15284 (May 18, 2007); herein incorporated by reference in its entirety).

In contrast to OR-S6, M3 is a $G_q$-coupled receptor, and stimulation of M3-expressing cells with carbachol resulted in a robust calcium response. No response was observed when these cells were stimulated with nonanedioic acid.

However, when OR-S6 and its cofactors were coexpressed with M3, stimulation with nonanedioic acid alone elicited a strong calcium response. This response required M3 activation, since this response was abolished by costimulating the same cells with odor and the M3 antagonist atropine. While not limited to a particular mechanism, these results suggest that the effects of M3 and OR are mutual.

Example XI

Figure 18:
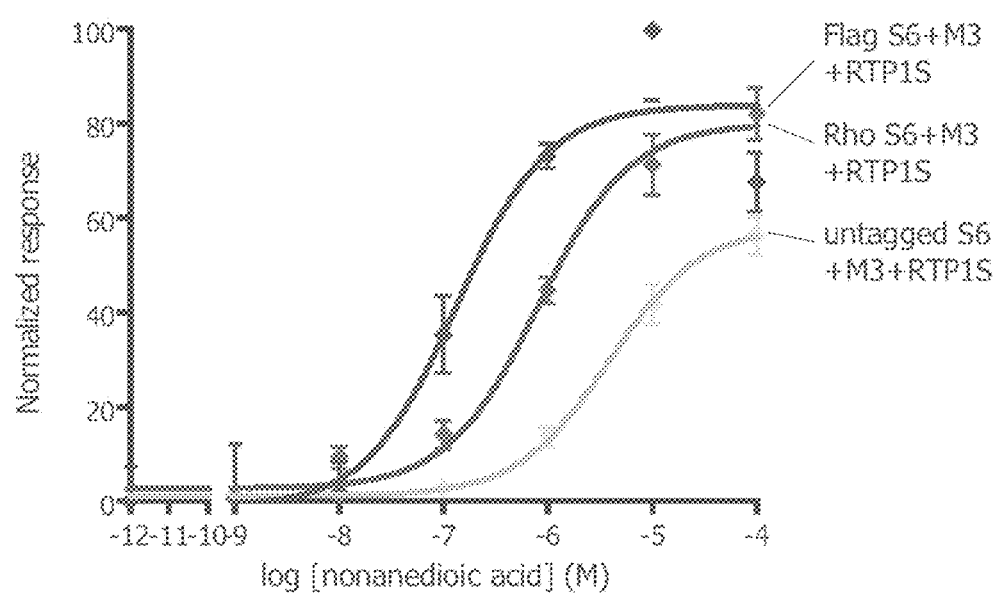
FIG. 18 shows Flag-OR S6 responds as robustly as Rho-OR S6 and more robustly than untagged OR-S6. To ensure that Flag-tagged versions of OR-S6 behaves similarly as Rho-tagged OR S6 in our heterologous system, a cAMP-mediated gene assay was performed to assess the functional response of Flag-S6 in comparison to Rho-S6 and found that Flag-tagged S6 responds similarly, likely even more robustly, than Rho-tagged S6, indicating that Flag-tagged S6 are functionally active on the cell surface. Results were obtained in triplicate; experiment was repeated 3 times.
Figure 19A:
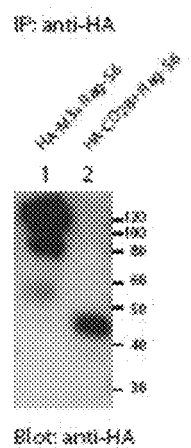
FIGS. 19A-F show M3 and S6 stably interact in HEK293T cells. Co-immunoprecipitation studies of HA-tagged M3 and Flag-tagged OR-S6 in HEK293T cells were performed. When the cell extract was precipitated with anti-HA antibodies, Flag-S6 proteins were detected.
Figure 19B:
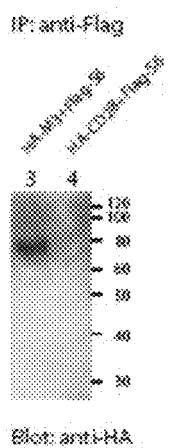
Figure 19C:
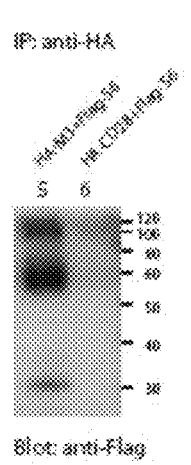
Figure 19D:
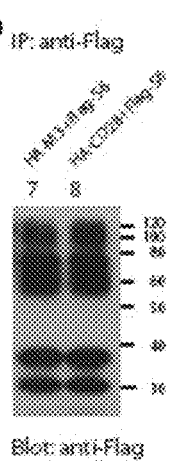
Figure 19E:
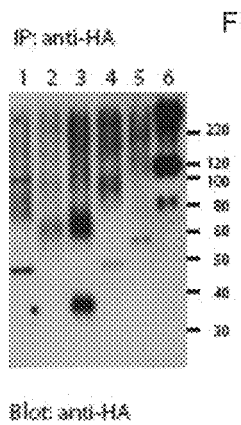
Figure 19F:
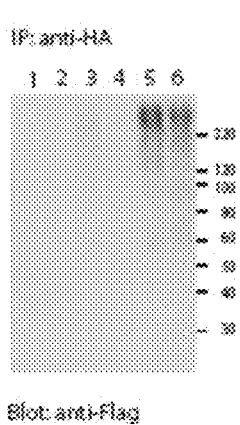

This example describes the physical interaction of M3 and the OR. Based on the functional interaction between M3 and ORs, it was hypothesized that they may interact to form stable heteromers. To assess this possibility, co-immunoprecipitation studies were carried out by coexpressing N-terminal HA-tagged M3 and Flag-tagged OR-S6 in HEK293T cells. Flag-tagged OR-S6 was expressed on the cell surface and responded to its ligand nonanedioic acid (FIG. 17 and FIG. 18). When Flag-tagged M3 was precipitated from the cell extract with anti-Flag antibodies, HA-tagged S6 proteins were co-purified. Conversely, when precipitated cell extracts with anti-HA antibodies were precipitated, Flag-tagged S6 proteins could be detected (FIG. 19). No co-precipitation was detected when HA-tagged CD28, a negative control, was expressed (FIG. 19A). When Flag-S6 was coexpressed with other HA-tagged GPCRs, M3 and M2 were coprecipitated. In contrast, other GPCRs were not efficiently copurified with the OR. While not limited to a particular mechanism, M3 and S6 likely interact to form stable, functional complexes in HEK293T cells. Interaction between M2 and the OR may, for example, explain inhibition of activation of ORs by M2 (FIG. 2). Since M2 immunoreactivity was not observed in the olfactory cilia (FIG. 5), M2 is likely to have no physiological role in olfactory transduction in vivo.

Example XII

This example provides the materials and methods for Examples I-XI.

DNA and Vector Preparation

The open reading frames were amplified using Phusion polymerase (Finnzymes) according to manufacturer protocols. cDNA template was prepared from C57BL/6 mice described previously (see, e.g., H. Saito, M. Kubota, R. W. Roberts, Q. Chi, H. Matsunami, Cell 119, 679 (Nov. 24, 2004); herein incorporated by reference in its entirety). Amplified fragments were subcloned into pCI (Promega) for sequence verification.

Dual Glo Luciferase Assay and Chemicals

HEK293T cells Hana3A cells were maintained in minimal essential medium (MEM) containing 10% fetal bovine serum (M10) and penicillin-streptomycin and amphotericin solution. Lipofectamine 2000 (Invitrogen) was used for transfection following manufacturer's protocols. The Dual-Glo Luciferase Assay System used here was carried out as described previously (see, e.g., H. Zhuang, H. Matsunami, Nat Protoc 3, 1402 (2008); herein incorporated by reference in its entirety). Briefly, cAMP response element (CRE)-luciferase (Stratagene) was used to measure OR activation. *Renilla* luciferase driven by a constitutively active simian virus 40 (SV40) promoter (pRL-SV40; Promega) served as an internal control for cell viability and transfection efficiency. Cells were plated on poly-D-lysine-coated 96-well plates (NUNC) 2 days prior to assay. Cells were transfected with ORs in either Hana3A or HEK293T cell lines along with various combinations of RTP1S, Ric-8b, M3, CRE-luciferase, and pRL-SV40. 18-24 hours after transfection, cells were rinsed with 50 µl of CD293 (Invitrogen) and stimulated with 25 µl of odorant solution dissolved in CD293. Cells were incubated for 4 hours at 37° C. and 5% $CO_2$ before luciferase assays. Protocols for measuring luciferase and *Renilla* luciferase activities were as described by the manufacturer (Promega). Normalized luciferase activity was calculated with the formula $(L_N-L_{min})/(L_{max}-L_{min})$, where $L_N$ is the luminescence of firefly luciferase in response to the odorant, $L_{min}$ is the minimum luciferase value on a plate or set of plates, and $L_{max}$ is the maximum luciferase value on a plate or set of plates. The data was analyzed with Microsoft Excel and GraphPad Prism 5. Odorants and muscarinic agonists and antagonists were from Sigma except for darifenacin, which was purchased from Santa Cruz.

In-Situ Hybridization, Immunohistochemistry,

The procedure for in situ hybridization was previously described (see, e.g., H. Saito, M. Kubota, R. W. Roberts, Q. Chi, H. Matsunami, Cell 119, 679 (Nov. 24, 2004); herein incorporated by reference in its entirety). Briefly, Dig labeled cRNA probes were used to hybridize target mRNAs on fresh frozen tissues. Hybridization signals were detected with anti-DIG-AP (Roche) and NBT-BCIP (Promega). For immunohistochemistry, fresh frozen sections were incubated with anti-M3 (Sigma), anti-M1 (Sigma), anti-M5 (Sigma) and anti-ACIII (Santa Cruz). After washing, tissues were incubated with Cy-3 conjugated anti-rabbit IgG (Jackson Immnologicals)

Calcium Imaging

For calcium imaging of acutely dissociated OSNs, the protocol as described previously with modifications was followed (see, e.g., B. Malnic, J. Hirono, T. Sato, L. B. Buck, Cell 96, 713 (Mar. 5, 1999); T. Sato, J. Hirono, M. Tonoike, M. Takebayashi, J Neurophysiol 72, 2980 (December, 1994); each herein incorporated by reference in its entirety). Dissected adult mouse olfactory epithelium was treated with 0.025% trypsin (Invitrogen) for 12 min at 37° C. Minced tissues were then "printed" on poly-D-lysine-coated cover glasses. Cells were loaded with 4 uM Fluo-4 (Invitrogen) and 7 uM Fura red (Invitrogen) for 60 min at room temperature. Data acquisition and odor stimulation were performed as described previously (see, e.g., Y. Ishimaru et al., Proc Natl Acad Sci USA 103, 12569 (Aug. 15, 2006); herein incorporated by reference in its entirety). Briefly, the Live Imaging mode of Leica confocal microscope was used to record calcium-dependent cell fluorescence. Cells were exposed to a constant flow of bath solution (Hanks buffer containing 10 mM HEPES). Odor solution (mix of 10 odorants: isoeugenol, vanillin, coumarin, nonanoic acid, heptanal, benzyl acetate, nonanediol, acetophenone, octanol, and (−)-carvone at 10 uM each) were applied for ~8 sec by changing the bath solution with a peristaltic pump.

For data analysis, neurons were first counted by identifying those cells that showed a clear calcium response to KCl. Of these cells, cells that showed a response to the odor mix and/or odor mix+antagonist were then marked for further analysis. Each field recorded typically contained 40-200 KCl-responding cells and 1-5 odor-responding cells.

Figure 20:
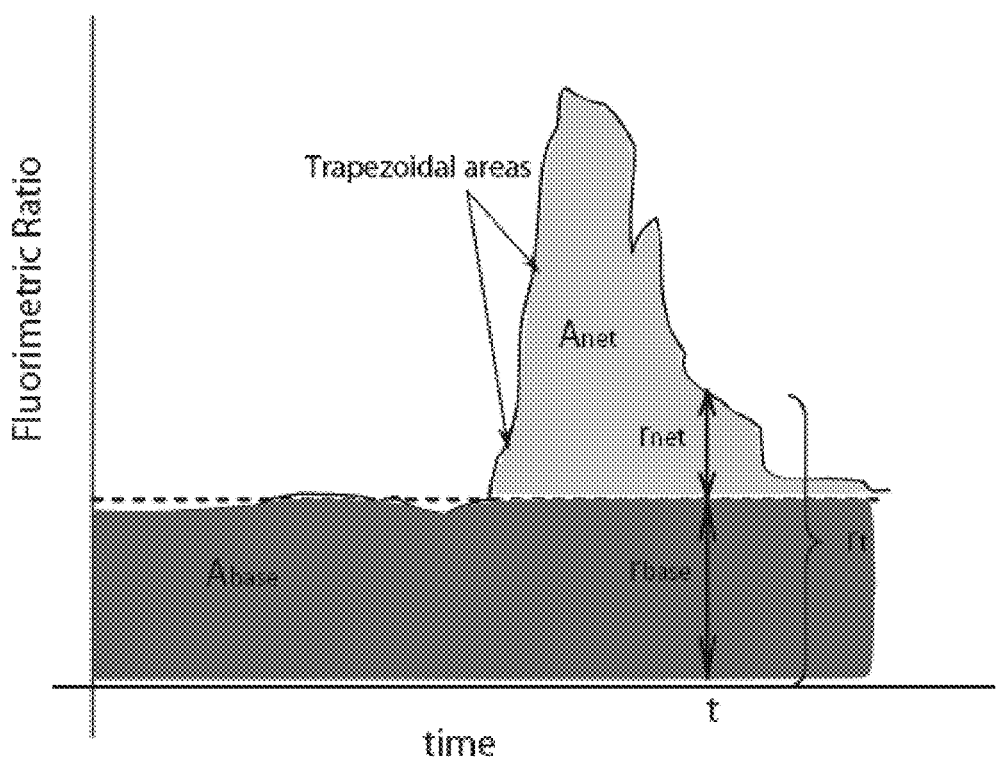
FIG. 20 provides a graphical explanation of the trapezoidal method used to calculate the net responses of individual OSNs presented in FIG. 9. Briefly, the region above the "- - - - - -" line marks the area of response as calculated by totaling the average response ($r_t$) over the specified time interval multiplied by a set increment of time, t to produce trapezoidal approximations of the area underneath the response curve. The total area under the curve is then normalized by subtracting the area underneath the $r_{base}$, which is $A_{base}$, to obtain the net response, $A_{na}$, that represents the net response $r_{net}$ over the entire response time.

Euler's trapezoidal method was used to calculate and compare the responses to odor mix or mix+antagonist of each cell (FIG. 20) (see, e.g., T. M. Wolever, D. J. Jenkins, A. L. Jenkins, R. G. Josse, Am J Clin Nutr 54, 846 (November, 1991); herein incorporated by reference in its entirety). Specifically, area $A_{total}$ under the total response curve between $t_0$ and t=, defined for a total of 30 seconds prior and post to the response maxima, was calculated by summing the net response $r_n$ and $r_{n+1}$ multiplied by the duration of the response. The responses were added in single second increments, so that the trapezoid method sums the response underneath the curve between any two consecutive seconds (ie. Between $t_1$ and $t_2$, the area $A_1$ would equal $(r_1+r_2)*t$, where t=1. To normalize $A_{total}$ against the background of each cell, a baseline curve was drawn using the average baseline response rbase of the first four of the 20 $r_n$ values, which were the net response values before cell stimulation. $r_{base}$ was next multiplied by 20 seconds, which was the total time interval monitored for each cell to get $A_{base}$. This baseline area $A_{base}$ was substracted from the net response of each cell calculated using the trapezoid method, leaving what is a $A_{net}$ value that defines only the area underneath the response curve. The $A_{net}$ for odor and odor+antagonist were compared using the student's paired t-test.

A total of 34 and 36 cells were used for each t-test analysis for the two different antagonists, respectively. All data analysis was done with Image J, Igor Pro, and Microsoft Excel.

Calcium imaging with HEK293T cells was performed as described (see, e.g., Y. Ishimaru et al., Proc Natl Acad Sci USA 103, 12569 (Aug. 15, 2006); herein incorporated by reference in its entirety).

Immunocytochemistry and Fluorescence-Activated Cell Sorting Analysis

For cell surface staining and fluorescence-activated cell sorting (FACS), the protocol as described previously was followed (see, e.g., H. Zhuang, H. Matsunami, Nat Protoc 3, 1402 (2008); herein incorporated by reference in its entirety). Briefly, cells were incubated in MEM+10% FBS containing mouse monoclonal antibody to rhodopsin, 4D2 (see, e.g., D. W. Laird, R. S. Molday, Invest Ophthalmol Vis Sci 29, 419 (March, 1988); herein incorporated by reference in its entirety) at 4° C. for 30 minutes. After washing, cells were incubated with Cy3-conjugated donkey anti mouse IgG (Jackson Immunologicals), washed, and mounted for observation. For FACS analysis, HEK293T cells expressing Rho-tagged ORs were labeled with phycoerythrin (PE)-conjugated anti-mouse IgG (Jackson Immunologicals). GFP was cotransfected as a positive control marker. Quantification of the intensity of OR cell surface expression were taken as the ratio of PE to GFP fluorescence. 7-amino-actinomycin D (Calbiochem) was used to stain the cells before flow cytometry to mark dead cells, which were excluded from the analysis.

cAMP Assay

Alphascreen cAMP assay (Perkin Elmer) was used to measure changes of cAMP. Cells were plated on 96-cell plate (poly D lysine coated, NUNC). 24 hours after transfection, cells were washed in Hanks containing 5 mM HEPES, 0.1% BSA and 500 uM IBMX for 30 minutes. The cells were then stimulated with Hanks containing 5 mM HEPES, 0.1% BSA and 500 uM IBMX and corresponding chemicals. The stimulated cells were incubated for 10 min at room temperature before lysis. The manufacture's protocol was used to measure cAMP.

Immunoprecipitation

Immunoprecipitation was performed as described (see, e.g., H. Saito, M. Kubota, R. W. Roberts, Q. Chi, H. Matsunami, Cell 119, 679 (Nov. 24, 2004); herein incorporated by reference in its entirety). Briefly, HEK293T cells were plated and transfected with ORs, RTP1S, and M3 cDNAs. Cells were incubated for 24 hours at 37° C. and 5% $CO_2$ and placed in lysis buffer (50 mM Tris [pH 7.4], 150 mM NaCl, 1% NP-40) containing proteinase inhibitor mix (complete mini, Roche). The lysates were incubated with anti-Flag M2 affinity gel (Sigma) or anti-HA affinity matrix (Roche) for 2 hr at 4° C. and washed with lysis buffer. The bound proteins were then eluted by incubating with SDS sample buffer at room temperature for 2 hours. SDS-PAGE and Western blotting were performed according to Mini-Protean 3 Cell (Bio-Rad) instruction manual.

All publications and patents mentioned in the above specification are herein incorporated by reference. Although the invention has been described in connection with specific some embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method for identifying an odorant receptor ligand, comprising:
   a) providing
      i) a cell line comprising recombinant cells which have been genetically engineered to express a functional mammalian odorant receptor, wherein the cell line comprises a heterologous nucleic acid encoding a mammalian M3 muscarinic acetylcholine receptor in combination with a heterologous nucleic acid encoding a mammalian RTP1S protein;
      ii) a composition comprising at least one test compound;
   b) exposing said test compound to said cell; and
   c) detecting the activity of said odorant receptor.

2. The method of claim 1, wherein said composition comprising at least one test compound comprises a mixture of different test compounds.

3. The method of claim 1, wherein said detecting comprises detecting a reporting agent.

4. The method of claim 1, wherein said odorant receptor is a human odorant receptor.

5. The method of claim 1, wherein said test compound is an odoriferous molecule.

6. The method of claim 1, wherein said odorant receptor is a murine odorant receptor.

7. The method of claim 1, wherein said odorant receptor is a synthetic odorant receptor.

8. The method of claim 1, wherein said at least one test compound is exposed in the presence of a reference compound previously identified as a ligand for said odorant receptor.

9. The method of claim 1, wherein said at least one test compound corresponds to a mixture of different test compounds.

10. The method of claim 1, further comprising the step of d) detecting the presence or absence of an odorant receptor ligand based upon said activity.

11. The method of claim 1, wherein said exposing said test compound to said cell occurs in a setting selected from the group consisting of an in vivo setting, an in vitro setting, and an ex vivo setting.

* * * * *

SEQUENCE LISTING

```
<160> NUMBER OF SEQ ID NOS: 11

<210> SEQ ID NO 1
<211> LENGTH: 1383
<212> TYPE: DNA
<213> ORGANISM: Homo sapiens

<400> SEQUENCE: 1
atgaacacct cagtgccccc tgctgtcagt cccaacatca ccgtcttggc accaggaaag      60
ggtccctggc aagtggcatt catcgggatc accacaggcc tcctgtctct ggctacagtg     120
acaggcaacc tgctggtgct catctccttc aaggtcaaca cagagctcaa gacagtcaac     180
aactacttcc tgctgagcct ggcctgtgct gatctcatca ttggcacttt ctccatgaac     240
ctctatacca catacctgct catgggccac tgggctctgg gcacactggc ctgtgacctc     300
tggctggccc tggactatgt ggccagcaac gcctctgtca tgaatcttct gctcatcagc     360
tttgaccgtt acttctcagt gacccgaccc ctgagctacc gagccaagcg cactccccgc     420
agggcagctc tgatgattgg cctcgcgtgg ttggtttcct tcgttctctg ggccccagcc     480
atcctcttct ggcaatacct agttggggag cggacagtgc tggctgggca gtgctacatc     540
cagttcctct cccaacccat catcactttt ggcacagcca tggccgcctt ctacctccct     600
gtcacagtca tgtgtacgct gtactggcgc atctaccggg agacagaaaa ccgagcccgg     660
gagctagcag ccctacaggg ctctgagaca ccaggcaaag gtggtggcag cagcagcagc     720
tcagagaggt cacagccagg agctgaaggc tcacccgagt cacctccagg ccgctgctgt     780
cgctgttgcc gggcacccag acttctgcag gcctacagct ggaaagaaga agaggaagag     840
```

```
gatgaaggct ccatggagtc cctcacatcc tctgaaggtg aggagcctgg ctcagaagtg      900
gtgatcaaga tgcctatggt agatcctgag gcacaggcac ccaccaagca gcctcccaaa      960
agctccccaa atacagtcaa gaggcccacc aagaaaggcc gagaccgagg cggcaaaggc     1020
caaaaacccc gagggaagga acaactggcc aagagaaaga ccttctcact ggtcaaggag     1080
aagaaggcag ctcggaccct gagtgccatc ctgctggcct tcatcctcac ctggacacca     1140
tataacatca tggtgctggt gtctacattc tgcaaggact gtgttccaga accctatgg     1200 gagctgggct actggctttg ctacgtcaac agcactgtca accccatgtg ctacgcactc     1260
tgcaacaaag ccttccggga cactttccgc ctgctgttgc tctgccgctg ggacaagcgg     1320
cgctggcgca aaatccccaa gcgccctggc tctgtgcacc gcacccctc ccgccaatgc     1380 taa                                                                   1383

<210> SEQ ID NO 2
<211> LENGTH: 1401
<212> TYPE: DNA
<213> ORGANISM: Homo sapiens

<400> SEQUENCE: 2
atgaataact caactaactc ctcgaacaat ggtttggcta ttaccagtcc ttacaagaca       60
tttgaagtgg tatttattgt ccttgtggct ggatccctca gtctggtgac catcattggg      120
aacattctag tcatggtttc cattaaagtc aaccgccacc ttcagactgt caacaattac      180
ttcttgttca gcctggcctg tgctgacctc atcataggtg ttttctccat gaacttgtat      240
accctctaca ctgtgattgg ctactggcct ttgggacctg tagtgtgcga cctttggcta      300
gccttggact atgttgtcag caatgcctcc gttatgaatc ttctcatcat cagctttgat      360
agatacttct gtgtcacaaa acctctaacc tacccagtta agcggaccac aaaaatggca      420
ggcatgatga ttgcagctgc gtgggttctt tccttcatcc tctgggcccc agccattctc      480
ttctggcagt tcatcgtagg ggtaaggact gtggaagacg gggagtgcta cattcagttc      540 tttttccaacg ctgccgtcac ctttggcact gccattgcgg cttttctatct gcctgtcatc      600 atcatgactg tgctctattg gcacatatcc cgggcgagca gagcagaat aaagaaagaa      660 aagaaggaac cagtggccaa ccaagacccg gtgtctccga gtctagtgca aggaagaatt      720
gtaaagccaa caacaacaa catgcctggt ggtgatggtg gcctggagca caacaagatc      780
cagaatggca aggctccgcg ggacggtggg actgaaaact gcgttcaggg ggaggagaaa      840
gaaagctcca acgactccac gtctgtcagt gccgtgcct ccaacatgag agatgatgag      900
ataacccagg atgaaaacac ggtttccact tccctgggcc actccaaaga tgacaactct     960
aggcagacat gcatcaaaat tgtcaccaag acccaaaagg gtgacgcatg cacaccaaca     1020
agtaccacag tagaactagt gggatcgtca ggtcagaatg gtgatgaaaa gcagaacatt     1080
gtagcccgca aaattgtgaa gatgaccaag cagcctgcca aaagaagcc tcctccatcc     1140 cgggaaaaga agtgaccag gacaatcttg gctatcctgt ggctttcat catcacgtgg     1200 gcgccataca atgtcatggt gctcatcaat accttctgtg cacctgcat ccccaataca     1260 gtgtggacaa ttggctactg gctctgttac attaatagca ccatcaaccc tgcctgctat     1320
gcactttgta acgccacctt caaaaagact tttaagcacc tccttatgtg tcattacaag     1380
aacataggcg ctacaaggta a                                               1401

<210> SEQ ID NO 3
```

<211> LENGTH: 1770
<212> TYPE: DNA
<213> ORGANISM: Homo sapiens

<400> SEQUENCE: 3

| | | | | | |
|---|---|---|---|---|---|
| atgaccttgc | acagtaacag | tacaacctcg | cctttgtttc | ccaacatcag | ctcttcctgg | 60 |
| gtgcacagtc | cctcagaggc | ggggctgccc | ttggggacag | tctctcaatt | ggacagctac | 120 |
| aacatttccc | aaacctctgg | gaatttctcc | tcaaatgaca | cctccagtga | ccctctaggg | 180 |
| ggccacacca | tctggcaagt | ggtcttcatt | gcattcttga | ctggcttcct | ggcattggtg | 240 |
| accatcatcg | gcaacatcct | tgtcattgtg | gcatttaagg | tcaacaaaca | gctgaagaca | 300 |
| gtcaacaact | acttcctctt | aagcctggcc | tgcgcagatc | tgatcatcgg | ggtcatttcc | 360 |
| atgaacctgt | tcacgaccta | catcattatg | aaccgctggg | ctctggggaa | cttagcctgt | 420 |
| gacctctggc | tttccattga | ctatgtggcc | agcaatgctt | ctgtcatgaa | tctgctggtg | 480 |
| atcagctttg | acaggtactt | ttctattacc | aggccactca | cttaccgagc | caaacgaaca | 540 |
| acaaaacgag | ccggtgtgat | gattggtctg | gcttgggtca | tctcctttgt | cctgtgggct | 600 |
| cctgccatct | tgttctggca | atactttgta | gggaagagaa | ctgtgccccc | cggagaatgt | 660 |
| ttcattcagt | ttctaagtga | gcccaccatc | accttcggca | cggcgatcgc | tgccttttac | 720 |
| atgcctgtca | ccatcatgac | tattttatac | tggagaatct | ataaggagac | tgagaaacgt | 780 |
| accaaagagc | tggctgggct | acaggcctct | gggacagaag | cggaagcaga | aaactttgtc | 840 |
| caccccacag | gcagttctcg | aagctgtagc | agctatgagc | tacaacagca | aggcacgaaa | 900 |
| cggtcatcta | ggaggaagta | tggtggctgt | cacttctggt | tcacaactaa | gagctggaag | 960 |
| cccagtgctg | agcagatgga | ccaagaccac | agtagcagtg | acagttggaa | taacaacgat | 1020 |
| gctgctgcct | ccctggaaaa | ctctgcttct | tctgatgaag | aggatattgg | ctcagagacc | 1080 |
| agagccatct | attccattgt | actcaagctg | ccgggtcata | gcaccatcct | caactctacc | 1140 |
| aagctacccc | tctcagataa | cctgcaggtg | ccagacaagg | acctggggac | tatggatgta | 1200 |
| gagagaaatg | cccataagct | tcaggcccag | aagagtatgg | atgaccgtga | caactgtcag | 1260 |
| aaggacttct | ccaagctccc | catccagtta | gagtctgccg | tggacacagc | caagacctct | 1320 |
| gacaccaact | cctcggtgga | caagaccacg | gccgctctac | ctctgtcctt | caaagaagcc | 1380 |
| acgctggcta | agaggtttgc | tctcaagacc | agaagtcaga | tcaccaagcg | gaaaaggatg | 1440 |
| tcgctcatca | aggagaagaa | ggccgcccag | acactcagtg | ccatcttgct | ggctttcatc | 1500 |
| atcacgtgga | cccctacaa | catcatggtc | ctggtgaaca | ccttctgtga | cagctgcata | 1560 |
| cccaaaacct | attggaatct | gggctactgg | ctgtgctata | tcaacagcac | cgtgaacccc | 1620 |
| gtgtgctatg | ccctgtgcaa | caagacattc | agaaccacct | tcaagatgct | tctcttatgc | 1680 |
| cagtgtgaca | agaggaagcg | cgcgcaaacag | cagtaccagc | agagacagtc | cgtcattttt | 1740 |
| cacaagcgag | tgcctgagca | ggccttgtag | | | | 1770 |

<210> SEQ ID NO 4
<211> LENGTH: 1440
<212> TYPE: DNA
<213> ORGANISM: Homo sapiens

<400> SEQUENCE: 4

| | | | | | |
|---|---|---|---|---|---|
| atggcgaact | tcacacctgt | caatggcagc | tcagccaatc | agtctgtgcg | cctggtcaca | 60 |
| acagcccaca | accacctgga | gacagtggag | atggtgttca | ttgcgacagt | gactggttcc | 120 |
| ctgagcctgg | tgactgtggt | gggtaacatc | ctggtgatgc | tgtccatcaa | ggtcaacagg | 180 |

```
cagttgcaga cagtcaacaa ctacttcctg ttcagcctgg cgtgtgcaga tctcatcata    240
ggggcgttct ctatgaacct ttacacctta tacatcatca agggctactg cccctgggt     300 gccgtggtct gtgacctgtg gctggccctg actatgtgg tgagcaatgc ctctgtcatg    360
aaccttctca tcatcagctt tgaccgctat ttctgcgtca ccaagcccct cacctatcca    420
gcccgccgca ctactaagat ggcaggcctc atgattgcag ccgcctgggt cttgtccttt    480
gtactctggg cccctgccat cttgttctgg cagtttgtgg tgggcaagag acagtgcct    540 gataaccagt gcttcatcca gttcttgtcc aacccggcgg tgaccttcgg cacagccatt    600
gctgccttct acctgcctgt ggtcatcatg acggtgctgt atattcatat ctcgctggcc    660
agccgcagcc gtgttcacaa gcatcgaccc gagggcccca aggagaagaa ggccaagact    720
ctggcttttc tcaagagccc tctgatgaag ccgagcatta agaaacctcc accaggggc    780 gcttctcgag aggaactgcg caacgggaag ctagaagagg ctcctccgcc agccctgccc    840
ccgcctccac gcccagtggc tgacaaggac acttccaatg agtccagctc aggcagtgcc    900
acccagaaca ccaaggaacg gccacccaca gagctgtcca ccacagaggc cgccaccaca    960
ccagcgctgc ccgctcctac cctgcagcca cgaaccctca acccagcctc caagtggtcc    1020
aagatccaaa ttgtgacaaa gcagacaggc agtgaatgtg tgactgccat cgagatcgta    1080
cctgccacgc cagctggtat gcgcccagca gccaatgtgg cccgaaagtt tgccagcatc    1140
gctcgtaacc aggtgcgcaa gaagcggcag atggcggccc gggagcgcaa agtgactcgg    1200
acaatctttg ccattctgct ggccttcatc ctcacctgga cacccctaca tgtcatggtc    1260
ctggtgaaca cctttttgcca gagctgtatc cccgaaaggg tgtggtccat cggctactgg    1320
ctctgctacg tcaacagcac gatcaaccct gcctgctatg cactctgcaa tgccactttc    1380
aaaaagacct tccggcacct tttgctgtgc cagtatcgga catcggcac agccaggtag    1440

<210> SEQ ID NO 5
<211> LENGTH: 1599
<212> TYPE: DNA
<213> ORGANISM: Homo sapiens

<400> SEQUENCE: 5
atggaagggg agtcttatca caatgaaacc actgtcaacg gcaccccagt aaatcaccag     60
gctttggaac gccatggact gtgggaagtc attactattg cagctgtgac cgctgtggtc    120
agtctgatga ccattgtcgg caatgtcttg gtcatgatct ccttcaaagt caacagtcag    180
ctcaagacag ttaacaacta ttacctgctc agcttggcct gtgcagacct catcattggc    240
atcttctcca tgaacctcta cacgacctac atcctcatgg gacgctgggt tctcgggagt    300
ctggcctgtg acctttggct tgcactcgac tatgtagcca gcaacgcttc tgtcatgaac    360
cttctggtga ttagctttga tcgttacttt tccatcacaa gaccactgac ataccgagcc    420
aagcgtaccc caaagagggc tggcatcatg atcggcttgg catggctggt ctccttcatc    480
ctctgggcgc cagccatcct gctggcagta cttggtcgg ggaagcggac agtaccacct    540
gatgagtgcc agatccagtt cctctctgag cccaccatca cttttgggac cgccattgcc    600
gctttctata tccctgtctc cgtcatgacc atactctact gccggatcta ccgggaaaca    660
gagaaacgaa ccaaggacct ggctgacctc caaggttccg attctgtggc agaagtcaag    720
aagagaaaac cggctcacag gaccctgctc agatctttct ttagctgccc tagacccagc    780
ctggcccaga gagtacggaa ccaggcctcc tggtcatcct cccgtagaag cacctcaaca    840
```

| | |
|---|---|
| acgggaaagc caacccaggc cactgatcta agtgctgact gggaaaaggc tgagcaggtt | 900 |
| accaactgta gcagctgccc ctcttcagag gacgaagcca aggccaccac tgaccctgtc | 960 |
| tttcaagtgg tctgcaagaa tgaggccaag gaaagcccgg ggaaggaatt caatacccaa | 1020 |
| gagaccaagg aaacgtttgt gagccctcgg actgaaaaca atgactatga cactcccaag | 1080 |
| tacttcctgt ctccaggtgc tgctcacaga ctcaagagtc agaagtgtgt tgcctataag | 1140 |
| ttccgattgg tggtaaaagc tgacgggacc caggagacaa caatggctg tcgtaaggtg | 1200 |
| aaaatcatgc cctgttcctt cccagtgtcc aaagacccct caacaaaagg cctggatccc | 1260 |
| cacctcagcc atcaaatgac caaacgaaag agaatggtcc tagtcaaaga gaggaaagcg | 1320 |
| gcgcagacct tgagcgccat tctcctggcc ttcatcatca catggactcc ttataacatc | 1380 |
| atggtcctgg tttccacctt ctgtgacaag tgtgtccctg tcaccctgtg gcacttgggt | 1440 |
| tactggctgt gctatgtcaa cagcaccatc aaccccatct gttacgctct ctgcaacaga | 1500 |
| accttcagga agaccttaa gctgctgctt ctctgccggt ggaaaaagaa aaaagtagaa | 1560 |
| gagaaattgt attggcaagg caacagcaag ctaccctga | 1599 |

<210> SEQ ID NO 6
<211> LENGTH: 684
<212> TYPE: DNA
<213> ORGANISM: Homo sapiens

<400> SEQUENCE: 6

| | |
|---|---|
| atgtgtaaga gtgtgaccac aggtgagtgg aagaaggtct tctacgagaa gatggaggag | 60 |
| gtgaagccag cggacagctg ggacttcatc atagacccca acctcaagca caatgtgttg | 120 |
| gccctggct ggaagcagta cctggaactt catgcctcag gcaggttcca ctgttcctgg | 180 |
| tgctggcaca cctggcagtc accccatgta gtcatcctct tccacatgta cctggacaag | 240 |
| gctcagcgcg ctggttcggt gcgcatgcgt gtgttcaagc agctctgcta cgagtgcggt | 300 |
| acagcacggc tggatgagtc cagcatgctg gaggagaaca tcgaaagcct ggtggacaac | 360 |
| ctcatcacca gtttgcgaga gcagtgctac ggggagcgtg gtggccacta ccgcatccat | 420 |
| gtggccagcc ggcaggacaa ccggcgcacg cgcggagagt tctgcgaggc ctgccaggaa | 480 |
| ggcatcgtgc actggaagcc cagtgagaag ctgctggagg aggaggcgac cacctacacc | 540 |
| ttctcccgtg ctcccagccc caccaaaccg caggctgaaa caggctcagg ctgcaacttc | 600 |
| tgctccattc cctggtgctt attttgggcc acggttttga tgctcatcat ctacctgcaa | 660 |
| ttctccttcc gtacttctgt ctaa | 684 |

<210> SEQ ID NO 7
<211> LENGTH: 460
<212> TYPE: PRT
<213> ORGANISM: Homo sapiens

<400> SEQUENCE: 7

Met Asn Thr Ser Val Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
            20                  25                  30

Gly Leu Leu Ser Leu Ala Thr Val Thr Gly Asn Leu Leu Val Leu Ile
        35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn

```
                65                  70                  75                  80
Leu Tyr Thr Thr Tyr Leu Leu Met Gly His Trp Ala Leu Gly Thr Leu
                    85                  90                  95

Ala Cys Asp Leu Trp Leu Ala Leu Asp Tyr Val Ala Ser Asn Ala Ser
            100                 105                 110

Val Met Asn Leu Leu Leu Ile Ser Phe Asp Arg Tyr Phe Ser Val Thr
            115                 120                 125

Arg Pro Leu Ser Tyr Arg Ala Lys Arg Thr Pro Arg Arg Ala Ala Leu
            130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                    165                 170                 175

Gln Cys Tyr Ile Gln Phe Leu Ser Gln Pro Ile Ile Thr Phe Gly Thr
                180                 185                 190

Ala Met Ala Ala Phe Tyr Leu Pro Val Thr Val Met Cys Thr Leu Tyr
            195                 200                 205

Trp Arg Ile Tyr Arg Glu Thr Glu Asn Arg Ala Arg Glu Leu Ala Ala
            210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Ser Pro Pro
                    245                 250                 255

Gly Arg Cys Cys Arg Cys Cys Arg Ala Pro Arg Leu Leu Gln Ala Tyr
                260                 265                 270

Ser Trp Lys Glu Glu Glu Glu Asp Glu Gly Ser Met Glu Ser Leu
            275                 280                 285

Thr Ser Ser Glu Gly Glu Glu Pro Gly Ser Glu Val Val Ile Lys Met
            290                 295                 300

Pro Met Val Asp Pro Glu Ala Gln Ala Pro Thr Lys Gln Pro Pro Lys
305                 310                 315                 320

Ser Ser Pro Asn Thr Val Lys Arg Pro Thr Lys Lys Gly Arg Asp Arg
                    325                 330                 335

Gly Gly Lys Gly Gln Lys Pro Arg Gly Lys Glu Gln Leu Ala Lys Arg
                340                 345                 350

Lys Thr Phe Ser Leu Val Lys Glu Lys Ala Ala Arg Thr Leu Ser
            355                 360                 365

Ala Ile Leu Leu Ala Phe Ile Leu Thr Trp Thr Pro Tyr Asn Ile Met
            370                 375                 380

Val Leu Val Ser Thr Phe Cys Lys Asp Cys Val Pro Glu Thr Leu Trp
385                 390                 395                 400

Glu Leu Gly Tyr Trp Leu Cys Tyr Val Asn Ser Thr Val Asn Pro Met
                    405                 410                 415

Cys Tyr Ala Leu Cys Asn Lys Ala Phe Arg Asp Thr Phe Arg Leu Leu
                420                 425                 430

Leu Leu Cys Arg Trp Asp Lys Arg Arg Trp Arg Lys Ile Pro Lys Arg
            435                 440                 445

Pro Gly Ser Val His Arg Thr Pro Ser Arg Gln Cys
            450                 455                 460

<210> SEQ ID NO 8
<211> LENGTH: 466
<212> TYPE: PRT
<213> ORGANISM: Homo sapiens
```

```
<400> SEQUENCE: 8

Met Asn Asn Ser Thr Asn Ser Ser Asn Gly Leu Ala Ile Thr Ser
1               5                   10                  15

Pro Tyr Lys Thr Phe Glu Val Val Phe Ile Val Leu Val Ala Gly Ser
            20                  25                  30

Leu Ser Leu Val Thr Ile Ile Gly Asn Ile Leu Val Met Val Ser Ile
        35                  40                  45

Lys Val Asn Arg His Leu Gln Thr Val Asn Asn Tyr Phe Leu Phe Ser
    50                  55                  60

Leu Ala Cys Ala Asp Leu Ile Ile Gly Val Phe Ser Met Asn Leu Tyr
65                  70                  75                  80

Thr Leu Tyr Thr Val Ile Gly Tyr Trp Pro Leu Gly Pro Val Val Cys
            85                  90                  95

Asp Leu Trp Leu Ala Leu Asp Tyr Val Val Ser Asn Ala Ser Val Met
            100                 105                 110

Asn Leu Leu Ile Ile Ser Phe Asp Arg Tyr Phe Cys Val Thr Lys Pro
            115                 120                 125

Leu Thr Tyr Pro Val Lys Arg Thr Thr Lys Met Ala Gly Met Met Ile
    130                 135                 140

Ala Ala Ala Trp Val Leu Ser Phe Ile Leu Trp Ala Pro Ala Ile Leu
145                 150                 155                 160

Phe Trp Gln Phe Ile Val Gly Val Arg Thr Val Glu Asp Gly Glu Cys
            165                 170                 175

Tyr Ile Gln Phe Phe Ser Asn Ala Ala Val Thr Phe Gly Thr Ala Ile
            180                 185                 190

Ala Ala Phe Tyr Leu Pro Val Ile Ile Met Thr Val Leu Tyr Trp His
            195                 200                 205

Ile Ser Arg Ala Ser Lys Ser Arg Ile Lys Lys Glu Lys Lys Glu Pro
            210                 215                 220

Val Ala Asn Gln Asp Pro Val Ser Pro Ser Leu Val Gln Gly Arg Ile
225                 230                 235                 240

Val Lys Pro Asn Asn Asn Asn Met Pro Gly Gly Asp Gly Gly Leu Glu
            245                 250                 255

His Asn Lys Ile Gln Asn Gly Lys Ala Pro Arg Asp Gly Gly Thr Glu
            260                 265                 270

Asn Cys Val Gln Gly Glu Glu Lys Glu Ser Ser Asn Asp Ser Thr Ser
            275                 280                 285

Val Ser Ala Val Ala Ser Asn Met Arg Asp Asp Glu Ile Thr Gln Asp
    290                 295                 300

Glu Asn Thr Val Ser Thr Ser Leu Gly His Ser Lys Asp Asp Asn Ser
305                 310                 315                 320

Arg Gln Thr Cys Ile Lys Ile Val Thr Lys Thr Gln Lys Gly Asp Ala
            325                 330                 335

Cys Thr Pro Thr Ser Thr Thr Val Glu Leu Val Gly Ser Ser Gly Gln
            340                 345                 350

Asn Gly Asp Glu Lys Gln Asn Ile Val Ala Arg Lys Ile Val Lys Met
            355                 360                 365

Thr Lys Gln Pro Ala Lys Lys Lys Pro Pro Ser Arg Glu Lys Lys
            370                 375                 380

Val Thr Arg Thr Ile Leu Ala Ile Leu Leu Ala Phe Ile Ile Thr Trp
385                 390                 395                 400

Ala Pro Tyr Asn Val Met Val Leu Ile Asn Thr Phe Cys Ala Pro Cys
```

```
                    405                 410                 415
Ile Pro Asn Thr Val Trp Thr Ile Gly Tyr Trp Leu Cys Tyr Ile Asn
            420                 425                 430

Ser Thr Ile Asn Pro Ala Cys Tyr Ala Leu Cys Asn Ala Thr Phe Lys
            435                 440                 445

Lys Thr Phe Lys His Leu Leu Met Cys His Tyr Lys Asn Ile Gly Ala
            450                 455                 460

Thr Arg
465

<210> SEQ ID NO 9
<211> LENGTH: 589
<212> TYPE: PRT
<213> ORGANISM: Homo sapiens

<400> SEQUENCE: 9

Met Thr Leu His Ser Asn Ser Thr Thr Ser Pro Leu Phe Pro Asn Ile
1               5                   10                  15

Ser Ser Ser Trp Val His Ser Pro Ser Glu Ala Gly Leu Pro Leu Gly
            20                  25                  30

Thr Val Ser Gln Leu Asp Ser Tyr Asn Ile Ser Gln Thr Ser Gly Asn
        35                  40                  45

Phe Ser Ser Asn Asp Thr Ser Ser Asp Pro Leu Gly Gly His Thr Ile
    50                  55                  60

Trp Gln Val Val Phe Ile Ala Phe Leu Thr Gly Phe Leu Ala Leu Val
65                  70                  75                  80

Thr Ile Ile Gly Asn Ile Leu Val Ile Val Ala Phe Lys Val Asn Lys
                85                  90                  95

Gln Leu Lys Thr Val Asn Asn Tyr Phe Leu Leu Ser Leu Ala Cys Ala
            100                 105                 110

Asp Leu Ile Ile Gly Val Ile Ser Met Asn Leu Phe Thr Thr Tyr Ile
        115                 120                 125

Ile Met Asn Arg Trp Ala Leu Gly Asn Leu Ala Cys Asp Leu Trp Leu
    130                 135                 140

Ser Ile Asp Tyr Val Ala Ser Asn Ala Ser Val Met Asn Leu Leu Val
145                 150                 155                 160

Ile Ser Phe Asp Arg Tyr Phe Ser Ile Thr Arg Pro Leu Thr Tyr Arg
                165                 170                 175

Ala Lys Arg Thr Thr Lys Arg Ala Gly Val Met Ile Gly Leu Ala Trp
            180                 185                 190

Val Ile Ser Phe Val Leu Trp Ala Pro Ala Ile Leu Phe Trp Gln Tyr
        195                 200                 205

Phe Val Gly Lys Arg Thr Val Pro Pro Gly Glu Cys Phe Ile Gln Phe
    210                 215                 220

Leu Ser Glu Pro Thr Ile Thr Phe Gly Thr Ala Ile Ala Ala Phe Tyr
225                 230                 235                 240

Met Pro Val Thr Ile Met Thr Ile Leu Tyr Trp Arg Ile Tyr Lys Glu
                245                 250                 255

Thr Glu Lys Arg Thr Lys Glu Leu Ala Gly Leu Gln Ala Ser Gly Thr
            260                 265                 270

Glu Ala Glu Ala Glu Asn Phe Val His Pro Thr Gly Ser Ser Arg Ser
        275                 280                 285

Cys Ser Ser Tyr Glu Leu Gln Gln Gln Gly Thr Lys Arg Ser Ser Arg
    290                 295                 300
```

Arg Lys Tyr Gly Gly Cys His Phe Trp Phe Thr Lys Ser Trp Lys
305                 310                 315                 320

Pro Ser Ala Glu Gln Met Asp Gln Asp His Ser Ser Asp Ser Trp
            325                 330                 335

Asn Asn Asn Asp Ala Ala Ala Ser Leu Glu Asn Ser Ala Ser Ser Asp
                340                 345                 350

Glu Glu Asp Ile Gly Ser Glu Thr Arg Ala Ile Tyr Ser Ile Val Leu
            355                 360                 365

Lys Leu Pro Gly His Ser Thr Ile Leu Asn Ser Thr Lys Leu Pro Ser
        370                 375                 380

Ser Asp Asn Leu Gln Val Pro Asp Lys Asp Leu Gly Thr Met Asp Val
385                 390                 395                 400

Glu Arg Asn Ala His Lys Leu Gln Ala Gln Lys Ser Met Asp Asp Arg
                405                 410                 415

Asp Asn Cys Gln Lys Asp Phe Ser Lys Leu Pro Ile Gln Leu Glu Ser
                420                 425                 430

Ala Val Asp Thr Ala Lys Thr Ser Asp Thr Asn Ser Ser Val Asp Lys
            435                 440                 445

Thr Thr Ala Ala Leu Pro Leu Ser Phe Lys Glu Ala Thr Leu Ala Lys
450                 455                 460

Arg Phe Ala Leu Lys Thr Arg Ser Gln Ile Thr Lys Arg Lys Arg Met
465                 470                 475                 480

Ser Leu Ile Lys Glu Lys Lys Ala Ala Gln Thr Leu Ser Ala Ile Leu
                485                 490                 495

Leu Ala Phe Ile Ile Thr Trp Thr Pro Tyr Asn Ile Met Val Leu Val
            500                 505                 510

Asn Thr Phe Cys Asp Ser Cys Ile Pro Lys Thr Tyr Trp Asn Leu Gly
            515                 520                 525

Tyr Trp Leu Cys Tyr Ile Asn Ser Thr Val Asn Pro Val Cys Tyr Ala
        530                 535                 540

Leu Cys Asn Lys Thr Phe Arg Thr Thr Phe Lys Met Leu Leu Leu Cys
545                 550                 555                 560

Gln Cys Asp Lys Arg Lys Arg Arg Lys Gln Gln Tyr Gln Gln Arg Gln
                565                 570                 575

Ser Val Ile Phe His Lys Arg Val Pro Glu Gln Ala Leu
            580                 585

<210> SEQ ID NO 10
<211> LENGTH: 479
<212> TYPE: PRT
<213> ORGANISM: Homo sapiens

<400> SEQUENCE: 10

Met Ala Asn Phe Thr Pro Val Asn Gly Ser Ser Ala Asn Gln Ser Val
1                   5                   10                  15

Arg Leu Val Thr Thr Ala His Asn His Leu Glu Thr Val Glu Met Val
            20                  25                  30

Phe Ile Ala Thr Val Thr Gly Ser Leu Ser Leu Val Thr Val Val Gly
        35                  40                  45

Asn Ile Leu Val Met Leu Ser Ile Lys Val Asn Arg Gln Leu Gln Thr
    50                  55                  60

Val Asn Asn Tyr Phe Leu Phe Ser Leu Ala Cys Ala Asp Leu Ile Ile
65                  70                  75                  80

Gly Ala Phe Ser Met Asn Leu Tyr Thr Leu Tyr Ile Ile Lys Gly Tyr
                85                  90                  95

Trp Pro Leu Gly Ala Val Val Cys Asp Leu Trp Leu Ala Leu Asp Tyr
            100                 105                 110

Val Val Ser Asn Ala Ser Val Met Asn Leu Leu Ile Ile Ser Phe Asp
        115                 120                 125

Arg Tyr Phe Cys Val Thr Lys Pro Leu Thr Tyr Pro Ala Arg Arg Thr
    130                 135                 140

Thr Lys Met Ala Gly Leu Met Ile Ala Ala Trp Val Leu Ser Phe
145                 150                 155                 160

Val Leu Trp Ala Pro Ala Ile Leu Phe Trp Gln Phe Val Val Gly Lys
                165                 170                 175

Arg Thr Val Pro Asp Asn Gln Cys Phe Ile Gln Phe Leu Ser Asn Pro
                180                 185                 190

Ala Val Thr Phe Gly Thr Ala Ile Ala Ala Phe Tyr Leu Pro Val Val
            195                 200                 205

Ile Met Thr Val Leu Tyr Ile His Ile Ser Leu Ala Ser Arg Ser Arg
        210                 215                 220

Val His Lys His Arg Pro Glu Gly Pro Lys Glu Lys Lys Ala Lys Thr
225                 230                 235                 240

Leu Ala Phe Leu Lys Ser Pro Leu Met Lys Pro Ser Ile Lys Lys Pro
                245                 250                 255

Pro Pro Gly Gly Ala Ser Arg Glu Glu Leu Arg Asn Gly Lys Leu Glu
            260                 265                 270

Glu Ala Pro Pro Pro Ala Leu Pro Pro Pro Arg Pro Val Ala Asp
            275                 280                 285

Lys Asp Thr Ser Asn Glu Ser Ser Gly Ser Ala Thr Gln Asn Thr
290                 295                 300

Lys Glu Arg Pro Pro Thr Glu Leu Ser Thr Thr Glu Ala Ala Thr Thr
305                 310                 315                 320

Pro Ala Leu Pro Ala Pro Thr Leu Gln Pro Arg Thr Leu Asn Pro Ala
                325                 330                 335

Ser Lys Trp Ser Lys Ile Gln Ile Val Thr Lys Gln Thr Gly Ser Glu
            340                 345                 350

Cys Val Thr Ala Ile Glu Ile Val Pro Ala Thr Pro Ala Gly Met Arg
        355                 360                 365

Pro Ala Ala Asn Val Ala Arg Lys Phe Ala Ser Ile Ala Arg Asn Gln
370                 375                 380

Val Arg Lys Lys Arg Gln Met Ala Ala Arg Glu Arg Lys Val Thr Arg
385                 390                 395                 400

Thr Ile Phe Ala Ile Leu Leu Ala Phe Ile Leu Thr Trp Thr Pro Tyr
                405                 410                 415

Asn Val Met Val Leu Val Asn Thr Phe Cys Gln Ser Cys Ile Pro Glu
            420                 425                 430

Arg Val Trp Ser Ile Gly Tyr Trp Leu Cys Tyr Val Asn Ser Thr Ile
        435                 440                 445

Asn Pro Ala Cys Tyr Ala Leu Cys Asn Ala Thr Phe Lys Lys Thr Phe
450                 455                 460

Arg His Leu Leu Leu Cys Gln Tyr Arg Asn Ile Gly Thr Ala Arg
465                 470                 475

<210> SEQ ID NO 11
<211> LENGTH: 532
<212> TYPE: PRT
<213> ORGANISM: Homo sapiens

<400> SEQUENCE: 11

```
Met Glu Gly Glu Ser Tyr His Asn Glu Thr Thr Val Asn Gly Thr Pro
1               5                   10                  15

Val Asn His Gln Ala Leu Glu Arg His Gly Leu Trp Glu Val Ile Thr
            20                  25                  30

Ile Ala Ala Val Thr Ala Val Val Ser Leu Met Thr Ile Val Gly Asn
        35                  40                  45

Val Leu Val Met Ile Ser Phe Lys Val Asn Ser Gln Leu Lys Thr Val
    50                  55                  60

Asn Asn Tyr Tyr Leu Leu Ser Leu Ala Cys Ala Asp Leu Ile Ile Gly
65                  70                  75                  80

Ile Phe Ser Met Asn Leu Tyr Thr Thr Tyr Ile Leu Met Gly Arg Trp
                85                  90                  95

Val Leu Gly Ser Leu Ala Cys Asp Leu Trp Leu Ala Leu Asp Tyr Val
            100                 105                 110

Ala Ser Asn Ala Ser Val Met Asn Leu Leu Val Ile Ser Phe Asp Arg
        115                 120                 125

Tyr Phe Ser Ile Thr Arg Pro Leu Thr Tyr Arg Ala Lys Arg Thr Pro
130                 135                 140

Lys Arg Ala Gly Ile Met Ile Gly Leu Ala Trp Leu Val Ser Phe Ile
145                 150                 155                 160

Leu Trp Ala Pro Ala Ile Leu Cys Trp Gln Tyr Leu Val Gly Lys Arg
                165                 170                 175

Thr Val Pro Pro Asp Glu Cys Gln Ile Gln Phe Leu Ser Glu Pro Thr
            180                 185                 190

Ile Thr Phe Gly Thr Ala Ile Ala Ala Phe Tyr Ile Pro Val Ser Val
        195                 200                 205

Met Thr Ile Leu Tyr Cys Arg Ile Tyr Arg Glu Thr Glu Lys Arg Thr
210                 215                 220

Lys Asp Leu Ala Asp Leu Gln Gly Ser Asp Ser Val Ala Glu Val Lys
225                 230                 235                 240

Lys Arg Lys Pro Ala His Arg Thr Leu Leu Arg Ser Phe Phe Ser Cys
                245                 250                 255

Pro Arg Pro Ser Leu Ala Gln Arg Val Arg Asn Gln Ala Ser Trp Ser
            260                 265                 270

Ser Ser Arg Arg Ser Thr Ser Thr Thr Gly Lys Pro Thr Gln Ala Thr
        275                 280                 285

Asp Leu Ser Ala Asp Trp Glu Lys Ala Glu Gln Val Thr Asn Cys Ser
    290                 295                 300

Ser Cys Pro Ser Ser Glu Asp Glu Ala Lys Ala Thr Thr Asp Pro Val
305                 310                 315                 320

Phe Gln Val Val Cys Lys Asn Glu Ala Lys Glu Ser Pro Gly Lys Glu
                325                 330                 335

Phe Asn Thr Gln Glu Thr Lys Glu Thr Phe Val Ser Pro Arg Thr Glu
            340                 345                 350

Asn Asn Asp Tyr Asp Thr Pro Lys Tyr Phe Leu Ser Pro Gly Ala Ala
        355                 360                 365

His Arg Leu Lys Ser Gln Lys Cys Val Ala Tyr Lys Phe Arg Leu Val
    370                 375                 380

Val Lys Ala Asp Gly Thr Gln Glu Thr Asn Asn Gly Cys Arg Lys Val
385                 390                 395                 400

Lys Ile Met Pro Cys Ser Phe Pro Val Ser Lys Asp Pro Ser Thr Lys
                405                 410                 415
```

-continued

```
Gly Leu Asp Pro His Leu Ser His Gln Met Thr Lys Arg Lys Arg Met
            420             425             430

Val Leu Val Lys Glu Arg Lys Ala Ala Gln Thr Leu Ser Ala Ile Leu
            435             440             445

Leu Ala Phe Ile Ile Thr Trp Thr Pro Tyr Asn Ile Met Val Leu Val
            450             455             460

Ser Thr Phe Cys Asp Lys Cys Val Pro Val Thr Leu Trp His Leu Gly
465             470             475             480

Tyr Trp Leu Cys Tyr Val Asn Ser Thr Ile Asn Pro Ile Cys Tyr Ala
                485             490             495

Leu Cys Asn Arg Thr Phe Arg Lys Thr Phe Lys Leu Leu Leu Leu Cys
            500             505             510

Arg Trp Lys Lys Lys Val Glu Glu Lys Leu Tyr Trp Gln Gly Asn
            515             520             525

Ser Lys Leu Pro
530
```